US005631401A

United States Patent [19]

Stein et al.

[11] Patent Number: 5,631,401
[45] Date of Patent: May 20, 1997

[54] INHIBITORS OF PROTEIN FARNESYLTRANSFERASE AND SQUALENE SYNTHASE

[75] Inventors: Herman H. Stein, Highland Park, Ill.; William R. Baker, Bellevue, Wash.; Anthony K. L. Fung, Gurnee, Ill.; Saul H. Rosenberg, Grayslake, Ill.; Todd W. Rockway, Grayslake, Ill.; Stephen A. Fakhoury, Mundelein, Ill.; David S. Garvey, Waltham, Mass.; B. Gregory Donner, Mundelein, Ill.; William J. McClellan, Waukegan, Ill.; Stephen J. O'Connor, Wilmette, Ill.; Rajnandan Prasad, Vernon Hills, Ill.; Wang Shen, Skokie, Ill.; Gerard M. Sullivan, Round Lake Beach, Ill.

[73] Assignee: Abbott Laboratories, Abbott Park, Ill.

[21] Appl. No.: 378,334

[22] Filed: Jan. 24, 1995

Related U.S. Application Data

[63] Continuation-in-part of Ser. No. 194,366, Feb. 9, 1994, abandoned.

[51] Int. Cl.$^6$ ........................ C07C 229/46; A61K 31/19; A61K 31/195
[52] U.S. Cl. ........................ 562/451; 562/432; 562/441; 562/442; 562/457; 562/505; 560/42; 560/123; 560/251; 546/146; 546/189; 546/262; 548/187; 548/561; 549/65; 549/77; 549/438; 549/460; 549/479; 549/493; 514/307; 514/316; 514/332; 514/369; 514/427; 514/438; 514/445; 514/461; 514/466; 514/468; 514/471; 514/533; 514/548; 514/562; 514/563
[58] Field of Search ........................ 562/451, 441, 562/442, 505, 432, 457; 560/42, 123, 251; 514/533, 548, 563, 307, 316, 332, 369, 427, 438, 445, 461, 466, 468, 471, 562; 546/146, 189, 262; 548/187, 561; 549/65, 77, 438, 460, 479, 493

[56] References Cited

U.S. PATENT DOCUMENTS

| 4,340,715 | 7/1982 | Gouder et al. | 528/99 |
| 4,570,014 | 2/1986 | Schroder et al. | 560/124 |
| 5,102,907 | 4/1992 | Bergstrom et al. | 514/456 |
| 5,126,345 | 6/1992 | Slusarchyk et al. | 514/254 |
| 5,240,946 | 8/1993 | Kinney et al. | 514/364 |
| 5,245,061 | 9/1993 | Singh | 554/121 |
| 5,260,465 | 11/1993 | Singh et al. | 554/134 |
| 5,260,479 | 11/1993 | Singh et al. | 560/190 |
| 5,344,962 | 9/1994 | Ahmad | 560/123 |

FOREIGN PATENT DOCUMENTS

| 448393 | 9/1991 | European Pat. Off. . |
| 503520 | 9/1992 | European Pat. Off. . |
| 526936 | 2/1993 | European Pat. Off. . |
| WO92/12158 | 7/1992 | WIPO . |
| WO94/22870 | 10/1994 | WIPO . |

OTHER PUBLICATIONS

Moore et al., *Chem. Mat.*, 1, pp. 163–166 (1989).

Ortiz de Montellano, Paul R., et al. "Prenyl Substituted Cyclobutanones As Squalene Synthetase Inhibitors" Tetrahedron Letters No. 346, pp. 4115–4118, 1976.

*Primary Examiner*—Gary Geist
*Assistant Examiner*—Barbara S. Frazier
*Attorney, Agent, or Firm*—Gregory W. Steele; Steven R. Crowley

[57] ABSTRACT

The present invention provides a compound of the formula

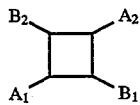

or a pharmaceutically acceptable salt thereof, which are useful in inhibiting protein farnesyltransferase and the farnesylation of the oncogene protein Ras or inhibiting de novo squalene production resulting in the inhibition of cholesterol biosynthesis, processes for the preparation of the compounds of the invention in addition to intermediates useful in these processes, a pharmaceutical composition, and to methods of using such compounds.

14 Claims, No Drawings

INHIBITORS OF PROTEIN FARNESYLTRANSFERASE AND SQUALENE SYNTHASE

This application is a continuation-in-part of U.S. patent application Ser. No. 194,366, filed Feb. 9, 1994, now abandoned.

TECHNICAL FIELD

The present invention relates to new cyclobutane dicarboxylic acid compounds which are useful in inhibiting protein farnesyltransferase and the farnesylation of the oncogene protein Ras or inhibiting de novo squalene production resulting in the inhibition of cholesterol biosynthesis, compositions containing such compounds and to methods of using such compounds.

BACKGROUND OF THE INVENTION

Transformed protein Ras is involved in the proliferation of cancer cells. The Ras must be farnesylated before this proliferation can occur. Farnesylation of Ras by farnesyl pyrophosphate (FPP) is effected by protein farnesyltransferase. Inhibition of protein farnesyltransferase and, thereby, of farnesylation of the Ras protein, blocks the ability of transformed cells to proliferate.

Activation of Ras also partially mediates smooth muscle cell proliferation (Circulation, I-3:88 (1993). Inhibition of protein farnesyltransferase and, thereby, of farnesylation of the Ras protein, will aid in the prevention of restenosis.

The compounds of the invention are also inhibitors of squalene synthase. Squalene synthase is a microsomal enzyme which catalyzes the reductive dimerization of two molecules of farnesyl pyrophosphate (FPP) in the presence of nicotinamide adenine dinucleotide phosphate, reduced form, (NADPH) to form squalene (Poulter, C. D., Rilling, H. C., in "Biosynthesis of Isoprenoid Compounds", Vol. I, Chapter 8, pp. 413–441, J. Wiley and Sons, 1981 and references therein). This enzyme is the first committed step of the de novo cholesterol biosynthetic pathway. Thus inhibitors of squalene synthase cause inhibition of cholesterol biosynthesis and thus act as a hypocholesterolemic agents. Thus squalene synthase inhibitors are useful for the treatment and prevention of hyperlipidemia or atherosclerosis or other disorders resulting from an excess of cholesterol.

Inhibition of squalene synthase also results in the inhibition of fungal growth.

DISCLOSURE OF THE INVENTION

In accordance with the present invention there are provided cyclobutane compounds of formula (I):

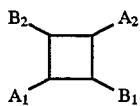

wherein $A_1$ and $A_2$ are independently selected from
(1) —C(O)NR$_1$R$_2$ wherein R$_1$ at each occurrence is independently selected from (i) hydrogen, (ii) loweralkyl, (iii) cycloalkyl, (iv) cycloalkylalkyl, (v) aryl, (vi) arylalkyl, (vii) heterocyclic, (viii) alkenyl, (ix) alkynyl, (x) alkoxylcarbonylalkyl, (xi) carboxyalkyl, (xii) alkoxyalkyl, (xiii) hydroxyalkyl, (xiv) thioalkoxyalkyl, (xv) aryl substituted thioalkoxyalkyl, (xvi) heterocyclicalkyl, (xvii) aryloxyarylalkyl, (xviii) aryloxyalkyl and (xix) aryl, arylalkyl or heterocyclicalkyl wherein the aryl group, the the aryl part of the arylalkyl group or the heterocyclic part of the heterocyclicalkyl group is substituted with —Z—R$_8$ wherein at each occurrence Z is independently selected from (a) a covalent bond, (b) —C(O)—, (c) —CH$_2$—, (d) —O—, (e) —S(O)$_p$— wherein p is 0, 1 or 2, (f) —N(R$_c$)— wherein R$_c$ is hydrogen or loweralkyl, (g) —CH$_2$O—, (h) —CH$_2$S(O)$_p$— wherein p is 0, 1 or 2 and (i) —CH$_2$N(R$_c$)— wherein R$_c$ is hydrogen or loweralkyl and at each occurrence R$_8$ is independently selected from (a) aryl, (b) arylalkyl, (c) cycloalkyl, (d) cycloalkylalkyl, (e) heterocyclic and (f) heterocyclicalkyl, and R$_2$ at each occurrence is independently selected from (i) aryl, (ii) arylalkyl, (iii) alkenyl, (iv) alkynyl, (v) arylalkenyl, (vi) arylalkynyl, (vii) heterocyclicalkyl, (viii) aryloxyalkyl, (ix) arylalkyl wherein the alkyl group is substituted with —OR$_{10}$ wherein R$_{10}$ is hydrogen or alkanoyl and (x) aryl, arylalkyl or heterocyclicalkyl wherein the aryl group, the the aryl part of the arylalkyl group or the heterocyclic part of the heterocyclicalkyl group is substituted with —Y—R$_3$ wherein at each occurrence Y is independently selected from (a) a covalent bond, (b) —C(O)—, (c) —CH$_2$—, (d) —O—, (e) —S(O)$_m$— wherein m is 0, 1 or 2, (f) —N(R$_b$)— wherein R$_b$ is hydrogen or loweralkyl, (g) —CH$_2$O—, (h) —CH$_2$S(O)$_m$— wherein m is 0, 1 or 2 and (i) —CH$_2$N(R$_b$)— wherein R$_b$ is hydrogen or loweralkyl and at each occurrence R$_3$ is independently selected from (a) aryl, (b) arylalkyl, (c) cycloalkyl, (d) cycloalkylalkyl, (e) heterocyclic and (f) (heterocyclic)alkyl, or R$_1$ and R$_2$ taken together with the nitrogen atom to which they are attached form a nitrogen-containing heterocycle;

(2) —(CH$_2$)$_n$—NR$_1$R$_2$ wherein R$_1$ and R$_2$ are as defined above and n is 0, 1 or 2;

(3) —NH—C(O)—NR$_1$R$_2$ wherein R$_1$ and R$_2$ are as defined above; and (4) —C(O)OR$_4$ wherein R$_4$ is (i) aryl, (ii) arylalkyl, (iii) arylalkyl substituted arylalkyl, (iv) aryloxyarylalkyl, (v) aryloxyaryl, (vi) arylalkoxyarylalkyl, (vii) arylalkoxyaryl, (viii) arylaryl, (ix) arylalkylaryl, (x) alkenyl or (xi) alkynyl;

B$_1$ and B$_2$ are independently selected from
(1) —OH$_2$OH,
(2) —CH=NOH,
(3) —W—R$_5$ wherein at each occurrence W is independently selected from (a) a covalent bond, (b) alkylene, (c) alkenylene, (d) —C(O)NH— and (e) —NHC(O)NH— and R$_5$ is independently selected from (a) 5-tetrazolyl, (b) 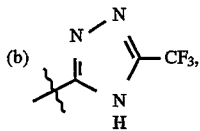

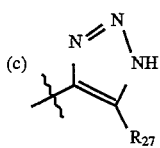

wherein R$_{27}$ is —CN, —NO$_2$, or
—CO$_2$R$_{28}$ wherein R$_{28}$ is hydrogen, aryl or loweralkyl,

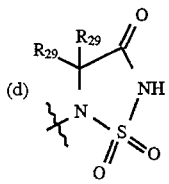

wherein at each occurrence R$_{29}$ is selected from hydrogen and loweralkyl,

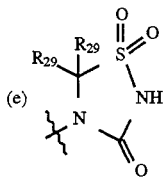

wherein R$_{29}$ is a defined above,

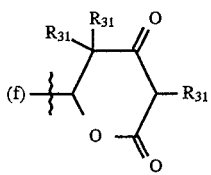

wherein at each occurrence R$_{31}$ is selected from hydrogen, loweralkyl, alkenyl, alkoxyalkyl and benzyl,

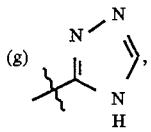

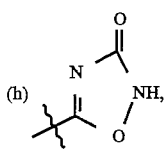

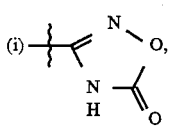

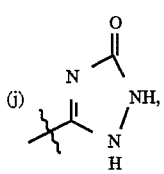

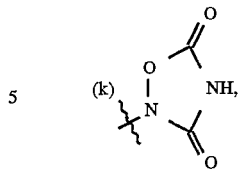

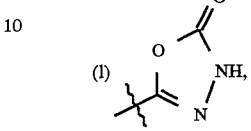

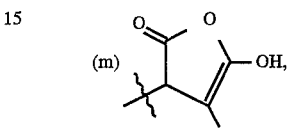

and

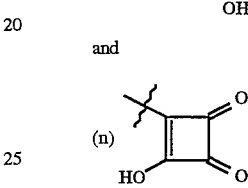

(4) —Q—C(O)R$_6$ wherein at each occurrence Q is independently selected from (a) a covalent bond, (b) alkylene, (c) alkenylene, (d) —CH(OH)— and (e) —NHC(O)(CH$_2$)$_r$— wherein r is 0 to 4 and at each occurrence R$_6$ is independently selected from (a) —OR$_7$ wherein R$_7$ is hydrogen or a carboxy-protecting group, (b) —NH$_2$, (c) —NHOH, (d) —NHSO$_2$CF$_3$ (e) an alpha-amino acid or a beta-amino acid which is bonded via the alpha- or beta-amino group and (f) a di-, tri- or tetra-peptide which is bonded via the amino terminal amino group, (5) —CH$_2$—N(OH)—C(O)—R$_{25}$ wherein R$_{25}$ is hydrogen, methyl or trifluoromethyl, and (6) —C(O)—NH—S(O)$_2$—R$_{26}$ wherein R$_{26}$ is aryl, heterocyclic, arylalkyl, (heterocyclic)alkyl, C$_3$–C$_7$-cycloalkyl, C$_1$–C$_6$-alkyl or perfluoro-C$_1$–C$_4$-alkyl, or a pharmaceutically acceptable salt thereof.

Preferred compounds of the invention are compounds of formula (II)

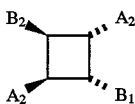

wherein A$_1$, A$_2$, B$_1$ and B$_2$ are as defined above;
or a pharmaceutically acceptable salt thereof.

Preferred compounds of the invention are compounds of formula (I) or (II) wherein A$_1$ and A$_2$ are independently —C(O)NR$_1$R$_2$ wherein at each occurrence R$_1$ is independently selected from (i) hydrogen, (ii) loweralkyl, (iii) cycloalkyl, (iv) cycloalkylalkyl, (v) aryl, (vi) arylalkyl, (vii) arylalkyl substituted arylalkyl, (viii) aryloxyaryl, (ix) aryloxyarylalkyl, (x) arylalkoxyarylalkyl, (xi) arylalkoxyaryl, (xii) alkenyl, (xiii) alkynyl, (xiv) carboxyalkyl, and (xv) heterocyclicalkyl; and R$_2$ at each occurrence is independently selected from (i) aryl, (ii) arylalkyl, (iii) alkenyl, (iv) alkynyl, (v) arylalkenyl, (vi) arylalkynyl, (vii) heterocyclicalkyl, (viii) aryloxyalkyl, (ix) arylalkyl wherein the alkyl group is substituted with —OR$_{10}$ wherein R$_{10}$ is hydrogen or alkanoyl and (x) aryl, arylalkyl or heterocyclicalkyl wherein the aryl group, the the aryl part of the arylalkyl group or the heterocyclic part of the heterocyclicalkyl group is substituted with —Y—$R_3$ wherein at each occurrence Y is independently selected from (a) a covalent bond, (b) —C(O)—, (c) —$CH_2$—, (d) —O—, (e) —S—, (f) —NH—, and (g) —$CH_2O$—, and at each occurrence $R_3$ is independently selected from (a) aryl, (b) arylalkyl, (c) cycloalkyl, (d) cycloalkylalkyl, (e) heterocyclic and (f) (heterocyclic)alkyl, or $R_1$ and $R_2$ taken together with the nitrogen atom to which they are attached form a nitrogen-containing heterocycle; and $B_1$ and $B_2$ are independently —C(O)—$OR_7$ wherein at each occurrence $R_7$ is independently selected from hydrogen and a carboxy protecting group;

or a pharmaceutically acceptable salt thereof.

More preferred compounds of the invention are compounds of formula (I) or (II) wherein $A_1$ and $A_2$ are independently —C(O)$NR_1R_2$ wherein at each occurrence at each occurrence $R_1$ is independently selected from (i) loweralkyl, (ii) arylalkyl, (iii) cycloalkyl, (iv) carboxyalkyl, and (v) heterocyclicalkyl and at each occurrence $R_2$ is independently selected from (i) arylalkyl, (ii) arylalkenyl, and (iii) arylalkyl or heterocyclicalkyl wherein the the aryl part of the arylalkyl group or the heterocyclic part of the heterocyclicalkyl group is substituted with —Y—$R_3$ wherein at each occurrence Y is independently selected from (a) —$CH_2$— and (b) —O—, at each occurrence $R_3$ is independently selected from (a) aryl, (b) arylalkyl, (c) heterocyclic and (d) (heterocyclic)alkyl, or $R_1$ and $R_2$ taken together with the nitrogen atom to which they are attached form a nitrogen-containing heterocycle; and $B_1$ and $B_2$ are independently —C(O)—$OR_7$ wherein at each occurrence $R_7$ is independently selected from hydrogen and a carboxy protecting group;

or a pharmaceutically acceptable salt thereof.

Even more preferred compounds of the invention are compounds of formula (I) or (II) wherein $A_1$ and $A_2$ are independently —C(O)$NR_1R_2$ wherein at each occurrence $R_1$ is independently selected from (i) loweralkyl, (ii) arylalkyl, (iii) cycloalkyl, (iv) carboxyalkyl, and (v) heterocyclicalkyl and at each occurrence $R_2$ is independently selected from 4-(phenoxy)benzyl, 3-(phenoxy)benzyl, 3-(4-fluorophenoxy)benzyl, 4-(benzyl)benzyl, benzyl, 5-phenylpentyl, 4-(phenoxymethyl)benzyl, 4-acetoxy-5-methyl-6-phenylhexyl, 2-methyl-5-phenylpentyl, and E-2-methyl-5-phenylpent-4-enyl, or $R_1$ and $R_2$ taken together with the nitrogen atom to which they are attached is 4-(4-phenoxyphenyl)-1,2,3,6-tetrahydropyridin-1-yl; and $B_1$ and $B_2$ are independently —C(O)—$OR_7$ wherein at each occurrence $R_7$ is independently selected from hydrogen and a carboxy protecting group; or a pharmaceutically acceptable salt thereof.

Most preferred compounds of the invention are compounds of formula (I) or (II) wherein $A_1$ and $A_2$ are independently —C(O)$NR_1R_2$ wherein at each occurrence $R_1$ is independently selected from (i) lowerlakyl, (ii) cycloalkyl, (iii) benzyl, (iv) 4-fluorobenzyl, (v) 1-phenylethyl, (vi) carboxymethyl, (vii) furan-2-ylmethyl and thien-2-ylmethyl and at each occurrence $R_2$ is independently selected from 4-(phenoxy)benzyl, 3-(phenoxy)benzyl, 3-(4-fluorophenoxy)benzyl, 4-(benzyl)benzyl, benzyl, 5-phenylpentyl, 4-(phenoxymethyl)benzyl, 4-acetoxy-5-methyl-6-phenylhexyl, 2-methyl-5-phenylpentyl, and E-2-methyl-5-phenylpent-4-enyl, or $R_1$ and $R_2$ taken together with the nitrogen atom to which they are attached is 4-(4-phenoxyphenyl)-1,2,3,6-tetrahydropyridin-1-yl; and $B_1$ and $B_2$ are independently —C(O)—$OR_7$ wherein at each occurrence $R_7$ is independently selected from hydrogen and a carboxy protecting group; or a pharmaceutically acceptable salt thereof.

The present invention also relates to processes for preparing the the compounds of formula (I) or (II) and to the synthetic intermediates useful in such processes.

In a further aspect of the present invention are disclosed pharmaceutical compositions which comprise a compound of the present invention in combination with a pharmaceutically acceptable carrier.

In yet another aspect of the present invention are disclosed pharmaceutical compositions which comprise a compound of the present invention in combination with another chemotherapeutic agent and a pharmaceutically acceptable carrier.

In yet another aspect of the present invention is disclosed a method of inhibiting protein farnesyltransferase in a human or lower mammal, comprising administering to the patient a therapeutically effective amount of a compound of the invention.

In yet another aspect of the present invention are disclosed pharmaceutical compositions which comprise a compound of the present invention in combination with another antihyperlipoproteinemic agent and/or with one or more other serum cholesterol lowering agents or HMG CoA reductase inhibitors and a pharmaceutically acceptable carrier.

In yet another aspect of the present invention is disclosed a method of treating cancer in a human or lower mammal, comprising administering to the patient a therapeutically effective amount of a compound of the invention alone or in combination with another chemotherapeutic agent In yet another aspect of the present invention is disclosed a method of preventing restenosis in a human or lower mammal, comprising administering to the patient a therapeutically effective amount of a compound of the invention.

In yet another aspect of the present invention is disclosed a method of inhibiting squalene synthase in a human or lower mammal, comprising administering to the patient a therapeutically effective amount of a compound of the invention.

In yet another aspect of the present invention is disclosed a method of inhibiting or treating atherosclerosis or inhibiting or treating hyperlipidemia which would inhibit the development of atherosclerosis in a human or lower mammal, comprising administering to the patient a therapeutically effective amount of a compound of the invention alone or in combination with another cardiovascular agent.

Also disclosed is a method of treating fungal infections in a human or lower mammal, comprising administering to the patient a therapeutically effective amount of a compound of the invention.

Also disclosed is a method for treating acne in humans.

The compounds of the invention comprise asymmetrically substituted carbon atoms. As a result, all stereoisomers of the compounds of the invention are meant to be included in the invention, including racemic mixtures, mixtures of diastereomers, as well as single diastereomers of the compounds of the invention. Methods for preparing various stereoisomers are described in E. M. White and H. C. Dunathan, J. Amer. Chem. Soc., 78:6055–6057 (1956), R. Crigee and H. Hover, Chem. Ber., 93:2521–2524 (1960) and R. Crigee and W. Funke, Chem Ber., 94:2538–2539 (1961). The terms "S" and "R" configuration, as used herein, are as defined by the IUPAC 1974 Recommendations for Section E, Fundamental Stereochemistry, Pure Appl. Chem. (1976) 45, 13–30.

The terms α and β are employed to describe relative orientation for ring substituents on cyclic compounds, i.e., substituted cyclobutanes in the present invention. The α-side of the reference plane (the plane formed by the cyclobutane ring) is that side on which the highest ranking substituent (according to the Cahn-Ingold-Prelog Sequence Rule) lies at the lowest-numbered stereogenic carbon atom. All substituents lying on the same side of the reference plane as the highest-ranking substituent are assigned an α descriptor. Those substituents lying on the opposite side of the reference plane are assigned a β descriptor. It should be noted that this usage does not describe absolute configuration. The terms α and β configuration, as used herein, are as defined by the Chemical Abstracts Index Guide-Appendix IV (1987) ¶203.

The term "α-amino acid" or "alpha-amino acid" refers to α-amino acid selected from the group consisting of alanine, arginine, asparagine, aspartic acid, cysteine, glutamine, glutamic acid, glycine, histidine, isoleucine, leucine, lysine, methionine, norleucine, ornithine, phenylalanine, proline, sarcosine, serine, threonine, tryptophan, tyrosine and valine. The stereochemistry at the asymmetric center can be of the D- or L- configuration.

The term "β-amino acid" or "beta-amino acid" refers to an amino acid wherein the amino group is β to the carboxylic acid functionality. Examples of β-amino acids include β-alanine, β-phenylalanine and the like. The term "dipeptide" as used herein refers to $AA_1$–$AA_2$ wherein $AA_1$ and $AA_2$ are independently selected from α- and β-amino acids as described above coupled together by an amide bond (—C(O)—NH—) between the carboxy terminus of AA1 and the amino terminus of $AA_2$. Examples of dipeptides include H-Glycyl-Alanine-OH, H-Glycyl-β-Alanine-OH, H-Leucyl-Glycine-OH and the like.

The term "tripeptide" as used herein refers to $AA_1$–$AA_2$–$AA_3$ wherein $AA_1$, $AA_2$ and $AA_3$ are independently selected from α- and β-amino acids as described above coupled together by amide bonds (—C(O)—NH—) between the carboxy terminus of $AA_1$ and the amino terminus of $AA_2$ and the carboxy terminus of $AA_2$ and the amino terminus of $AA_3$. Examples of tripeptides include H-Glycyl-Alanyl-Leucine-OH, H-Glycyl-β-Alanyl-Sarcosine-OH, H-Leucyl-Glycyl-Alanine-OH and the like.

The term "tetrapeptide" as used herein refers to $AA_1$–$AA_2$–$AA_3$–$AA_4$ wherein $AA_1$, $AA_2$, $AA_3$ and $AA_4$ are independently selected from α- and β-amino acids as described above coupled together by amide bonds (—C(O)—NH—) between the carboxy terminus of $AA_1$ and the amino terminus of $AA_2$, the carboxy terminus of $AA_2$ and the amino terminus of $AA_3$, and the carboxy terminus of $AA_3$ and the amino terminus of $AA_4$.

The term "carboxy protecting group" as used herein refers to a carboxylic acid protecting ester group employed to block or protect the carboxylic acid functionality while the reactions involving other functional sites of the compound are carried out. Carboxy-protecting groups are disclosed in Greene, "Protective Groups in Organic Synthesis" pp. 152–186 (1981), which is hereby incorporated herein by reference. In addition, a carboxy-protecting group can be used as a prodrug whereby the carboxy-protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy-protecting groups are $C_1$ to $C_8$ loweralkyl (e.g., methyl, ethyl or tertiary butyl and the like); benzyl and substituted derivatives thereof such as alkoxybenzyl or nitrobenzyl groups and the like; dialkylaminoalkyl (e.g., dimethylaminoethyl and the like); alkanoyloxyalkyl groups such as pivaloyloxymethyl or propionyloxymethyl and the like; aroyloxyalkyl, such as benzoyloxyethyl and the like; alkoxycarbonylalkyl, such as methoxycarbonylmethyl, cyclohexyloxycarbonylmethyl and the like; alkoxycarbonyloxyalkyl, such as t-butyloxycarbonyloxymethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl and the like; (5-(loweralkyl)-2-oxo-1,3-dioxolen-4-yl)alkyl, such as (5-t-butyl-2-oxo-1,3-dioxolen-4-yl) methyl and the like; and (5-phenyl-2-oxo-1,3-dioxolen-4-yl)alkyl, such as (5-phenyl-2-oxo-1,3-dioxolen-4-yl)methyl and the like.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "loweralkyl" as used herein refers to branched or straight chain alkyl groups comprising from one to ten carbon atoms, including methyl, ethyl, propyl, isopropyl, n-butyl, t-butyl, neopentyl and the like.

The term "alkanoyl" as used herein refers to $R_{11}C(O)$— wherein $R_{11}$ is a loweralkyl group.

The term "alkoxy" as used herein refers to RO— wherein R is loweralkyl as defined above. Representative examples of lower alkoxy groups include methoxy, ethoxy, t-butoxy and the like.

The term "alkoxyalkyl" as used herein refers to RO— wherein R is loweralkyl appended to an alkylene group. Examples of alkoxyalkyl include methoxymethyl, ethoxymethyl, 2-methoxyethyl and the like.

The term "alkoxycarbonylalkyl" as used herein refers to RO—C(O)— wherein R is loweralkyl, which is linked to the parent molcular moiety through an alkylene group. Examples of alkoxycarbonylalkyl include $CH_3O$—C(O)—$CH_2$—, $CH_3CH_2O$—C(O)—$CH_2$—, $CH_3O$—C(O)—$CH_2CH_2$—, and the like.

The term "alkenyl" as used herein refers to a branched or straight chain comprising three to twenty carbon atoms which also comprises from one to four (preferably, one or two) carbon-carbon double bonds. Representative alkenyl groups include 2-propenyl (i.e., allyl), 3-methyl-2-butenyl, 3,7-dimethyl-2,6-octadienyl, 4,8-dimethyl-3,7-nonadienyl, 3,7,11-trimethyl-2,6, 10-dodecatrienyl and the like.

The term "alkenylene" denotes a divalent group derived from a straight or branched chain hydrocarbon containing from 2 to 10 carbon atoms and also containing at least one carbon-carbon double bond. Examples of alkenylene include —CH=CH—, —$CH_2$CH=CH—, —C($CH_3$)=CH—, —$CH_2$CH=CH$CH_2$—, and the like.

The term "alkylene" denotes a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like.

The term "alkynyl" as used herein refers to a branched or straight chain comprising three to twenty carbon atoms which also comprises from one to four (preferably, one or two) carbon-carbon triple bonds. Representative alkynyl groups include 2-propynyl (propargyl), 1-propynyl and the like.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, cycloalkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. Substituted aryl also includes compounds of the formula

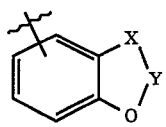

wherein X is —$CH_2$— or —O— and Y is —C(O)— or [—C(R")$_2$—]$_v$, wherein R" is hydrogen or $C_1$–$C_4$-alkyl and v is 1, 2 or 3 such as 1,3-benzodioxolyl, 1,4-benzodioxanyl and the like. In addition, substituted aryl groups include tetrafluorophenyl and pentafluorophenyl.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like.

The term "arylalkyl substituted arylalkyl" as used herein refers to an arylalkyl radical appended to an independently selected arylalkyl group. Representative arylalkyl substituted arylalkyl groups include, 4-(benzyl)benzyl, 3-(benzyl)benzyl and the like.

The term "arylalkylaryl" as used herein refers to an arylaklyl group as previously defined appended to an aryl group. Representative arylalkylaryl groups include 4-benzylphenyl, 3-benzylphenyl, 4-phenethylphenyl and the like.

The term "arylaryl" as used herein refers to an aryl group as previously defined which is appended to an aryl group. Representative arylaryl groups include biphenyl, 4-(1-naphthyl)phenyl, 4-(2-naphthyl)phenyl and the like.

The term "arylalkoxy" as used herein refers to a lower alkoxy radical to which is appended an aryl group. Representative arylalkoxy group include benzyloxy, phenylethoxy and the like.

The term "aryloxy" as used herein refers to $R_{20}$— wherein $R_{20}$ is an aryl group. Representative aryloxy groups include phenoxy, 1-naphthyloxy, 2-naphthyloxy and the like.

The term "aryloxyalkyl" as used herein refers to an alkyl radical to which is appended an aryloxy group. Representative aryloxyalkyl groups include phenoxymethyl, 2-phenoxyethyl and the like.

The term "aryloxyaryl" as used herein refers to an aryl radical to which is appended an aryloxy group. Representative aryloxyaryl groups include 4-phenoxyphenyl, 3-phenoxyphenyl, 4-phenoxy-1-naphthyl, 3-phenoxy-1-naphthyl and the like.

The term "aryloxyarylalkyl" as used herein refers to an arylalkyl radical to which is appended an aryloxy group. Representative aryloxyarylalkyl groups include 4-phenoxyphenylmethyl, 3-phenoxyphenylmethyl, 4-phenoxyphenylethyl, 3-phenoxyphenylethyl and the like.

The term "arylalkoxyaryl" as used herein refers to an aryl radical to which is appended an arylalkoxy group. Representative arylalkoxyaryl groups include 4-benzyloxyphenyl, 3-benzyloxyphenyl and the like.

The term "arylalkoxyarylalkyl" as used herein refers to an arylalkyl radical to which is appended an arylalkoxy group. Representative arylalkoxyarylalkyl groups include 4-benzyloxybenzyl, 3-benzyloxybenzyl and the like.

The term "carboxyalkyl" as used herein refers to the group —C(O)$_2$H appended to an alkyl radical. Examples of carboxyalkyl include carboxymethyl, 2-carboxyethyl and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl)ethyl and the like.

The term "1,2,3,4-cyclobutanetetracarboxylic dianhydride" as used herein refers to the (1,2/3,4) compound wherein the two anhydride rings are trans (i.e., on opposite sides of the plane formed by the cyclobutane ring) to one another. The relative stereochemistry is as

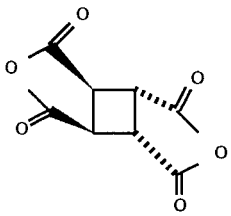

shown.

The term "halogen" or "halo" as used herein refers to I, Br, Cl or F.

The term "haloalkyl" as used herein refers to a lower alkyl radical, as defined above, bearing at least one halogen substituent, for example, chloromethyl, fluoroethyl or trifluoromethyl and the like.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; or two sulfur atoms in non-adjacent positions. The 5-membered ring has 0-2 double bonds and the 6- and 7-membered rings have 0-3 double bonds. The nitrogen heteroatoms can be optionally quaternized. The term "heterocyclic" also includes bicyclic or tricyclic groups in which any of the above heterocyclic rings is fused to one or two rings independently selected from a benzene ring, a cyclohexane ring and another heterocyclic ring independently defined as above (for example, indolyl, quinolyl, isoquinolyl, tetrahydroquinolyl, benzofuryl or benzothienyl and the like). Heterocyclics include: azetidinyl, oxetanyl, pyrrolyl, pyrrolinyl, pyrrolidinyl, pyrazolyl, pyrazolinyl, pyrazolidinyl, imidazolyl, imidazolinyl, imidazolidinyl, pyridyl, tetrahydropyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, isoxazolyl, oxadiazolyl, thiadiazolyl, pyrrolyl, pyrimidyl and benzothienyl. Heterocyclics also include compounds of the formula

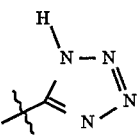

where X* is —CH₂— or —O— and Y* is —C(O)— or [—C(R")₂—]ᵥ where R" is hydrogen or C₁-C₄-alkyl and v is 1, 2 or 3 such as 1,3-benzodioxolyl, 1,4-benzodioxanyl and the like.

Heterocyclics can be unsubstituted or monosubstituted or disubstituted with substituents independently selected from hydroxy, halo, oxo (=O), alkylimino (R*N= wherein R* is a loweralkyl group), amino, alkylamino, dialkylamino, alkoxy, alkoxyalkoxy, haloalkyl, cycloalkyl, aryl, arylalkyl, aryloxyaryl, —COOH, —SO₃H and loweralkyl. In addition, nitrogen containing heterocycles can be N-protected.

The term "(heterocyclic)alkyl" as used herein refers to a heterocyclic group as defined above appended to a loweralkyl radical as defined above. Examples of heterocyclic alkyl include 2-pyridylmethyl, 4-pyridylmethyl, 4-quinolinylmethyl and the like.

The term "hydroxyalkyl" as used herein refers to an HO— group appended to an alkylene moiety. Examples of hydroxyalkyl include hydroxymethyl, 2-hydroxyethyl and the like.

The term "tetrazolyl" or "5-tetrazolyl" as used herein refers to a radical of the formula

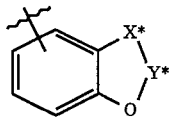

or a tautomer thereof.

The term "thioalkoxyalkyl" refers to the group R₂₁S— wherein R₂₁ is loweralkyl appended to an alkylene group. Examples of thioalkoxyalkyl include thiomethoxymethyl, thioethoxymethyl, 2-thiomethoxyethyl and the like.

The term "aryl substituted thioalkoxyalkyl" as used herein refers to a thioalkoxyalkyl group to which is appended an aryl substituent. Examples of aryl substituted thioalkoxyalkyl include benzylthiomethyl, 2-benzylthioethyl and the like.

Representative compounds of the invention include:
(1α,2β,3β,4α)-1,3-Di(N-methyl-N-(4-phenoxybenzyl) aminocarbonyl)cyclobutane-2,4-dicarboxylic acid;
(1α,2β,3β,4α)-1,3-Di(N-methyl-N-(4-benzyloxybenzyl) aminocarbonyl)cyclobutane-2,4-dicarboxylic acid;
(1α,2β,3β,4α)-1,3-Di(N-benzyl-N-(4-phenoxybenzyl) aminocarbonyl)cyclobutane-2,4-dicarboxylic acid;
(1α,2β,3β,4α)-1,3-Di(N-ethyl-N-(4-phenoxybenzyl) aminocarbonyl)cyclobutane-2,4-dicarboxylic acid;
(1α,2β,3β,4α)-1,3-Di(N-propyl-N-(4-phenoxybenzyl) aminocarbonyl)cyclobutane-2,4-dicarboxylic acid;
(1α,2β,3β,4α)-1,3-Di(N-methyl-N-(3-phenoxybenzyl) aminocarbonyl)cyclobutane-2,4-dicarboxylic acid;
(1α,2β,3β,4α)-1,3-Di(N,N-di(4-phenoxybenzyl) aminocarbonyl)cyclobutane-2,4-dicarboxylic acid;
(1α,2β,3β,4α)-1,3-Di(N-methyl-N-(4-(4-fluorophenoxy) benzyl)aminocarbonyl)cyclobutane-2,4-dicarboxylic acid;
(1α,2β,3β,4α)-1,3-Di(N-methyl-N-(3-(4-fluorophenoxy) benzylaminocarbonyl)cyclobutane-2,4-dicarboxylic acid;
(1α,2β,3β,4α)-1,3-Di(N-methyl-N-biphenylaminocarbonyl)cyclobutane-2,4-dicarboxylic acid;
(1α,2β,3β,4α)-1,3-Di(N-isopropyl-N-biphenylaminocarbonyl)cyclobutane-2,4-dicarboxylic acid;
(1α,2β,3β,4α)-1,3-Di(N-isobutyl-N-(4-phenoxybenzyl) aminocarbonyl)cyclobutane-2,4-dicarboxylic acid;
(1α,2β,3β,4α)-1,3-Di(N-propyl-N-(4-(benzyl)benzyl) aminocarbonyl)cyclobutane-2,4-dicarboxylic acid;

(1α,2β,3β,4α)-1,3-Di(N-butyl-N-(4-phenoxybenzyl)aminocarbonyl)cyclobutane-2,4-dicarboxylic acid;

(1α,2β,3β,4α)-1,3-Di(N-propargyl-N-(4-phenoxybenzyl)aminocarbonyl)cyclobutane-2,4-dicarboxylic acid;

(1α,2β,3β,4α)-1,3-Di(N-pentyl-N-(4-phenoxybenzyl)aminocarbonyl)cyclobutane-2,4-dicarboxylic acid;

(1α,2β,3β,4α)-1,3-Di(N-allyl-N-(4-phenoxybenzyl)aminocarbonyl)cyclobutane-2,4-dicarboxylic acid;

(1α,2β,3β,4α)-1,3-Di[N-cyclopropyl-N-(4-phenoxybenzyl)aminocarbonyl]cyclobutane-2,4-dicarboxylic acid;

(1α,2β,3β,4α)-1,3-Di[N-methyl-N-(4,8-dimethyl-3,7-nonadienyl)aminocarbonyl]cyclobutane-2,4-dicarboxylic acid;

(1α,2β,3β,4α)-1,3-Di[N,N-dibenzylaminocarbonyl]cyclobutane-2,4-dicarboxylic acid;

(1α,2β,3β,4α)-1,3-Di[N-(4-chlorobenzyl)aminocarbonyl]cyclobutane-2,4-dicarboxylic acid (1α,2β,3β,4α)-1,3-Di[N-methyl-N-(4-phenoxybenzyl)aminocarbonyl]cyclobutane-2,4-dicarboxylic acid dimethyl ester;

(1α,2β,3β,4α)-1,3-Di[4-phenoxybenzyloxycarbonyl]cyclobutane-2,4-dicarboxylic acid;

(1α,2β,3β,4α)-1,3-Di[N-propyl-N-(4-cyclohexyloxybenzyl)aminocarbonyl]cyclobutane-2,4-dicarboxylic acid;

(1α,2β,3β,4α)-1,3-Di[N-propyl-N-(5-phenylpentyl)aminocarbonyl]cyclobutane-2,4-dicarboxylic acid;

(1α,2β,3β,4α)-1,3-Di[N-propyl-N-(4-phenoxybutyl)aminocarbonyl]cyclobutane-2,4-dicarboxylic acid;

(1α,2β,3β,4α)-1-[N-Propyl-N-(4-phenoxybenzyl)aminocarbonyl]-3θ[N-benzyl-N-(4-phenoxybenzyl)aminocarbonyl]cyclobutane-2,4-dicarboxylic acid;

(1α,2β,3β,4α)-1-[N-Propyl-N-(4-phenoxybenzyl)aminocarbonyl]-3-[N-methyl-N-(homogeranyl)aminocarbonyl]cyclobutane-2,4-dicarboxylic acid;

(1α,2β,3β,4α)-1,3-Di[N-methoxycarbonylmethyl-N-(4-phenoxybenzyl)aminocarbonyl]cyclobutane-2,4-dicarboxylic acid;

(1α,2β,3β,4α)-1,3-Di[N-carboxymethyl-N-(4-phenoxybenzyl)aminocarbonyl]cyclobutane-2,4-dicarboxylic acid;

(1α,2β,3β,4α)-1,3-Di[N-(2-carboxyethyl)-N-(4-phenoxybenzyl(aminocarbonyl]cyclobutane-2,4-dicarboxylic acid;

(1α,2β,3β,4α)-1,3-Di[N-propyl-N-(4-phenoxybenzyl(aminocarbonyl]-2-(methoxycarbonyl)cyclobutane-4-carboxylic acid;

(1α,2β,3β,4α)-1,3-Di[N-propyl-N-(4-phenoxybenzyl)aminocarbonyl]-2-(methoxycarbonyl)cyclobutane-4-carboxylic acid;

(1α,2β,3β,4α)-1,3-Di[N-propyl-N-(4-phenoxybenzyl)aminocarbonyl]cyclobutane-2,4-dicarboxylic acid;

(1α,2β,3β,4α)-1,3-Di[N-propyl-N-(4-(3,4-methylenedioxyphenoxy)benzyl)aminocarbonyl]cyclobutane-2,4-dicarboxylic acid;

(1α,2β,3β,4α)-1,3-Di[6-methoxy-1,2,3,4-tetrahydroisoquinolinylcarbonyl]cyclobutane-2,4-dicarboxylic acid;

(1α,2β,3β,4α)-1,3-Di[N-propyl-N-(4(2-methylphenoxy)benzyl)aminocarbonyl]cyclobutane-2,4-dicarboxylic acid;

(1α,2β,3β,4α)-1,3-Di[N-propyl-N-(3-phenoxybenzyl)aminocarbonyl]cyclobutane-2,4-dicarboxylic acid;

(1α,2β,3β,4α)-1,3-Di[N-propyl-N-(5-phenoxyfurfuryl)aminocarbonyl]cyclobutane-2,4-dicarboxylic acid;

(1α,2β,3β,4α)-1,3-Di[N-propyl-N-(5-phenoxythien-2-ylmethyl(aminocarbonyl]cyclobutane-2,4-dicarboxylic acid;

(1α,2β,3β,4α)-1,3-Di[N-propyl-N-(4-(furan-2-yloxybenzyl)aminocarbonyl]cyclobutane-2,4-dicarboxylic acid;

(1α,2β,3β,4α)-1,3-Di[N-propyl-N-(4-(thiazol-2-yloxybenzyl)aminocarbonyl]cyclobutane-2,4-dicarboxylic acid;

(1α,2β,3β,4α)-1,3-Di[N-propyl-N-(4-(pyrrol-1-ylmethyl)benzyl)aminocarbonyl]cyclobutane-2,4-dicarboxylic acid;

(1α,2β,3β,4α)-1,3-Di{N-propyl-N-[4-(3-methylphenoxy)benzyl]aminocarbonyl}cyclobutane-2,4-dicarboxylic acid;

(1α,2β,3β,4α)-1,3-Di{N-propyl-N-[4-(naphth-2-yloxy)benzyl]aminocarbonyl}cyclobutane-2,4-dicarboxylic acid;

(1α,2β,3β,4α)-1,3-Di{N-propyl-N-[(3-methyl-4-phenoxy)benzyl]aminocarbonyl}cyclobutane-2,4-dicarboxylic acid;

(1α,2β,3β,4α)-1,3-Di[N-propyl-N-(4-phenyl-2,3-butadien-1-yl)aminocarbonyl]cyclobutane-2,4-dicarboxylic acid;

(1α,2β,3β,4α)-1,3-Di{N-propyl-N-(4-phenylbut-2-yn-1-yl(aminocarbonyl}cyclobutane-2,4-dicarboxylic acid;

(1α,2β,3β,4α)-1,3-Di[N-propyl-N-(4-phenylaminobenzyl)aminocarbonyl]cyclobutane-2,4-dicarboxylic acid;

(1α,2β,3β,4α)-1,3-Di[N-propyl-N-(4-phenylaminobenzyl(aminocarbonyl)cyclobutane-2,4-dicarboxylic acid;

(1α,2β,3β,4α)-1,3-Di[N-propyl-N-(4-phenylthiobenzyl)aminocarbonyl]cyclobutane-2,4-dicarboxylic acid;

(1α,2β,3β,4α)-1,3-Di[N-propyl-N-(4-phenoxymethylbenzyl)aminocarbonyl]-2,4-cyclobutanedicarboxylic acid;

(1α,2β,3β,4α)-1,3-Di[N-propyl-N-(4-phenoxyphenyl)aminocarbonyl]cyclobutane-2,4-dicarboxylic acid;

(1α,2β,3β,4α)-1,3-Di[N-propyl-N-(2-(4-phenoxyphenyl)ethyl)aminocarbonyl]cyclobutane-2,4-dicarboxylic acid;

(1α,2β,3β,4α)-1,3-Di[N-(2-methoxyethyl)-N-(4-phenoxybenzyl)aminocarbonyl]cyclobutane-2,4-dicarboxylic acid;

(1α,2β,3β,4α)-1,3-Di[N-(2-methylthioethyl)-N-(4-phenoxybenzyl)aminocarbonyl]cyclobutane-2,4-dicarboxylic acid;

(1α,2β,3β,4α)-1,3-Di[N-(2-ethylthioethyl)-N-(4-phenoxybenzyl(aminocarbonyl]cyclobutane-2,4-dicarboxylic acid;

(1α,2β,3β,4α)-1,3-Di[N-(2-benzylthioethyl)-N-(4-phenoxybenzyl)aminocarbonyl]cyclobutane-2,4-dicarboxylic acid;

(1α,2β,3β,4α)-1,3-Di[N-(furan-2-ylmethyl)-N-(4-phenoxybenzyl)aminocarbonyl]cyclobutane-2,4-dicarboxylic acid;

(1α,2β,3β,4α)-1,3-Di[N-(thien-2-ylmethyl)-N-(4-phenoxybenzyl)aminocarbonyl]cyclobutane-2,4-dicarboxylic acid;

(1α,2β,3β,4α)-1,3-Di[N-(2-hydroxyethyl)-N-(4-phenoxybenzyl(aminocarbonyl]cyclobutane-2,4-dicarboxylic acid;

(1α,2β,3β,4α)-1,3-Di[N-(2-ethylthioethyl)-N-(4-phenylthiobenzyl)aminocarbonyl]cyclobutane-2,4-dicarboxylic acid;

(1α,2β,3β,4α)-1,3-Di[N-(4-phenoxybenzyl)-N-(3-methoxyphenethyl)aminocarbonyl]cyclobutane-2,4-dicarboxylic acid;

(1α,2β,3β,4α)-1,3-Di[N-(4-phenoxybenzyl)-N-(3,4-dimethoxyphenethyl)aminocarbonyl]cyclobutane-2,4-dicarboxylic acid;

(1α,2β,3β,4α)-1,3-Di[N-(4-phenoxybenzyl)-N-phenethylaminocarbonyl]cyclobutane-2,4-dicarboxylic acid;

(1α,2β,3β,4α)-1,3-Di[N-(4-phenoxybenzyl)-N-(3-phenyl-1-propyl)aminocarbonyl]cyclobutane-2,4-dicarboxylic acid;

(1α,2β,3β,4α)-1,3-Di[N-(4-phenoxybenzyl)-N-(4-phenyl-1-butyl)aminocarbonyl]cyclobutane-2,4-dicarboxylic acid;

(1α,2β,3β,4α)-1,3-Di[N-(4-phenoxybenzyl)-N-(2-methylnaphthyl)aminocarbonyl]cyclobutane-2,4-dicarboxylic acid;

(1α,2β,3β,4α)-1,3-Di[N-((2R)-2-methyl-5-phenylpentyl)-N-(n-propyl)-aminocarbonyl]cyclobutane-2,4-dicarboxylic acid;

(1α,2β,3β,4α)-1,3-Di[(3-phenylpiperidin-1-yl)carbonyl]cyclobutane-2,4-dicarboxylic acid;

(1α,2β,3β,4α)-1,3-Di[N-benzyl-N-{syn-(4-acetoxy-5-methyl)-6-phenylhexyl}aminocarbonyl]cyclobutane-2,4-dicarboxylic acid;

(1α,2β,3β,4α)-1,3-Di[N-benzyl-N-((2R)-5-phenyl-2-methylpentyl(aminocarbonyl]cyclobutane-2,4-dicarboxylic acid;

(1α,2β,3β,4α)-1,3-Di[N-benzyl-N-{(E)-(2R)-2-methyl-5-phenyl-4-pentenyl}aminocarbonyl]cyclobutane-2,4-dicarboxylic acid;

(1α,2β,3β,4)-1,3-Di[N-(S)-α-Methylbenzyl-N-(4-phenoxybenzyl)aminocarbonyl]cyclobutane-2,4-dicarboxylic acid;

Dimethyl (1α,2β,3β,4α)-1,3-Di[N-Benzyl-N-(4-phenoxybenzyl)aminocarbonyl]cyclobutane-2,4-dicarboxylate;

(1α,2β,3β,4α)-1,3-Di[(N-4-Methoxybenzyl-N-(4-phenoxybenzyl)aminocarbonyl]cyclobutane-2,4-dicarboxylic acid;

(1α,2β,3β,4α)-1,3-Di[(N-(R)-α-Methylbenzyl-N-)4-phenoxybenzyl)aminocarbonyl]cyclobutane-2,4-dicarboxylic acid;

(1α,2β,3β,4α)-1,3-Di[(N-Cyclohexylmethyl-N-(4-phenoxybenzyl)aminocarbonyl]cyclobutane-2,4-dicarboxylic acid;

(1α,2β,3β,4α)-1,3-Di[4-(4-phenoxyphenyl)-1,2,3,6-tetrahydropyridin-1-ylcarbonyl]cyclobutane-2,4-dicarboxylic acid;

(1α,2β,3β,4α)-1,3-Di[N-cyclopropylmethyl-N-(4-phenoxybenzyl)aminocarbonyl]cyclobutane-2,4-dicarboxylic acid;

(1α,2β,3β,4α)-1,3-Di[N-(4-fluorobenzyl)-N-(4-phenoxybenzyl)aminocarbonyl]cyclobutane-2,4dicarboxylic acid;

(1α,2β,3β,4α)-1,3-Di[N-(dibenzofuran-2-ylmethyl)-N-(4-phenoxybenzyl)aminocarbonyl]cyclobutane-2,4-dicarboxylic acid;

(1α,2β,3β,4α)-1,3-Di[N-((2R)-2-(1-naphthyl)eth-2-yl)-N-(4-phenoxybenzyl)aminocarbonyl]cyclobutane-2,4-dicarboxylic acid;

(1α,2β,3β,4α)-1,3-Di[N-cyclopentyl-N-(4-phenoxybenzyl)aminocarbonyl]cyclobutane-2,4-dicarboxylic acid;

(1α,2β,3β,4α)-1,3-Di[N-cyclohexyl-N-(4-phenoxybenzyl)aminocarbonyl]cyclobutane-2,4-dicarboxylic acid;

(1α,2β,3β,4α)-1,3-Di[N-cyclobutyl-N-(4-phenoxybenzyl)aminocarbonyl]cyclobutane-2,4-dicarboxylic acid;

(1α,2β,3β,4α)-1,3-Di[N-cyclobutylmethyl-N-(4-phenoxybenzyl)aminocarbonyl]cyclobutane-2,4-dicarboxylic acid;

(1α,2β,3β,4α)-1,3-Di[N-cyclopentylmethyl-N-(4-phenoxybenzyl)aminocarbonyl]cyclobutane-2,4-dicarboxylic acid;

(1α,2β,3β,4α)-1,3-Di[N-((2R)-sec-butyl)-N-(4-phenoxybenzyl)aminocarbonyl]cyclobutane-2,4-dicarboxylic acid;

(1α,2β,3β,4α)-1-[N-Benzyl-N-(4-phenoxybenzyl)aminocarbonyl]-3-[N-(thien-2-ylmethyl)-N-(4-phenoxybenzyl)aminocarbonyl]cyclobutane-2,4-dicarboxylic acid; and (1α,2β,3β,4α)-1,3-Di[N-(3,4-Dichlorobenzyl)-N-(4-phenoxybenzyl)aminocarbonyl]cyclobutane-2,4-dicarboxylic acid;

or a pharmaceutically acceptable salt thereof.

Preferred compounds are selected from the group consisting of:

(1α,2β,3β,4α)-1,3-Di[N-benzyl-N-(4-phenoxybenzyl)aminocarbonyl]cyclobutane-2,4-dicarboxylic acid;

(1α,2β,3β,4α)-1,3-Di[N-ethyl-N-(4-phenoxybenzyl)aminocarbonyl]cyclobutane-2,4-dicarboxylic acid;

(1α,2β,3β,4α)-1,,3-Di[N-methyl-N-(3-phenoxybenzyl)aminocarbonyl]cyclobutane-2,4-dicarboxylic acid;

(1α,2β,3β,4α)-1,3-Di[N-methyl-N-(3-(4-fluorophenoxy)benzyl)aminocarbonyl]cyclobutane-2,4-dicarboxylic acid;

(1α,2β,3β,4α)-1,3-Di[N-propyl-N-(4-benzylbenzyl)aminocarbonyl]cyclobutane-2,4-dicarboxylic acid;

(1α,2β,3β,4α)-1,3-Di[N-(n-butyl)-N-(4-phenoxybenzyl)aminocarbonyl]cyclobutane-2,4-dicarboxylic acid;

(1α,2β,3β,4α)-1,3-Di[N-cyclopropyl-N-(4-phenoxybenzyl)aminocarbonyl]cyclobutane-2,4-dicarboxylic acid;

(1α,2β,3β,4α)-1,3-Di[N,N-dibenzylaminocarbonyl]cyclobutane-2,4-dicarboxylic acid;

(1α,2β,3β,4α)-1,3-Di[N-propyl-N-(5-phenylpentyl)aminocarbonyl]cyclobutane-2,4-dicarboxylic acid;

(1α,2β,3β,4α)-1-[N-Propyl-N-(4-phenoxybenzyl)aminocarbonyl]-3-[N-benzyl-N-(4-phenoxybenzyl)aminocarbonyl]cyclobutane-2,4-dicarboxylic acid;

(1α,2β,3β,4α)-1,3-Di[N-carboxymethyl-N-(4-phenoxybenzyl)aminocarbonyl]cyclobutane-2,4-dicarboxylic acid;

(1α,2β,3β,4α)-1,3-Di[N-propyl-N-(4-phenoxymethylbenzyl(aminocarbonyl]-2,4-cyclobutanedicarboxylic acid;

(1α,2β,3β,4α)-1,3-Di[N-(furan-2-ylmethyl)-N-(4-phenoxybenzyl(aminocarbonyl]cyclobutane-2,4-dicarboxylic acid;

(1α,2β,3β,4α)-1,3-Di[N-(thien-2-ylmethyl)-N-(4-phenoxybenzyl)aminocarbonyl]cyclobutane-2,4-dicarboxylic acid;

(1α,2β,3β,4α)-1,3-Di[N-benzyl-N-{syn-(4-acetoxy-5-methyl)-6-phenylhexyl}aminocarbonyl]cyclobutane-2,4-dicarboxylic acid;

(1α,2β,3β,4α)-1,3-Di[N-benzyl-N-((2R)-5-phenyl-2-methylpentyl)aminocarbonyl]cyclobutane-2,4-dicarboxylic acid;

(1α,2β,3β,4α)-1,3-Di[N-benzyl-N-{(E)-(2R)-2-methyl-5-phenyl-4-pentenyl}aminocarbonyl]cyclobutane-2,4-dicarboxylic acid;

(1α,2β,3β,4α)-1,3-Di[N-(S)-α-Methylbenzyl-N-(4-phenoxybenzyl)-aminocarbonyl]cyclobutane-2,4-dicarboxylic acid;

(1α,2β,3β,4α)-1,3-Di[4-(4-phenoxyphenyl)-1,2,3,6-tetrahydropyridin-1-ylcarbonyl]cyclobutane-2,4-dicarboxylic acid; and (1α,2β,3β,4α)-1,3-Di[N-(4-fluorobenzyl)-N-(4-phenoxybenzyl)aminocarbonyl]cyclobutane-2,4-dicarboxylic acid;

or a pharmaceutically acceptable salt thereof.

In general, the compounds of the invention can be prepared by the processes illustrated in Schemes I-VIII. According to reaction Scheme I, 1,2,3,4-cyclobutanecarboxylic dianhydride (where the two anhydrides are trans to one another) in an inert solvent such as dimethylformamide is treated with an appropriately substituted secondary amine (HNR$_1$R$_2$ where R$_1$ and R$_2$ are as defined previously herein) in the presence of an aprotic base such as triethylamine to afford the 1,2- and 1,3-diamides, respectively. (The isomeric diamides are separable by column chromatography.) The dicarboxylic acid (3) can be converted into its diester 4 (R$_3$ is loweralkyl) by treatment with an alcohol such as methanol in the presence of concentrated sulfuric acid.

Alternatively Scheme II illustrates the reaction of 1,2,3,4-cyclobutanecarboxylic dianhydride (where the two anhydrides are trans to one another) with an alcohol such as methanol to give the diesters 6 and 7 following the procedure described in Angew. Chem. International Ed. 8: 208 (1969). (The isomeric diesters are separable by column chromatography.) Compound 6 is activated, for example by treatment with thionyl chloride, and then reacted with a secondary amine (HNR$_1$R$_2$ where R$_1$ and R$_2$ are as defined above) to give compound 8.

The case where the final product is a diester is shown in Scheme III. The reaction of 1,2,3,4-cyclobutanecarboxylic dianhydride (where the two anhydrides are trans to one another) with an alcohol (for example, 4-phenoxybenzyl alcohol) leads to the formation of the 1,2- and 1,3-disubstituted products (where R$_4$ is (i) aryl, (ii) arylalkyl, (iii) arylalkyl substituted arylalkyl, (iv) aryloxyarylalkyl, (v) aryloxyaryl, (vi) arylalkoxyarylalkyl, (vii) arylalkoxyaryl, (viii) arylaryl, (ix) arylalkylaryl, (x) alkenyl or (xi) alkynyl. The isomeric diesters 9 and 10 are separable by column chromatography.

Scheme IV illustrates the preparation of another stereoisomer encompassed by the present invention and also an alternative preparation of compounds such as 3. Trans cinnamic acid or an appropriately substituted cinnamic acid or ester is photolyzed, for example by the procedure of E. M. White and H. C. Dunathan, J. Amer. Chem. Soc., 78:6055-6057 (1956), to give the 1,3-diphenyl cyclobutane diacid (photodimer) 11. The diacid is coupled using standard peptide coupling conditions, for example using dicyclohexylcarbodiimide and 1-hydroxybenzotriazole or bis(2-oxo-3-oxazolidinyl)phosphinic chloride (BOPCl), with the appropriate amine to give the 1,3-diamide diphenylcyclobutane 12. Ozonolysis of the phenyl groups, for example using O$_3$ in acetic acid and the procedure of R. Crigee and H. Hover, Chem. Ber., 93:2521-2524 (1960), affords the dicarboxylic acid compound 13.

The 3 results from the opening of 1,2,3,4-cyclobutanetetracarboxylic dianhydride 1 described in Scheme I.

Another isomer is obtained by epimerization of one center of the cyclobutane ring. The mono-ester 14 (R is loweralkyl) is prepared by making the diester of compound 13 and then hydrolyzing one of the ester functionalities using a stoichiometric amount of a base such as lithium hydroxide. The mono-ester is dissolved in an inert solvent, such as THF or ether or dimethoxyethane and the like, cooled, and treated with a non-nucleophilic base (for example, with sodium hexamethyldisilazide or lithium diisopropylamine and the like). Quenching with a proton source such as acetic acid, followed by ester hydroylsis affords the isomer as the dicarboxylic acid 15.

The preparation of another isomer is shown in Scheme V. The diphenyl dicarboxylic acid 11, prepared in Scheme IV, is converted to an anhydride, for example by treatment with acetic anhydride and sodium acetate at 100° C. by the procedure of Stoemer, et al., Chem. Ber., 497 (1920) or Liebermann, Chem. Ber., 22, 124, (1884), and then the anhydride is opened, for example, using an aqueous hydroxide ion solution or alcohol) to give the compound 16. The diacid is coupled using standard peptide coupling conditions, for example using dicyclohexylcarbodiimide and 1-hydroxybenzotriazole or BOPCl, with the appropriate amine to give the 1,3-diamide diphenylcyclobutane 17. Ozonolysis of the phenyl groups, for example using O$_3$ in acetic acid and the procedure of R. Crigee and H. Hover, Chem. Ber., 93:2521-2524 (1960), affords the dicarboxylic acid compound 18.

The preparation of another isomer is shown in Scheme VI. The diphenyl dicarboxylic acid 11, prepared in Scheme IV, is heated with excess KOH to give the isomer 19. This compound is further elaborated by the procedures described in Scheme V (the diacid is coupled using standard peptide coupling conditions, for example, using dicyclohexylcarbodiimide and 1-hydroxybenzotriazole or BOPCl, with the appropriate amine to give the 1,3-diamide diphenylcyclobutane 2.0. Ozonolysis of the phenyl groups, for example using O$_3$ in acetic acid and the procedure of R. Crigee and H. Hover, Chem. Ber., 93:2521-2524 (1960)), affords the dicarboxylic acid compound The preparation of the isomer is shown in Scheme VII. The compound 16, prepared in Scheme V, is converted to the all cis isomer 22 (for example, heating under high vacuum by the procedure of Stoemer, et al., Chem. Ber., 497 (1920)). The diacid is coupled using standard peptide coupling conditions, for example using dicyclohexylcarbodiimide and 1-hydroxybenzotriazole or BOPCl, with the appropriate amine to give the 1,3-diamide diphenylcyclobutane 2. Ozonolysis of the phenyl groups, for example using O$_3$ in acetic acid and the procedure of R. Crigee and W. Funke, Chem Ber., 94:2538-2539 (1961), affords the dicarboxylic acid compound 24.

The preparation of the (1α,2β,3β,4α)-isomer 28 is shown in Scheme VIII. The 1,3 isomer 3, whose preparation is shown in Scheme I, is esterified using Fischer conditions or diazomethane or the like to give compound 25 (R is loweralkyl). The resulting diester is hydrolyzed to the monoester 2-6 with one equivalent of LiOH in THF/H20. The monoester 26 is epimerized (for example, with lithium diisopropylamide) followed by quenching with a proton source, (for example, with acetic acid) to give the (1α,2β, 3β,4α)-isomer 27. The monoester is hydrolyzed to give the dicarboxylic acid 28.
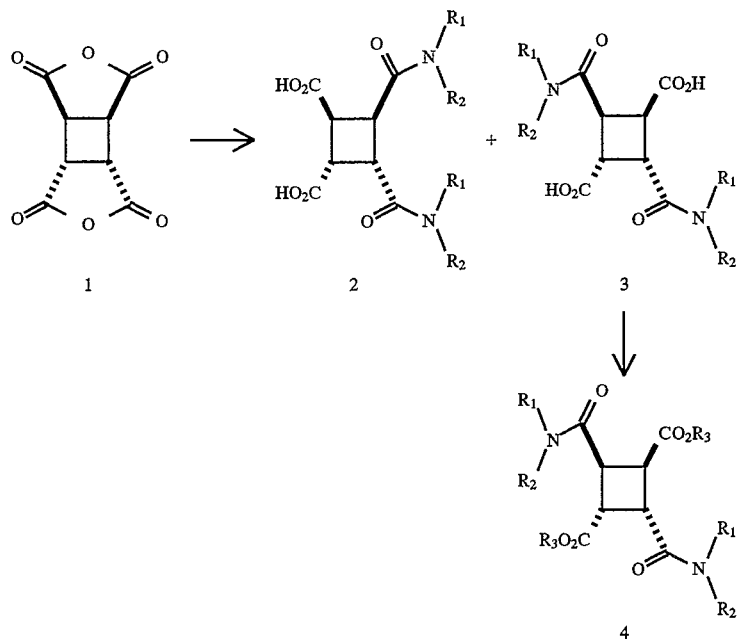
SCHEME I
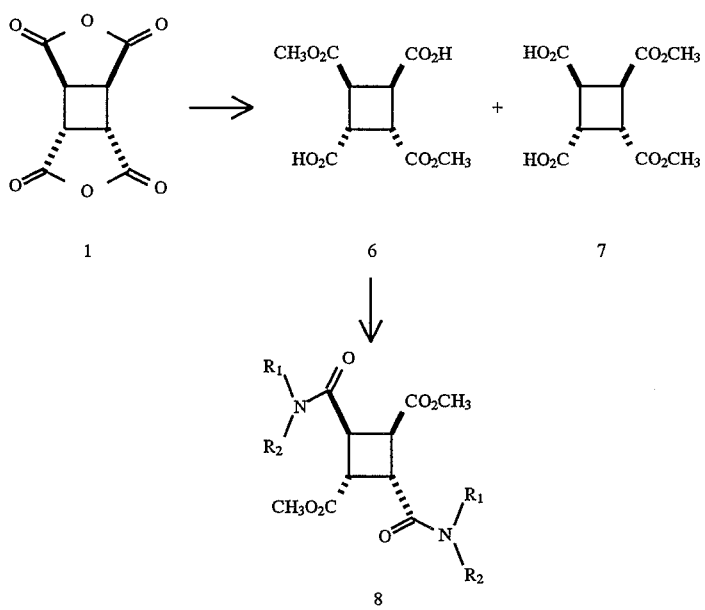
SCHEME II

SCHEME III
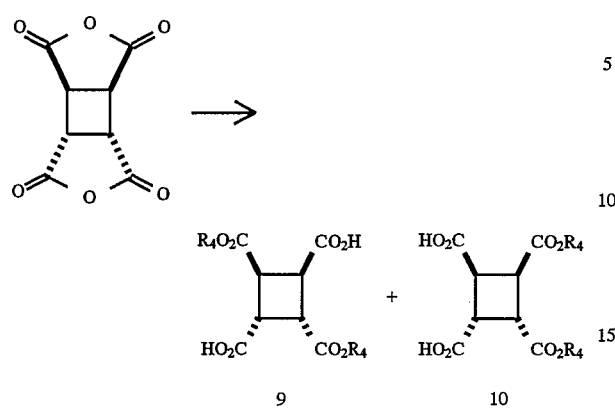
SCHEME V
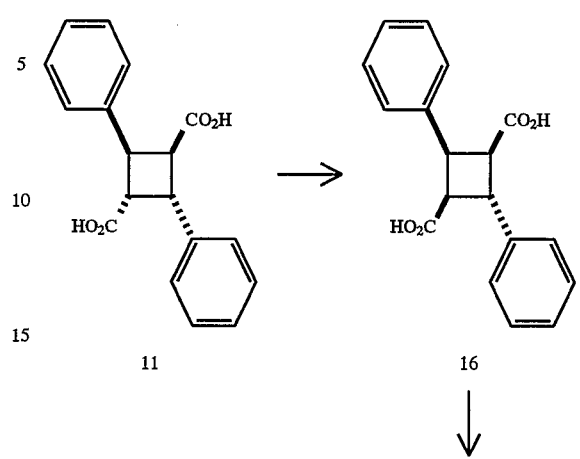
SCHEME IV
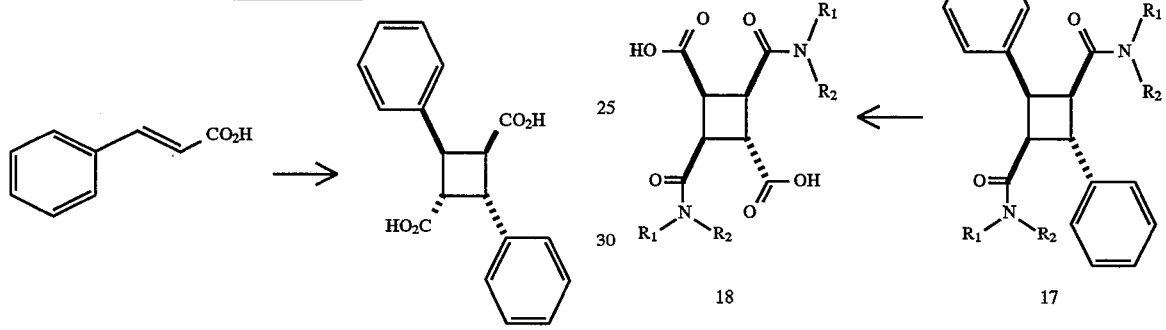
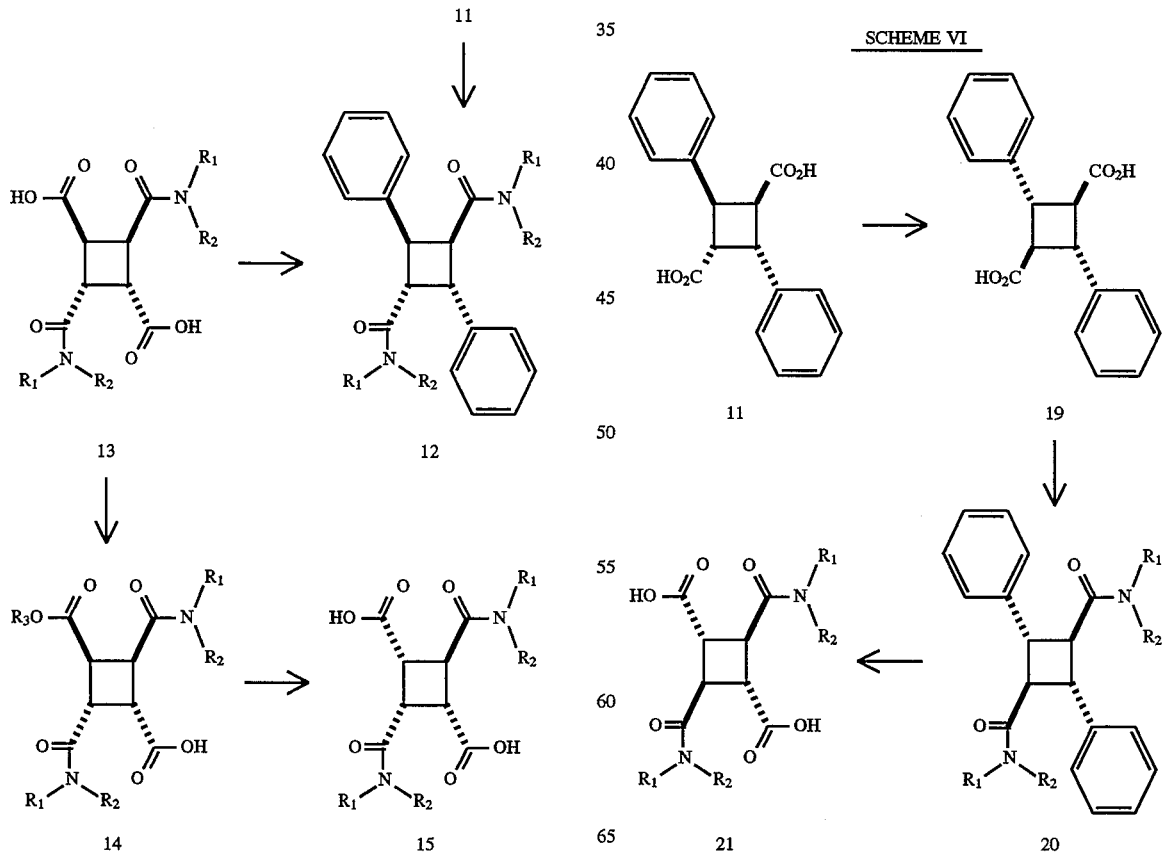
SCHEME VI

SCHEME VII

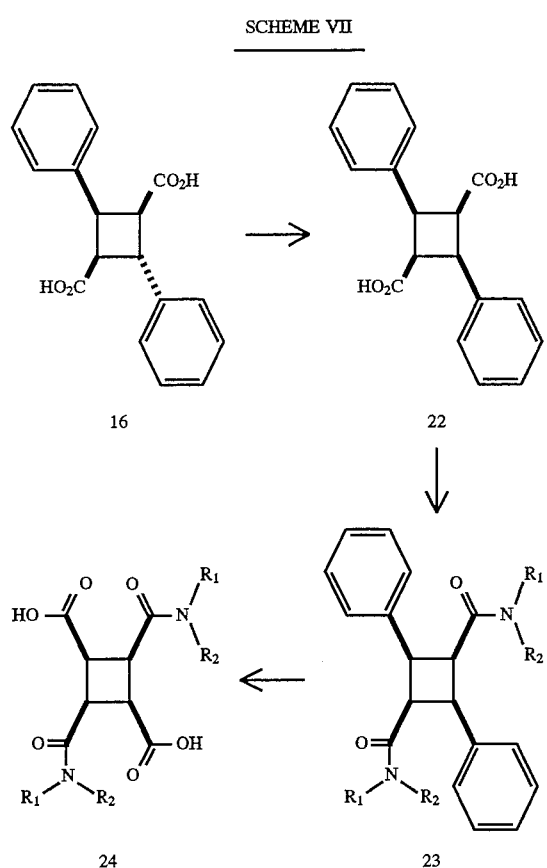

SCHEME VIII

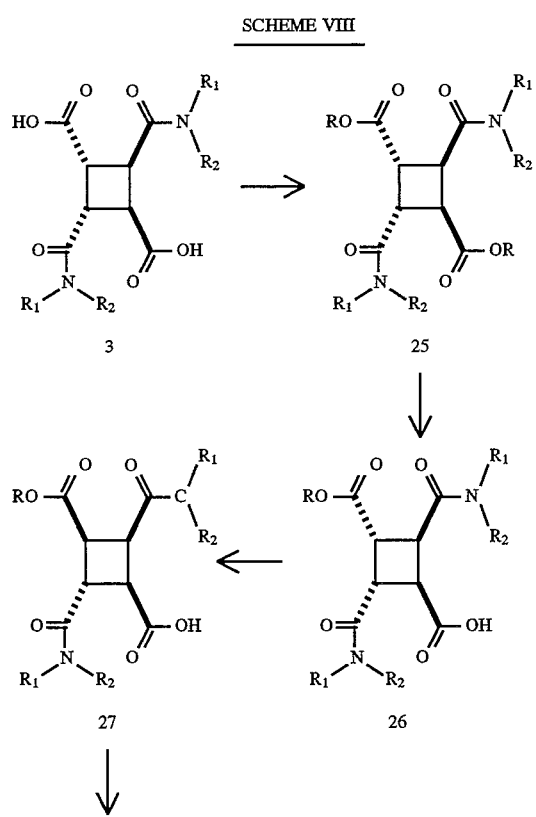

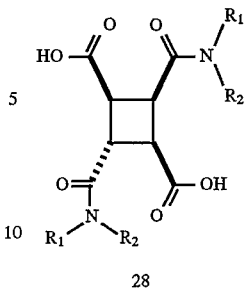

The foregoing may be better understood by reference to the following examples which are provided for illustration and not intended to limit the scope of the inventive concept. The following abbreviations are used: n-BuLi for n-butyllithium, DIBAL for diisobutylaluminun hydride, DMAP for dimethylaminopyridine, DMF for dimethylformamide, DMSO for dimethylsulfoxide, EDCl for 1-(3-dimethylaminopropyl)-3-ethylcarbodiimide hydrochloride, $Et_3N$ for triethylamine, EtOAc for ethyl acetate, EtOH for ethanol, HOAc or AcOH for acetic acid, HOBT for N-hydroxybenzotriazole hydrate, LAH for lithium aluminum hydride, MeOH for methanol, Pd/C for palladium on carbon, and THF for tetrahydrofuran.

EXAMPLE 1

N-Methyl-N-(4-phenoxybenzyl)amine

4-Phenoxybenzaldehyde (10.0 g, 0.05 mol), excess methylamine and 1.5 g of 10% Pd/C in 200 mL of methanol were stirred under an atmosphere of hydrogen for 16 hours. After removal of the catalyst by filtration through Celite®, the filtrate was concentrated under reduced pressure to give the crude product as an oil. Chromatography on silica gel eluting with ethyl acetate gave the title compound in 80% yield.

EXAMPLE 1B

N-i-Butyl-N-(4-phenoxybenzyl)amine

4-Phenoxybenzaldehyde (10.0 g, 0.05 mmol), excess isobutylamine and 1.0 g of 10% Pd/O in 200 mL of ethanol were stirred under an inert atmosphere for 16 hours followed by an atmosphere of hydrogen for 16 hours. After removal of the catalyst by filtration through Celite®, the filtrate was concentrated under reduced pressure to give the crude product as an oil. The oil was dissolved in ether and precipitated by treatment with anhydrous HCl. The solid was filtered, washed with ether, and partitioned between ethyl acetate and 1M NaOH. The ethyl acetate solution was washed with brine, dried over $Na_2SO_4$, and evaporated to give the title compound in 93% yield.

EXAMPLES 2–10

The following compounds were prepared by the procedures described in Examples 1 and 1B using the appropriate aldehydes and amines.

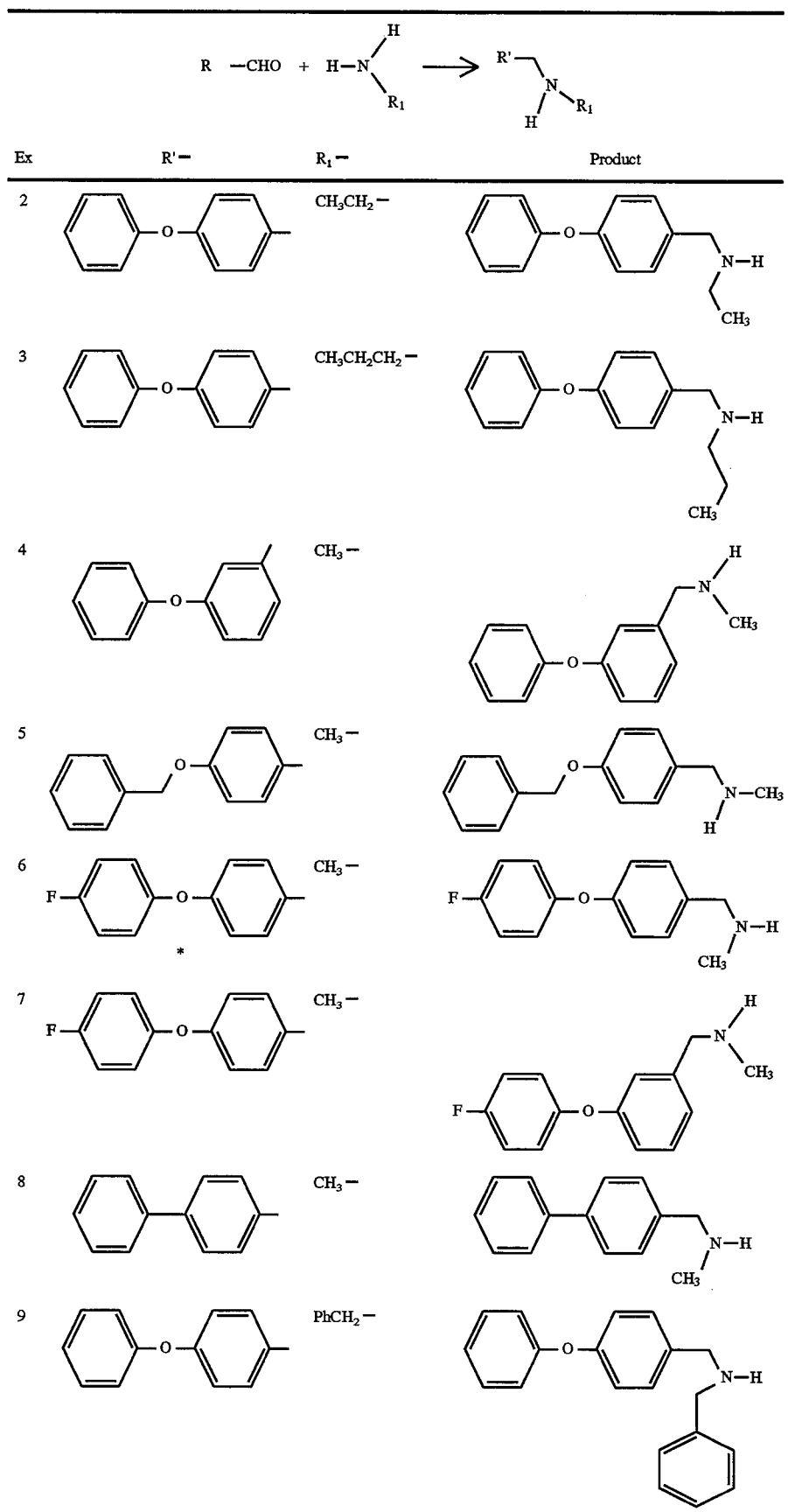

$$R-CHO + H-N\begin{matrix}H\\|\\R_1\end{matrix} \longrightarrow R'-\begin{matrix}\\\\|\\H\end{matrix}N\begin{matrix}\\\\R_1\end{matrix}$$

| Ex | R'— | $R_1$— | Product |
|---|---|---|---|
| 10 | 4-phenoxyphenyl* | Cyclopropyl | N-cyclopropyl-N-H-(4-phenoxybenzyl)amine |
| 11 | 4-benzylphenyl** | $CH_3(CH_2)_2$— | N-propyl-N-H-(4-benzylbenzyl)amine |

*The aldehyde was prepared from 4-fluorophenol and 4-bromobenzaldehyde.

**The aldehyde was prepared by the reaction of 4-benzylbenzoic acid (25.0 g, 118 mmol) dissolved in 200 mL of anhydrous THF under an atmosphere of dry $N_2$, cooled to 0° C. and treated with borane (1.0 M in THF, 200 mL, 200 mmol) added over 10 minutes. After 4 hours, saturated $NH_4Cl$ solution was added, and the mixture was concentrated under reduced pressure and partitioned between ethyl acetate and 1 M HCl. The ethyl acetate solution was washed with 1 M HCl, 5% $NaHCO_3$, and brine, dried over $MgSO_4$, and evaporated to give 21.4 g (92%) of the corresponding alcohol. The alcohol (4.75 g, 24.0 mmol) was dissolved in 250 mL of methylene chloride and treated with pyridinium chlorochromate (6.45 g, 29.9 mmol) for 18 hours. Filtration through Celite ® and silica gel chromatography (20% ethyl acetate in hexane) gave 4-benzylbenzaldehyde in 50% yield.

EXAMPLE 12

N,N-Di(4-phenoxybenzyl)amine

4-Phenoxybenzaldehyde was reacted with ammonium acetate to give the title compound.

EXAMPLE 13

N-Propargyl-N-(4-phenoxybenzyl)amine

4-Phenoxybenzaldehyde (5.0 g, 25.2 mmol) and propargylamine (1.46 g, 26.5 mmol) were dissolved in 100 mL of 1% acetic acid in methanol under an atmosphere of dry nitrogen. Sodium cyanoborohydride (1.66 g, 26.5 mmol) was added, and stirring was continued for 18 hours at which time the solvent was removed under reduced pressure. The residue was suspended in ether, washed with 5% $NaHCO_3$ and brine, and dried over $Na_2SO_4$ to give 5.6 g (93%) of the title compound.

EXAMPLE 14

(1α,2β,3β,4α)-1,3-Di[N-methyl-N-(4-phenoxybenzyl)aminocarbonyl]cyclobutane-2,4-dicarboxylic acid To a solution cooled in an ice bath of 1,2,3,4-cyclobutanetetracarboxylic dianhydride (3.42 g, 17.4 mmol) in 30 mL of dimethylformamide was added triethylamine (3.51 g, 3.47 mmol). The mixture was then treated with N-methyl-N-(4-phenoxybenzyl)amine (10 g, 4.74 mmol) in 20 mL of dimethylformamide dropwise over 20 minutes. After stirring at ambient temperature overnight, the dimethylformamide was removed under reduced pressure to give a crude solid mixture. The crude solid was taken up in ethyl acetate, washed with dilute hydrochloric acid, water and saturated sodium chloride solution, dried over sodium sulfate, filtered and concentrated in vacuo. When solid began precipitating from solution, the mixture was cooled over an ice bath for 1 hour and then filtered to give the title compound which was recrystallized from methanol to give 4.00 g (37%). m.p. 220°–222° C. $^1$H NMR (DMSO-$d_6$, 300 MHz) δ 2.86 (26, 6H), 3.63 (dd, 2H), 4.34 (d, 2H), 4.57 (d, 2H), 6.90–7.39 (m, 18H). MS m/e 623 (M+H)$^+$.

EXAMPLE 15

(1α,2β,3β,4α)-1,3-Di[N-methyl-N-(4-benzyloxybenzyl)aminocarbonyl]cyclobutane-2,4-dicarboxylic acid To a solution of 1,2,3,4-cyclobutanetetracarboxylic dianhydride (0.44 g, 2.29 mmol) and triethylamine (0.63 mL, 4.58 mmol) in dimethylformamide (20 mL) at 0° C. under nitrogen was added the compound resulting from Example 2 (1.3 g, 5.75 mmol). The reaction was stirred at 0° C. for 2 hours and then allowed to warm to ambient temperature overnight. The DMF was removed under reduced pressure, and the oily residue was partitioned between ethyl acetate and water. The organic phase was washed with 1N HCl, water and brine, dried over magnesium sulfate, filtered and evaporated under reduced pressure to give crude product. Flash silica gel chromatography eluting with 94:5:1 $CHCl_3$-MeOH-HOAc yielded 14% of the title compound. m.p. 91°–94° C. MS m/e 651 (M+H)$^+$.

EXAMPLE 16

(1α,2β,3β,4α)-1,3-Di[N-benzyl-N-(4-phenoxybenzyl)aminocarbonyl]cyclobutane-2,4-dicarboxylic acid To a solution of 1,2,3,4-cyclobutanetetracarboxylic dianhydride (0.5 g, 2.54 mmol) in THF (5 mL) was added N-benzyl-N-(4-phenoxybenzyl)amine (1.47 g, 5.08 mmol) in THF (5 mL) at 25° C. The initial slurry became homogeneous after stirring at 25° C. for 25 minutes. The solution was stirred one additional hour, then poured into 100 mL of ethyl acetate. The organic layer was washed successively with 50 mL 1N H₃PO₄, 50 mL 10% NaHCO₃ and 50 mL 10% NaCl, then dried over anhydrous sodium sulfate, filtered and solvent removed in vacuo to afford 2.2 g of a white foamy solid. The crude product containing both isomers was purified by silica gel chromatography eluting with 94:5:1 CHCl₃-MeOH-HOAc. The faster moving product was isolated in 32% yield and characterized as the title compound. $^1$H NMR (CDCl₃+CD₃OD, 500 MHz) 25 3.62–3.67 (m, 2H), 3.98–4.21 (m, 8H), 4.43–4.52 (m, 1H), 4.67–4.74 (m, 1H), 6.81–7.67 (m, 28H). MS (DCl/NH₃) m/e 775 (M+H)⁺.

EXAMPLES 17–32

The following examples were prepared using the general procedures described in Example 14.

| Ex | R₁ | R₂ | m.p. °C. |
|---|---|---|---|
| 17 | Ethyl | 4-(phenoxy)benzyl | * |
| 18 | Propyl | 4-(phenoxy)benzyl | * |
| 19 | Methyl | 3-(phenoxy)benzyl | 142–144 |
| 20 | 4-(phenoxy)benzyl | 4-(phenoxy)benzyl | 189–191 |
| 21 | Methyl | 4-(4-fluorophenoxy)benzyl | 202–205 |
| 22 | Methyl | 3-(4-fluorophenoxy)benzyl | 148–150 |
| 23 | Methyl | biphenylmethyl | 236–238 |
| 24 | i-Propyl | 4-(phenoxy)benzyl | 75–83 |
| 25 | i-Butyl | 4-(phenoxy)benzyl | * |

-continued

| | | | |
|---|---|---|---|
| 26 | n-Propyl | 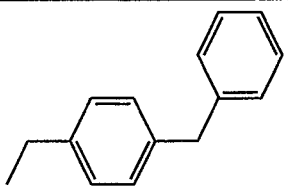 | * |
| 27 | n-Butyl | 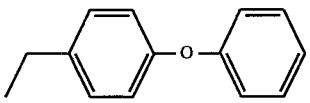 | * |
| 28 | —CH₂—C≡CH | 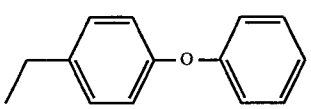 | * |
| 29 | N-Pentyl | 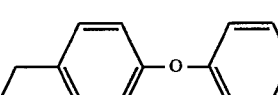 | * |
| 30 | —CH₂—CH=CH₂ | 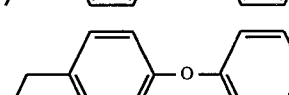 | * |
| 31 | Cyclopropyl | 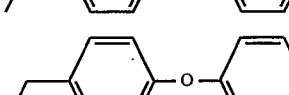 | 205–209 |
| 32 | Methyl** | 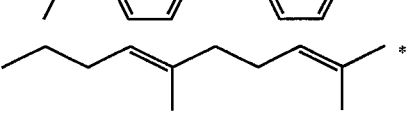 | * |

| Ex | DATA |
|---|---|
| 17 | ¹HNMR(DMSO-d₆, 300MHz)δ0.97(q, 4H), 1.10(dt, 6H), 3.58 (m, 2H), 3.95(m, 2H), 4.26(d, 2H), 4.66(dd, 1H), 4.77(d, 1H), 6.90–7.43(m, 18H), 12.40(bs, 2H) |
| 18 | ¹HNMR(DMSO-d6, 300MHz)δ0.82(m, 6H), 1.49(m, 4H), 2.90 (m, 2H), 3.58(m, 2H), 4.27(m, 2H), 4.70(m, 2H), 6.88–7.43(m, 18H) |
| 25 | ¹HNMR(CDCl₃, 500 MHz)δ0.89(m, 12H), 1.97(m, 2H), 3.08 (m, 3H), 3.32(m, 1H), 3.78(m, 2H), 4.15–4.80(m, 4H), 6.90–7.35 (m, 18H) |
| 26 | ¹HNMR(CDCl₃, 500 MHz)δ0.86(m, 6H), 1.59(m, 2H), 3.05 (m, 1H), 3.18(m, 2H), 3.54(m, 1H), 3.86(m, 2H), 3.97(m, 4H), 4.07(m, 1H), 4.20(m, 1H), 4.39(m,2H), 4.61(m, 1H), 4.82(m, 1H), 7.10–7.33(m, 18H) |
| 27 | ¹HNMR(CD₃OD), 500 MHz)δ0.92(m, 6H), 1.31(m, 4H), 1.51 (m, 2H), 1.58(m, 2H), 3.03(ddd, J=14, 7, 7Hz1H), 3.18(m, 1H), 3.41(m, 1H), 3.47(m, 1H), 3.62–3.81(m, 3H), 4.14–4.25 (m, 3H), 4.34(dd, J=15.1, 12.2Hz, 2H), 4.42(dd, J=16.9, 4.7 Hz, 1H), 4.8(m, 1H), 6.9–7.(m, 8H). 7.1(m, 2H), 7.23–7.38(m, 8H) |
| 28 | ¹HNMR(CDCl₃, 500MHz)δ2.29(m, 2H), 3.97(m, 6H), 4.25 (m, 2H), 4.41(m, 3H), 4.57(m, 1H), 4.71(m, 1H), 4.93(m, 1H), 6.92–7.36(m, 18H) |
| 29 | ¹HNMR(CDCl₃, 500MHz)δ0.86(m, 6H), 1.25(m, 8H), 1.56 (m, 4H)3.21(m, 4H), 3.47(m, 2H), 3.83(m, 2H), 4.21(m, 2H), 4.43(m, 2H), 4.59(m, 1H), 4.76(m, 1H), 6.91–7.36(m, 18H) |
| 30 | ¹HNMR(CDCl₃, 500MHz)δ3.12(m, 1H), 3.60(s, 1H), 3.72(m, H), 3.88(m, 4H), 4.21(m, 3H), 4.40(m, 2H), 4.59(m, 1H), 4.79 (m, 1H), 5.18(m, 4H), 5.75(m, 2H), 6.91–7.37(m, 18H) |
| 32 | ¹HNMR(CDCl₃, 500MHz)δ1.59(s, 6H), 1.62(s, 6H), 1.67(s, 6H), 1.92–2.12(m, 8H), 2.16–2.38(m, 4H), 2.96, 3.04(2s, 6H), 3.17–3.49(m, 4H), 3.71–3.91(m, 2H), 3.97–4.26(m, 2H), 5.00–5.17(m, 4H) |

*Amorphous solid
**N-Methyl-N-homogeranyl amine was prepared by lithioformamidine alkylation of geranyl bromide as described by Coates, et. al., J. Org. Chem., 57(12): 3444-9 (1992).

EXAMPLE 33

(1α,2β,3β,4α)-1,3-Di[N,N-dibenzylaminocarbonyl]
  cyclobutane-2,4-dicarboxylic acid To a slurry of 1,2,3,4-cyclobutanetetracarboxylic dianhydride (2.7 g, 13.8 mmol) in THF (30 mL) was added N,N-dibenzylamine (5.72 g, 28.9 mmol) in THF (10 mL). The slurry was stirred for 5 minutes at 20° C., whereupon, a homogeneous solution resulted. The resulting solution was stirred for 20 hours at 20° C., then concentrated in vacuo to a white foam. The foam was dissolved in 100 mL of ethyl acetate and washed successively with 50 mL 1N $H_3PO_4$ and 10% NaCl, then dried over anhydrous sodium sulfate, filtered and concentrated in vacuo to afford 4.4 g of a white foamy solid. The crude product (2.1 g) containing both isomers was purified by silica gel chromatography eluting with 94:5:1 $CHCl_3$-MeOH-HOAc. The faster moving product was isolated in 22% yield and characterized as the title compound. $^1H$ NMR (DMSO-$d_6$, 300 MHz) δ 3.68–3.72 (d, 2H), 3.96–4.19 (m, 6H), 4.65–4.92 (dd, 4H), 7.14–7.36 (m, 20H), 12.67 (bs, 2H). MS (FAB) m/e 591 (M+H)$^+$.

EXAMPLE 34

(1α,2β,3β,4α)-1,3-Di[N-benzyl-N-(4-chlorobenzyl)
  aminocarbonyl]cyclobutane-2,4-dicarboxylic acid To a slurry of 1,2,3,4-cyclobutanetetracarboxylic dianhydride (0.5 g, 2.5 mmol) in DMF (6 mL) was added N-4-chlorobenzyl-N-benzylamine hydrochloride (1.36 g, 5.1 mmol) in DMF (3mL) containing $Et_3N$ (0.71 mL, 5.1 mmol). The slurry was stirred for 5 minutes at 20° C., whereupon, a homogeneous solution resulted. The resulting solution was stirred 20 hours at 20° C. The solution was diluted with 100 mL of ethyl acetate and washed successively with 50 mL 1 N $H_3PO_4$ and 10% NaCl solution, then dried over anhydrous sodium sulfate, filtered and concentrated in vacuo to afford 1.1 g of a white foamy solid. The crude product containing both isomers was purified by silica gel chromatography eluting with 94:5:1 $CHCl_3$-MeOH-HC) Ac. The slower moving product was isolated in 21% yield and characterized as the title compound. $^1H$ NMR (DMSO-$d_6$, 300 MHz) δ 3.64–3.70 (m, 2H), 3.97–4.09 (m, 4H), 4.19–4.27 (m, 2H), 4.67–4.74 (m, 2H), 4.82–4.90 (m, 2H), 7.18–7.41 (m, 18H), 12.33 (bs, 2H). MS (FAB) m/e 659 (M+H)$^+$.

EXAMPLE 35

(1α,2β,3β,4α)-1,3-Di[N-methyl-N-(4-phenoxybenzyl)
  aminocarbonyl]cyclobutane-2,4-dicarboxylic acid dimethyl ester To the dicarboxylic acid resulting from Example 14 (1.00 g, 1.60 mmol) dissolved in 20 mL of anhydrous methanol was added 5 drops of concentrated sulfuric acid. The clear mixture was stirred at ambient temperature overnight. The solvents were removed under reduced pressure to give a residue which was dissolved in ethyl acetate, washed with sodium bicarbonate solution, water and saturated sodium chloride solution, dried, filtered and concentrated in vacuo. The residue obtained was chromatographed on silica gel eluting with 4:1 ethyl acetate-hexane to give the title compound in 75% yield. $^1H$ NMR (DMSO-$d_6$, 300 MHz) δ 2.85 (s, 6H), 3.47 (s, 6H), 3.78 (dd, 2H), 4.10 (dd, 2H), 4.40 (d, 2H), 4.60 (d, 2H), 6.97–7.20 (m, 18H). MS m/e 651 (M+H)$^+$.

EXAMPLE 36

(1α,2β,3β,4α)-1,3-Di[4-phenoxybenzyloxycarbonyl]
  cyclobutane-2,4-dicarboxylic acid

EXAMPLE 36A

4-Phenoxybenzyl alcohol

A 0° C. solution of 4-phenoxybenzaldehyde (5.0 g, 25.2 mmol) in 10 mL THF under an atmosphere of dry $N_2$ was treated with borane (1.0M in THF, 11.25 mL) for 1 hour. A saturated $NH_4Cl$ solution was added, and the mixture was diluted with ethyl acetate. The organic layer was washed with 1M HCl, 5% $NaHCO_3$ and brine, dried and concentrated in vacuo to give the title compound in 92% yield.

EXAMPLE 36B (1α,2β,3β,4α)-1,3-Di[4-phenoxybenzyloxycarbonyl]
  cyclobutane-2,4-dicarboxylic acid The compound resulting from Example 36A (1.0 g, 5.0 mmol) was treated with butyl lithium (1.6M in hexanes, 3.1 mL) in 100 mL THF at −78° C. for 15 minutes. A suspension of 1, 2, 3, 4-cyclobutane-tetracarboxylic dianhydride (0.49 g, 2.5 mmol) in 30 mL THF was added. The reaction was stirred at −78° C. for 1 hour then allowed to warm to ambient temperature and stand for 18 hours. Saturated $NH_4Cl$ solution was added, and the mixture was concentrated under reduced pressure to an oil. The oil was suspended in ethyl acetate, washed with 1M HCl and brine, dried over $Na_2SO_4$ and concentrated under reduced pressure. The crude product was purified by flash silica gel chromatography (94:5:1 chloroform-methanol-acetic acid) to give 54.3 mg of the title compound. m.p. 147°–151° C. $^1H$ NMR ($CDCl_3$, 300MHz) δ 3.82 (s, 4H), 5.11 (s, 4H), 6.90–7.36 (m, 18H). MS (DCl/$NH_3$) m/e 596 (M+H)$^+$.

EXAMPLE 37

(1α,2β,3β,4α)-1,3-Di[N-propyl-N-(4-cyclohexyloxybenzyl)aminocarbonyl]cyclobutane-2,4-
  dicarboxylic acid

EXAMPLE 37A 4-(Cyclohex-2-enyloxy)benzyl alcohol 4-(Cyclohex-2-enyloxy)benzoic acid (25 g, 115 mmol) was dissolved in 250 mL dry tetrahydrofuran and cooled to −10° C. under an atmosphere of dry nitrogen. N-Methylmorpholine (12.6 mL, 115 mmol) and isobutylchloroformate (15.9 mL, 115 mmol) were added. After 10 minutes at −10° C., the mixture was warmed to room temperature and filtered. The volume was reduced to 50 mL under reduced pressure before cooling to 0° C. and adding diisobutylaluminum hydride (1.5M in toluene, 160 mL) over 10 minutes. After 30 minutes, the reaction was allowed to warm to ambient temperature and stirred for 2 hours. The mixture was cooled in an ice bath, diluted with ether, quenched with methanol, and poured into cold Rochelle's salt solution. The crude product was extracted with ether, dried over $Na_2SO_4$, and concentrated in vacuo. The residue obtained was chromatographed eluting with 20% ethyl acetate in hexane to give 4.24 g (18%) of the title alcohol.

EXAMPLE 37B 4-(Cyclohex-2-eneyloxy) benzaldehyde

The alcohol resulting from Example 37A (4.24 g, 20.7 mmol) was dissolved in 250 mL of methylene chloride under an atmosphere of dry nitrogen. Pyridinium chlorochromate (5.62 g, 26.1 mmol) was added over 5 minutes. After stirring at ambient temperature 72 hours, the mixture was filtered through Celite® and concentrated in vacuo. Flash chromatography on silica gel eluting with 10% ethyl acetate in hexane afforded 3.25 g (77%) of the title compound.

EXAMPLE 37C (1α,2β,3β,4α)-1,3-Di[N-propyl-N-(4-cyclohexyloxybenzyl)aminocarbonyl]cyclobutane-2,4-dicarboxylic acid The compound resulting from Example 37B was reacted with excess n-propylamine under the catalytic hydrogenation conditions described in Example 1 to give N-propyl-N-(4-cyclohexylbenzyl)amine. This amine was reacted with 1,2,3,4-cyclobutanetetracarboxylic dianhydride by the procedures described in Example 14 to give the title compound. $^1$H NMR (CDCl$_3$, 500MHz) δ 0.85 (m, 6H), 1.35 (m, 6H), 1.55 (m, 10H), 1.80 (m, 4H), 1.97 (m, 4H), 3.15 (m, 4H), 3.46 (m, 2H), 3.86 (m, 2H), 4.2 (m, 2H), 4.4 (m, 2H), 4.57 (m, 1H), 4.69 (m, 1H) 6.94 (m, 4H), 7.13 (m, 4H). MS m/e 691 (M+H)$^+$.

EXAMPLE 38

(1α,2β,3β,4α)-1,3-Di[N-propyl-N-(5-phenylpentyl)aminocarbonyl]cyclobutane-2,4-dicarboxylic acid

EXAMPLE 38A

5-Phenylpentanal

To a solution of 5-phenylpentanol (15.0 g, 91 mmol) in methylene chloride was added pyridinium chlorochromate (24.6 g, 114 mmol) under an atmosphere of dry nitrogen at room temperature. After 18 hours, the mixture was filtered through a bed of Celite®, and purified by flash chromatography on silica gel eluting with 10% ethyl acetate in hexane to give the aldehyde in 57% yield.

EXAMPLE 88B (1α,2β,3β,4α)-1,3-Di[N-propyl-N-(5-phenylpentyl)aminocarbonyl]cyclobutane-2,4-dicarboxylic acid The title compound was prepared by the procedures described in Example 37C using the compound resulting from Example 38A to prepare the amine. $^1$H NMR (CDCl$_3$, 500MHz) δ 0.88 (m, 6H), 1.31 (m, 4H), 1.6 (m, 12H), 2.60 (m, 4H), 3.1 (m, 6H), 3.43 (m, 2H), 3.79 (m, 2H), 4.08 (m, 2H), 7.18 (m, 4H), 7.26 (m, 6H). MS m/e 607 (M+H)$^+$.

EXAMPLE 39

(1α,2β,3β,4α)-1,3-Di[N-propyl-N-(4-phenoxybutyl)aminocarbonyl]cyclobutane-2,4-dicarboxylic acid

EXAMPLE 39A

N-Propylbenzamide

Benzoyl chloride (10 mL, 86.2 mmol) in ethyl acetate (200 mL) was treated with propylamine. The precipitate was removed by filtration, and the solution was washed with 1M HCl, 5% NaHCO$_3$, and brine, dried over MgSO$_4$ and concentrated in vacuo to give the title compound in 96% yield.

EXAMPLE 39B

N-Propyl-N-(4-phenoxybutyl)benzamide

To a solution of the compound resulting from Example 39A (5.0 g, 31 mmol) in DMF (150 mL) at 0° C., was added sodium bis(trimethylsilyl)amide (1.0M in THF, 31 mL). After 30 minutes, 4-phenoxybutyl bromide (7.02 g, 31 mmol) was added. The reaction was allowed to warm to ambient temperature and stirred for 48 hours at which time the solution was concentrated/n vacuo and partitioned between ethyl acetate and 1M HCl. The organic phase was washed with 1M HCl, 1M NaOH, and brine, dried over anhydrous MgSO$_4$ and concentrated in vacuo to afford 7.14 g of the title compound.

EXAMPLE 39C

N-Propyl-N-(4-phenoxybutyl)amine

A mixture of the compound resulting from Example 39B (7.14 g, 22.9 mmol), ethanol (150 mL), and NaOH (3M, 50 mL) was refluxed 72 hours. The mixture was concentrated/n vacuo, diluted with ethyl acetate, washed with 1M NaOH, and extracted with 1M HCl. The acidic extract was neutralized with NaOH and extracted with ethyl acetate. The combined organic extracts were dried over Na$_2$SO$_4$ and concentrated in vacuo to give 0.64 g of the title compound.

EXAMPLE 39D (1α,2β,3β,4α)-1,3-Di[N-propyl-N-(4-phenoxybutyl)aminocarbonyl]cyclobutane-2,4-dicarboxylic acid The compound resulting from Example 39C was reacted with 1,2,3,4-cyclobutanetetracarboxylic dianhydride by the procedures described in Example 14 to give the title compound. $^1$H NMR (CDCl$_3$, 500MHz) δ 0.85 (m, 6H), 1.7 (m, 12H), 3.18 (m, 4H), 3.4 (m, 4H), 3.66–4.15 (m, 8H), 6.93 (m, 4H), 7.26 (m, 4H), 7.45 (m, 2H). MS m/e 611 (M+H)$^+$.

EXAMPLE 40

(1α,2β,3β,4α)-1-[N-Propyl-N-(4-phenoxybenzyl)aminocarbonyl]-3-[N-benzyl-N-(4-phenoxybenzyl)aminocarbonyl]cyclobutane-2,4-dicarboxylic acid

EXAMPLE 40A (1α,2β,3β,4α)-1-[N-Propyl-N-(4-phenoxybenzyl)aminocarbonyl]cyclobutane-2,3,4-tricarboxylic acid To a solution of 1,2,3,4-cyclobutanetetracarboxylic dianhydride (1.0 g, 5.1 mmol) and triethylamine (0.7 mL, 5.1 mmol) in acetonitrile (50 mL) under an atmosphere of dry nitrogen was added N-propyl-4-phenoxybenzyl amine hydrochloride. After stirring 18 hours, 1M HCl was added and stirring was continued for 18 hours. The mixture was diluted with ethyl acetate, washed with 1M HCl followed by brine, dried over Na$_2$SO$_4$ and concentrated in vacuo to give 2.3 g crude product.

A solution of the crude triacid (1.1 g, 2.4 mmol) in methanol (25 mL) was treated with an excess of ethereal diazomethane. Evaporation and flash silica gel chromatography, eluting with 50% ethyl acetate in hexane, afforded the corresponding pure triester (0.8 g, 67%). The pure triester was dissolved in methanol (10 mL) and treated with 3M NaOH (5 mL) at 40° C. for 48 hours. The reaction mixture was diluted with water and washed aqueous with ethyl acetate. The aqueous solution was acidified to pH 2 with concentrated HCl. The product was extracted into ethyl acetate which was then washed with brine, dried over Na$_2$SO$_4$ and concentrated in vacuo to give 0.73 g (99%) of the pure triacid.

EXAMPLE 40B (1α,2β,3β,4α)-1-[N-Propyl-N-(4-phenoxybenzyl)aminocarbonyl]-3-[N-benzyl-N-(4-phenoxybenzyl)aminocarbonyl]cyclobutane-2,4-dicarboxylic acid To a solution of the compound resulting from Example 40A (25 mg, 0.06 mmol) in dimethylformamide (0.5 mL) and methylene chloride (5 mL) at 0° C., was added dicyclohexylcarbodiimide (11 mg, 0.06 mmol). After 1 hour, N-benzyl-4-phenoxybenzyl amine (16 mg, 0.06 mmol) and triethylamine (0.02 mL, 0.16 mmol) were added. The reaction was allowed to warm to ambient temperature and stirred for 18 hours. Ethyl acetate was added to the reaction mixture which was then washed with 1M HCl and brine, dried over Na$_2$SO$_4$, and concentrated in vacuo. The residue obtained was purified by flash silica gel chromatography eluting with 94:5:1 chloroform-methanol-acetic acid to give 14 mg (35%) of the title compound. $^1$H NMR (CDCl$_3$, 300MHz) δ 0.88 (m, 3H), 1.35 (m, 2H), 3.62–4.61 (m, 12H), 6.89–7.35 (m, 23H). MS m/e 727 (M+H)$^+$.

EXAMPLE 41

(1α,2β,3β,4α)-1-[N-Propyl-N-(4-phenoxybenzyl) aminocarbonyl]-3-[N-methyl-N-(homogeranyl) aminocarbonyl]cyclobutane-2,4-dicarboxylic acid The title compound was prepared by the procedures described in Example 40. $^1$H NMR (CDCl$_3$, 300MHz) δ 0.85 (m, 3H), 1.61 (m, 6H), 1.68 (m, 3H), 2.00 (m, 8H), 2.92 (m, 5H), 3.66 (m, 2H), 4.03 (m, 3H), 4.55 (m, 3H), 5.05 (m, 2H), 6.85–7.35 (m, 9H). MS m/e 619 (M+H)$^+$.

EXAMPLE 42

(1α,2β,3β,4α)-1,3-Di[N-methoxycarbonylmethyl-N-(4-phenoxybenzyl)aminocarbonyl]cyclobutane-2,4-dicarboxylic acid The title compound was prepared by the procedures described in Example 14. 1H NMR (CDCl$_3$, 500MHz) δ 3.62–3.79 (m, 6H), 3.94–5.14 (m, 12H), 6.91–7.51 (m, 18H). MS m/e 739 (M+H)$^+$.

EXAMPLE 43

(1α,2β,3β,4α)-1,3-Di[N-carboxymethyl-N-(4-phenoxybenzyl)aminocarbonyl]cyclobutane-2,4-dicarboxylic acid The title compound was prepared by the procedures described in Example 14. $^1$H NMR (CDCl$_3$, 500MHz) δ 3.6–3.9 (m, 4H), 4.02–4.37 (m, 4H), 4.67 (m, 4H), 5.05 (m, 2H), 6.91–7.35 (m, 18H). MS m/e 711 (M+H)$^+$.

EXAMPLE 44

(1α,2β,3β,4α)-1,3-Di[N-(2-carboxyethyl)-N-(4-phenoxybenzyl)aminocarbonyl]cyclobutane-2,4-dicarboxylic acid The title compound was prepared by the procedures described in Example 14. $^1$H NMR (CDCl$_3$, 500MHz) δ 2.5 (m, 4H), 3.6 (m, 4H), 3.98 (m, 4H), 4.37 (m, 4H), 4.71 (m, 2H), 6.91–7.39 (m, 18H). MS m/e 739 (M+H)$^+$.

EXAMPLE 45

(1α,2β,3β,4α)-1,3-Di[N-propyl-N-(4-phenoxybenzyl) aminocarbonyl]-2-(methoxycarbonyl)cyclobutane-4-carboxylic acid

EXAMPLE 45A (1α,2β,3β,4α)-1,3-Di[N-propyl-N-(4-phenoxybenzyl) aminocarbonyl]cyclobutane-2,4-dicarboxylic acid dimethyl Ester The resultant acid from Example 18 (517 mg, 0.762 mmol) in dichloromethane was treated with an excess of an ether solution of diazomethane. Evaporation of the solvent afforded 519 mg (96%) of the title compound as a foam. $^1$H NMR (CDCl$_3$, 300MHz) 7.40–6.90 (m, 18H), 3.70, 3.63, 3.53, 3.48 (4 s, total 6H), 0.97–0.81 (m, 6H).

EXAMPLE 45B (1α,2β,3β,4α)-1,3-Di[N-propyl-N-(4-phenoxybenzyl) aminocarbonyl]-2-(methoxycarbonyl)cyclobutane-4-carboxylic acid The resultant acid from Example 45A (415 mg, 0.587 mmol) in tetrahydrofuran (4.5 mL) at −10° C. was treated with a solution of LiOH monohydrate (25.5 mg, 0.608 mmol) in water (1.5 mL). The reaction was stirred at −10° to 10° C. for 3 hours and was quenched with 2M HCl and concentrated under reduced pressure. The residue was dissolved in ethyl acetate, washed with brine, dried over Na$_2$SO$_4$ and evaporated. Chromatography of the residue on silica gel eluting with 2–3% methanol in chloroform afforded 218 g (54%) of the title compound as a foam. $^1$H NMR (CDCl$_3$, 300MHz) δ 7.42–6.87 (m, 18H), 3.70, 3.63, 3.54, 3.49 (4 s, total 6H), 0.98–0.78 (m, 6H). Anal calcd for C$_{41}$H$_{44}$N$_2$O$_8$. 0.25 H$_2$O: C, 70.62; H, 6.43; N, 4.02. Found: C, 70.30; H, 6.25; N, 3.96.

EXAMPLE 46

(1α,2β,3β,4α)-1,3-Di[N-propyl-N-(4-phenoxybenzyl) aminocarbonyl]-2-(methoxycarbonyl)cyclobutane-4-carboxylic acid To diisopropylamine (84 μL, 0.60 mmol) in tetrahydrofuran (2 mL) at −78° C. was added n-BuLi (250 μL, 0.54 mmol, 2.15M in hexane). After 10 minutes the resultant compound from Example 45B (166 mg, 0.240 mmol) in tetrahydrofuran (2 mL) was added. After 20 minutes at −78° C. acetic acid (100 μL) in tetrahydrofuran (2 mL) was added, the solvent was evaporated and the residue was partitioned between ethyl acetate and 2M HCl. The mixture was washed with 2M HCl and brine, dried over Na$_2$SO$_4$ and evaporated. Chromatography of the residue on silica gel eluting with 2 % methanol in chloroform afforded 45.5 mg (27%) of the title compound as a foam. $^1$H NMR (CDCl$_3$, 300MHz) δ 7.43–6.90 (m, 18H), 3.68, 3.61, 3.56, 3.49 (4 s, total 6H), 0.97–0.80 (2 m, total 6H).

EXAMPLE 47

(1α,2β,3β,4α)-1,3-Di[N-propyl-N-(4-phenoxybenzyl) aminocarbonyl]cyclobutane-2,4-dicarboxylic acid To the resultant compound mixture from Example 46 (39.4 mg, 0.057 mmol) in tetrahydrofuran (1.5 mL) at 0° C. was added LiOH monohydrate (8.0 mg, 0.19 mmol) in water (0.5 mL). After 90 minutes at 0° C. and 90 minutes at ambient temperature, 4M NaOH (60 μL) was added, and the reaction was stirred at ambient temperature for 40 hours. The reaction was diluted with ethyl acetate, washed with a 1:1 mixture of brine and 2M HCl, dried over Na$_2$SO$_4$ and evaporated. Chromatography of the residue on silica gel eluting with 3% methanol in chloroform afforded 17.0 (44%) mg of the title compound. $^1$H NMR (DMSO-d$_6$, 300MHz) δ 7.49–6.85 (m, 18H), 1.67–1.31 (m, 4H), 0.90–0.68 (m, 6H).

EXAMPLE 48

(1α,2β,3β,4α)-1,3-Di[N-propyl-N-(4-(3,4-methylenedioxyphenoxy)benzyl)aminocarbonyl] cyclobutane-2,4-dicarboxylic acid

EXAMPLE 48A 4-(3,4-Methylenedioxyphenoxy) benzaldehyde

A solution of 3,4-methylenedioxyphenol (7.0 g, 50.7 mmol) in anhydrous DMSO (20 mL) was added dropwise over 30 minutes to a stirred suspension of 60% oil dispersion sodium hydride (2.02 g, 50 mmol) in anhydrous DMSO (40 mL) under a nitrogen atmosphere. Upon completion of addition, a solution of p-fluorobenzaldehyde (6.2 g, 50 mmol) in DMSO (10 mL) was added, and the temperature was slowly raised to 150° C. The reaction mixture was maintained at 130°–160° C. for one hour and then allowed to cool to ambient temperature. After 12 hours at ambient temperature, the reaction mixture was poured onto crushed ice and water, made slightly acidic with concentrated hydrochloric acid and extracted with ether. The combined organic extracts were washed with successively with cold dilute aqueous sodium hydroxide, cold dilute hydrochloric acid, ice-cold water and saturated aqueous sodium chloride solution, dried over sodium sulfate, filtered, and evaporated to give a red liquid which solidified. The solid was triturated with boiling n-pentane, filtered and washed with boiling pentane to give 8.2 g (67%) of the title compound. m.p. 67°–70° C. $^1$H NMR (CDCl$_3$, 300MHz) δ 6.0 (s, 2H), S.6 (m, 2H), 6.8 (d, 1H), 7.04 (m, 2H), 7.84 (m, 2H), 9.92 (s, 1H). MS (DCI/NH$_3$) m/e 243 (M+H)$^+$.

EXAMPLE 48B

N-Propyl-N-[4-(3,4-Methylenedioxyphenoxy)benzyl]amine hydrochloride

A mixture of the compound resulting from Example 48A (6.0 g, 24 mmol), 0.6 g of 10% Pd/C and n-propylamine (9.3 mL) in ethanol (200 mL) was shaken for 24 hours at ambient temperature and then for an additional 48 hours under hydrogen at atmospheric pressure. The reaction mixture was filtered and the filtrate evaporated. The residue was taken up in ether, converted to its hydrochloride salt which was decolorized with norite and recystallized from methanol-ethyl acetate to give 6.2 g (88%) of the title compound as a colorless crystalline solid. m.p. 185°–186° C. $^1$H NMR δ 0.95 (t, 3H), 1.86 (q, 2H), 2.75 (t, 2H), 3.98 (s, 2H), 5.98 (s, 2H), 6.45 (q, 1H), 6.52 (d, 1H), 6.75 (d, 1H), 6.95 (m, 1H), 7.26 (s, 1H), 7.50 (d, 2H), 9.85 (s, 1H). MS (DCl/NH$_3$) m/e 286 (M+H)$^+$.

EXAMPLE 48C (1α,2β,3β,4α)-1,3-Di[N-propyl-N-(4-(3,4-methylenedioxyphenoxy)benzyl)aminocarbonyl]cyclobutane-2,4-dicarboxylic acid To a suspension of 1,2,3,4-cyclobutanetetracarboxylic dianhydride (0.98 g, 5 mmol) in acetonitrile (10 mL) was added 1.6 mL (11 mmol) of Et$_3$N at 0°–5° C. After several minutes, a suspension of the compound resulting from Example 48B (3.23 g, 10.04 mmol) in acetonitrile (30 mL) and Et3N (1.6 mL, 11 mmol) was added to the above stirred mixture. The reaction mixture was stirred for 24 hours at ambient temperature and then poured onto cold dilute hydrochloric acid and extracted with ether. The combined organic extracts were washed with saturated aqueous sodium choride solution, dried over sodium sulfate and evaporated. The residue was taken up in methylene chloride, filtered and evaporated to give a mixture of the 1,2- and 1,3-isomers as a solid foam. Chromatography on silica gel eluting with 97:2.5:0.5 chloroform-methanol-acetic acid afforded 0.8 g (21%) of the title compound. m.p. 95°–100° C. $^1$H NMR (DMSO-d$_6$, 500MHz) δ 0.8 (m, 6H), 1.5 (m, 2H), 2.5 (s, 1H), 2.80 (m, 1H), 3.0 (s, 1H), 3.3 (s, 8H), 3.6 (m, 1H), 3.9 (m, 1H), 4.3 (m, 1H), 4.7 (m, 1H), 6.05 (s, 3H), 6.5–7.2 (m, 14H), 12.4 (s, 2H). MS (DCl/NH$_3$) m/e 267 (M+H)$^+$.

EXAMPLE 49

(1α,2β,3β,4α)-1,3-Di[6-methoxy-1,2,3,4-tetrahydroisoquinolin-2-ylcarbonyl]cyclobutane-2,4-dicarboxylic acid

EXAMPLE 49A

6-Methoxytetrahydroisoquinoline

A mixture of m-methoxyphenethylamine (25 g, 0.165 mol), 37% formaldehyde (12.7 mL) and water (12.7 mL) was stirred for 20 minutes. The reaction mixture was heated at 95°–100° C. for 1.5 hours, cooled, diluted with ice-water, and extracted with toluene (3x). The combined organic extracts were washed with saturated sodium chloride solution (2 ×30 mL), dried over magnesium sulfate, filtered and evaporated. The residual oil was heated with 6N hydrochloric acid (36 mL) for 3 hours, cooled, basified with 50% aqueous sodium hydroxide solution and extracted with methylene chloride. The combined organic extracts were dried over magnesium sulfate and evaporated; the residue was converted to its hydrochloride salt with HCl (g) in isopropanol. The cream-colored crystalline hydrochloride salt was filtered and dried affording the title compound in 52% yield. m.p. 232°–234° C.

EXAMPLE 49B (1α,2β,3β,4α)-1,3-Di[6-methoxy-1,2,3,4-tetrahydroisoquinolin-2-ylcarbonyl]cyclobutane-2,4-dicarboxylic acid and (1α,2β,3β,4α)-1.2-Di[6-methoxy-1,2,3,4-tetrahydroisoquinolin-2-ylcarbonyl]cyclobutane-3.4-dicarboxylic acid A mixture of the compound resulting from Example 49A (6.0 g, 0.03 mol) in methanol (30 mL) containing Et$_3$N (8.4 mL) was added to a stirred suspension of 1,2,3,4-cyclobutanetetracarboxylic dianhydride in acetonitrile (15 mL) at 0° C. under a nitrogen atmosphere. The cooling bath was removed, and the mixture was stirred at ambient temperature for 48 hours and then evaporated. The residue was taken up in methylene chloride (26 mL), and the resulting solution was washed with water, 2N hydrochloric acid, water and brine, dried over magnesium sulfate, filtered and evaporated to give 4.3 g of a cream-colored solid. Silica gel chromatography eluting with 92:5:3 chloroform-methanol-formic acid gave a mixture of the.1,2- and 1,3-isomers. $^1$H NMR (CDCl$_3$, 500MHz) δ 2.8 (m, 6H), 3.6 (m, 6H), 3.78 (m, 6H), 3.98 (m, 1H), 4.1 (d, 1H), 4.5 (m, 4H), 6.7 (m, 4H), 7.05 (t, 2H). MS (DCl/NH$_3$) m/e 523 (M+H)$^+$.

EXAMPLE 50

(1α,2β,3β,4α)-1,3-Di[N-propyl-N-(4-(2-methylphenoxy)benzyl)aminocarbonyl]cyclobutane-2,4-dicarboxylic acid

EXAMPLE 50A 4-(2-Methylphenoxy)benzaldehyde

A solution of o-cresol (5.4 g, 50.7 mmol) in DMSO (10 mL) was added dropwise to a stirred mixture of 60% oil dispersion sodium hydride (2.02 g, 50.5 mmol) in DMSO (20 mL). After stirring for 1 hour at ambient temperature, a solution of p-fluorobenzaldehyde (5.36 mL, 50 mmol) in DMSO (10 mL) was added dropwise. After the addition was complete, the reaction mixture was gradually heated to 140–160° C. and maintained at that temperature for 1 hour. The reaction mixture was poured into ice-water and extracted with ether. The combined organic extracts were washed successively with ice-cold dilute aqueous sodium hydroxide solution, dilute aqueous hydrochloric acid solution, water and saturated aqueous sodium chloride solution, dried over sodium sulfate and evaporated to give a brown liquid. Chromatography on silica gel eluting with 95:5 hexane-ethyl acetate afforded 6.1 g (51%).of the title compound. $^1$H NMR (CDCl$_3$, 300MHz) δ 2.19 (s, 3H), 6.98 (m, 3H), 7.2 (m, 3H), 7.82 (m, 2H), 9.9 (s, 1H). MS (DCl/NH$_3$) m/e 213 (M+H)$^+$.

EXAMPLE 50B

N-Propyl-N-4-(2-methylphenoxy)benzylamine hydrochloride

A mixture of the compound resulting from Example 50A (6.4 g, 30.1 mmol), n-propylamine (10 mol) in ethanol (100 mL) and 0.64 g of 10% Pd/C was first shaken for 24 hours at ambient temperature and then for an additional 24 hours with 4 atmospheres pressure of hydrogen. The reaction mixture was filtered and the filtrate evaporated under reduced pressure. The residue was taken up in ether containing a small amount of methanol and filtered from suspended impurities. The filtrate was acidified with hydrogen chloride (g) in isopropanol under a nitrogen atmosphere. The hydrochloride salt was washed with ether and dried in vacuo to give 7.5 g (86%) of the title compound as a fine colorless microcrystalline solid. m.p. 175°–177° C. H NMR (CDCl$_3$, 300MHz) δ 0.99 (t, 3H), 1.88 (q, 2H), 2.18 (s, 3H), 2.78 (t, 2H), 4.0 (s, 2H), 6.88 (m, 3H), 7.2 (m, 3H), 7.54 (d, 2H), 9.8 (s, 1H). MS (DCI/NH$_3$) m/e 256 (M+H)$^+$.

EXAMPLE 50C

(1α,2β,3β,4α)-1,3-Di[N-propyl-N-(4-(2-methylphenoxy)benzyl)aminocarbonyl]cyclobutane-2,4-dicarboxylic acid The free base of the compound resulting from Example 50B was taken up in acetonitrile (20 mL) and added dropwise to a well stirred suspension of 1,2,3,4-cyclobutanetetracarboxylic dianhydride (0.98 g, 5 mmol) in acetonitrile (5 mL) containing Et$_3$N (0.73 mL, 10 mmol). After 3 hours, the reaction mixture was evaporated under reduced pressure, and the residual liquid was poured onto ice-aqueous hydrochloric acid and extracted with methylene chloride. The combined organic extracts were washed with saturated aqueous sodium chloride solution, dried over sodium sulfate, filtered and evaporated to give a colorless foam. Chromatography on silica gel eluting with 98:1.5:0.5 chloroform-methanol-acetic acid afforded 1.089 g of the title compound as a colorless foam. $^1$H NMR (CDCl$_3$, 300MHz) δ 0.8 (m, 6H), 1.5 (m, 4H), 2.19 (m, 6H), 2.5 (t, 2H), 2.8 (m, 1H), 2.98 (m, 1H), 3.3 (m, 2H), 3.9 (m, 2H), 4.3 (q, 2H), 6.8–7.3 (m, 16H), 12.4 (s, 2H).

EXAMPLE 51

(1α,2β,3β,4α)-1,3-Di[N-propyl-N-(3-phenoxybenzyl)aminocarbonyl]cyclobutane-2,4-dicarboxylic acid

EXAMPLE 51A

N-Propyl-N-(3-phenoxybenzyl)amine

3-Phenoxybenzaldehyde (2.00 mL, 2.29 g, 11.6 mmol), n-propylamine (0.95 mL, 0.68 g, 11.5 mmol), and p-toluenesulfonic acid monohydrate (15 mg, 0.08 mmol) were dissolved in absolute ethanol (15 mL), then heated to 80° C. in a sealed tube for 2.5 hours. The reaction was cooled to room temperature, transfered to a round-bottom flask, then sodium borohydride (440 mg, 11.6 mmol) was added, followed by heating under reflux for 2.5 hours. The reaction was concentrated, the residue partitioned between water and EtOAc, the EtOAc layer washed with water and brine. After drying with Na$_2$SO$_4$, filtration, and concentration, the residue was purified by chromatography on silica gel eluting with 4:6 followed by 3:7 hexane-EtOAc to give 1.59 g (57%) of the title compound as a light yellow oil. $^1$H NMR (CDCl$_3$) δ 7.30 (m, 3H), 7.08 (m, 2H), 7.00 (m, 3H), 6.88 (dd, 1H), 3.77 (s, 2H), 2.60 (t, 2H), 1.53 (m, 2H), 0.92 (t, 3H). MS (DCI/NH$_3$) m/e 242 (M+H)$^+$.

EXAMPLE 51B

(1α,2β,3β,4α)-1,3-Di[N-propyl-N-(3-phenoxybenzyl)aminocarbonyl]cyclobutane-2,4-dicarboxylic acid 1,2,3,4-Cyclobutanetetracarboxylic dianhydride (313 mg, 1.60 mmol) was slurried in CH$_3$CN (4.0 mL), then the compound resulting from Example 51A (803 mg, 3.30 mmol) was added. The reaction was stirred at room temperature under N$_2$ overnight, then diluted with EtOAc, washed with 2×1M H$_3$PO$_4$ and brine, and dried over Na$_2$SO$_4$. Chromatography of the residue using 98.5:1.5:0.5 CHCl$_3$-MeOH-CH$_3$CO$_2$H gave a glass which was dissolved in CH$_3$CN (10 mL). Water (10 mL) was added to the CH$_3$CN solution, then the solution was frozen and lyophilized to give 390 mg (36%) of the title compound as a white solid. $^1$H NMR (DMSO-d$_6$) δ 7.39, 7.28, 7.16, 7.00, 6.95–6.81 (all m, total 18H), 4.63, 4.38 (both m, total 4H), 4.00, 3.85 (both m, total 4H), 3.50, 3.25, 3.05, 2.80 (all m, total 4H), 1.45 (m, 4H), 0.80 (m, 6H). MS (FAB$^+$) m/e 679 (M+H)$^+$. Anal. calcd for C$_{40}$H$_{42}$N$_2$O$_8$·0.25H$_2$O: C, 70.32; H, 6.27; N, 4.10. Found: C, 70.44; H, 6.41; N, 3.96.

EXAMPLE 52

(1α,2β,3β,4α)-1,3-Di[N-propyl-N-(5-phenoxyfurfuryl)aminocarbonyl]cyclobutane-2,4-dicarboxylic acid

EXAMPLE 52A

5-Phenoxy-2-furaldehyde

Phenol (3.80 g, 40.4 mmol) in DMSO (25 mL) was added dropwise to a suspension of NaH (60%, 1.63 g, 40.4 mmol) in DMSO (25 mL) over a period of 15 minutes. After another 15 minutes, a solution of 5-nitro-2-furaldehyde (4.85 g, 34.4 mmol) in DMSO (20 mL) was added. The reaction was stirred at room temperature for 4.5 hours, then the reaction was partitioned between ice-water and Et$_2$O, which resulted in an emulsion, so brine was added to separate the layers. The aqueous layer was extracted with Et$_2$O and the combined Et$_2$O layers were washed with 7% KOH, dried over Na$_2$SO$_4$ and concentrated in vacuo to afford a brown oil. Vacuum distillation (2.8 mm Hg, 137°–8° C.) gave 3.3 g (51%) yellow oil. $^1$H NMR (CDCl$_3$) δ 9.42 (s, 1H), 7.42 (m, 2H), 7.28 (m, 1H), 7.20 (m, 3H), 5.55 (d, 1H). MS (DCI/NH$_3$) m/e 189 (M+H)+, 206 (M+H+NH$_3$)$^+$.

EXAMPLE 52B

(1α,2β,3β,4α)-1,3-Di[N-propyl-N-(5-phenoxyfurfuryl)aminocarbonyl]cyclobutane-2,4-dicarboxylic Using the compound resulting from Example 52A, N-propyl-N-(5-phenoxyfurfuryl)amine was prepared by the method of Example 51.A. $^1$H NMR (CDCl$_3$) δ 7.32 (m, 2H), 7.10, (m, 1H), 7.04(m, 2H), 6.12 (d, 1H), 5.51 (d, 1H), 3.70 (s, 2H), 2.59 (t, 2H), 1.54 (m, 2H), 0.92 (t, 3H). MS (DCI/NH$_3$) m/e 232 (M+H)$^+$.

Using the amine described above, the title compound was prepared using the method of Example 51B $^1$H NMR (DMSO-d6) δ 7.40 (m, 4H), 7.17 (m, 2H), 7.05 (m, 2H), 7.02 (m, 2H), 6.38, 6.30 (d, m, total 2H), 5.70 (m,2H), 4.52, 4.40, 4.21 (all m, total 4H), 4.00, 3.90, 3.55 (all m, total 4H), 3.40, 3.29, 3.12, 2.98 (all m, total 4H), 1.45 (m, 4H), 0.80 (m, 6H). MS (FAB$^+$) m/e 659 (M+H)$^+$. Anal calcd for C$_{36}$H$_{38}$N$_2$O$_{10}$: C, 65.64; H, 5.81; N, 4.25. Found: C, 65.57; H, 5.88; N, 4.29.

EXAMPLE 53

(1α,2β,3β,4α)-1,3-Di[N-propyl-N-(5-phenoxythien-2-ylmethyl)aminocarbonyl]cyclobutane-2,4-dicarboxylic acid

EXAMPLE 53A

5-Phenoxythiophene-2-carboxaldehyde

Using 5-nitrothiophene-2-carboxaldehyde, 5-phenoxythiophene-2-carboxaldehyde was prepared by the method of Example 52A, except chromatography using 9:1 hexane-EtOAc was used for purification. $^1$H NMR (CDCl$_3$) δ 9.72 (s, 1H), 7.54 (d, 1H), 7.42 (m, 2H), 7.25 (m, 1H), 7.20 (m, 2H), 6.51 (d, 1H). MS (DCI/NH$_3$) m/e 205 (M+H)$^+$, 222 (M+H+NH$_3$)$^+$.

EXAMPLE 53B (1α,2β,3β,4α)-1,3-Di[N-propyl-N-(5-phenoxythien-2-ylmethyl)aminocarbonyl]cyclobutane-2,4-dicarboxylic acid Using the compound resulting from Example 53A, N-propyl-N-(5-phenoxythien-2-ylmethyl)amine was prepared by the method of Example 51A. $^1$H NMR (CDCl$_3$) δ 7.32 (m, 2H), 7.10, (m, 3H), 6.52 (dt, 1H), 6.38 (d, 1H), 3.88 (d, 2H), 2.63 (t, 2H), 1.54 (m, 2H), 0.92 (t, 3H); MS (DCI/NH$_3$) m/e 248 (M+H)$^+$.

Using the amine prepared above, the title compound was prepared by the method of Example 51B. $^1$H NMR (DMSO-d6) δ 7.38 (m, 4H), 7.10 ( m, 6H), 6.80 (m, total 2H), 6.53, 6.45 (both m, total 2H), 4.70, 4.52, 4.40 (all m, total 4H), 3.95, 3.54 (both m, total 4H), 3.43, 3.25, 3.14, 2.91 (all m, total 4H), 1.50 (m, total 4H), 0.80 (m, total 6H). MS (FAB−) m/e 689 (M−H)$^-$. Anal calcd for C$_{36}$H$_{38}$N$_2$O$_8$S$_2$·0.25 H$_2$O: C, 62.19; H, 5.58; N, 4.03. Found: C, 62.21; H, 5.59; N, 3.93.

EXAMPLE 54

(1α,2β,3β,4α)-1,3-Di[N-propyl-N-(4-(furan-2-yloxybenzyl)aminocarbonyl]cyclobutane-2,4-dicarboxylic acid

EXAMPLE 54A 5-(4-Ethoxycarbonylphenoxy)-2-furaldehyde

Using ethyl-4-hydroxybenzoate, the title compound was prepared by the method of Example 52A, except chromatography using 3:1 hexane-EtOAc was used for purification. $^1$H NMR (CDCl$_3$) δ 9.45 (s, 1H), 8.10 (m, 2H), 7.25 (d, 1H), 7.19 (m, 2H), 5.75 (d, 1H), 4.40 (q, 2H), 1.41 (t, 3H). MS (DCI/NH$_3$) m/e 261 (M+H)$^+$, 278 (M+H+NH$_3$)$^+$.

EXAMPLE 54B 5-(4-Ethoxycarbonylphenoxy)-2-furoic acid

A solution of potassium dihydrogen phosphate (10.8 g, 79.0 mmol) and sodium chlorite (80%, 12.0 g, 106 mmol) in water (95 mL) was added to a solution of the compound resulting from Example 54A (3.00 g, 11.5 mmol) in t-butanol (240 mL) and 2-methyl-2-butene (57 mL). The two-phase reaction mixture was mechanically stirred at room temperature for 2 hours, then the aqueous layer was removed, and the organic layer concentrated. The aqueous layer and the organic residue were combined, the pH was adjusted to 2 with 1.1 N NaHSO$_4$, then extracted with Et$_2$O. The Et$_2$O layer was washed with 5% sodium bisulfite, then extracted with saturated NaHCO$_3$. The saturated NaHCO$_3$ layer was washed with 3×Et$_2$O, then the pH was adjusted to 1 with 1.1N NaHSO$_4$, and extracted with 3×Et$_2$O. After drying over Na$_2$SO$_4$ and concentrating under reduced pressure 1.10 g (34%) of the title compound as a light yellow solid was obtained. $^1$H NMR (CD$_3$OD) δ 8.08 (m, 2H), 7.27 (d, 1H), 7.21 (m, 2H), 5.90 (d, 1H), 4.36 (q, 2H), 1.39 (t, 3H). MS (DCI/NH$_3$) m/e 294 (M+H+NH$_3$)$^+$.

EXAMPLE 54C

Ethyl 4-(furan-2-yloxy)benzoate

To the compound resulting from Example 54B (1.05 g, 3.80 mmol) slurried in quinoline (1.7 mL) was added copper powder (70 mg). The reaction was heated to 200° C. for 1 hour, cooled to room temperature, and partioned between Et$_2$O and 1M H$_3$PO$_4$. The Et$_2$O layer was washed with 3×1M H$_3$PO$_4$, 3×saturated NaHCO$_3$ and brine, dried over Na$_2$SO$_4$ and concentrated in vacuo. Chromatography of the residue eluting with 2% EtOAc in hexanes gave 550 mg of the title compound as a yellow oil (62%). $^1$H NMR (CDCl$_3$) δ 8.04 (m, 2H), 7.10 (dd, 1H), 7.03 (m, 2H), 6.40 (dd, 1H), 5.70 (dd, 1H), 4.36 (q, 2H), 1.39 (t, 3H). MS (DCI/NH$_3$) m/e 233 (M+H)$^+$, 250 (M+H+NH$_3$)$^+$.

EXAMPLE 54D 4-(Furan-2-yloxy)benzyl alcohol

A solution of the compound resulting from Example 54C (535 mg, 2.30 mmol) in THF (4 mL) was added to a solution of LAH in THF (4 mL of 1.0M LAH). The reaction mixture was stirred at room temperature for 1 hour and then cooled to 5° C. Water (0.13 mL), 15% NaOH (0.13 mL), and water (0.35 mL) were added sequentially, and the mixture was stirred for 15 minutes. After the addition of Et$_2$O and MgSO$_4$, the mixture was filtered through a small plug of silica gel and the filtrate concentrated under reduced pressure to afford 435 mg (100%) of the title compound as a yellow oil. $^1$H NMR (CDCl$_3$) δ 7.35 (m, 2H), 7.05 (dd, 1H), 7.03 (m, 2H), 6.44 (dd, 1H), 5.60 (dd, 1H), 4.66 (d, 2H), 1.63 (t, 1H); MS (DCI/NH$_3$) m/e 191 (M+H)$^+$.

EXAMPLE 54E 4-(Furan-2-yloxy)benzaldehyde

To the compound resulting from Example 54D (430 mg, 2.30 mmol) dissolved in 9:1 CH$_2$Cl$_2$—CH$_3$CN (22 mL) was added N-morpholine-N-oxide (400 mg, 3.40 mmol) and powdered activated molceular sieves (2.10 g). After stirring for 10 minutes, tetrapropylammonium perruthenate (40 mg, 0.11 mmol) was added, the reaction was stirred at room temperature for 30 minutes, and then Celite® and Et$_2$O were added. The mixture was filtered through a small plug of silica gel, and the filtrate concentrated to afford 350 mg (81%) of the title compound as a brown oil. $^1$H NMR (CDCl$_3$) δ 9.95 (s, 1H), 7.88 (m, 2H), 7.12 (m, 3H), 6.42 (dd, 1H), 5.76 (dd, 1H). MS (DCI/NH$_3$) m/e 189 (M+H)$^+$, 206 (M+H+NH$_3$)$^+$.

EXAMPLE 54F

N-Propyl-N-4-(furan-2-yloxy) benzylamine,

Using the compound resulting from Example 54E, the title compound was prepared by the method of Example 51A. $^1$H NMR (CDCl$_3$) δ 7.28 (m, 2H), 7.05 (dd, 1H), 6.99 (m, 2H), 6.33 (dd, 1H), 5.56 (dd, 1H), 3.77 (s, 2H), 2.60 (t, 2H), 1.55 (m, 2H), 0.93 (t, 3H). MS (DCI/NH$_3$) (M+H)$^+$ 232.

EXAMPLE 54G (1α,2β,3β,4α)-1,3-Di[N-propyl-N-(4-(furan-2-yloxybenzyl)aminocarbonyl]cyclobutane-2,4-dicarboxylic acid Using the compound resulting from Example 54F, the title compound was prepared by the method of Example 51B. $^1$H NMR (DMSO-d$_6$) δ 7.28, 7.25 (both m, total 6H), 7.02, 6.95 (both m, total 4H), 6.48 (m, 2H), 5.78 (m, 2H), 4.75, 4.27 (both m, total 4H), 4.00, 3.60 (both m, total 4H), 3.70–3.20, 3.00, 2.80 (envelope, m, m, total 4H), 1.48 (m, 4H), 0.80 (m, 6H). MS (FAB$^+$) m/e 657 (M+H)$^+$. Anal calcd for $C_{36}H_{38}N_2O_{10}$·0.5 $H_2O$: C, 64.76; H, 5.89; N, 4.20. Found: C, 64.84; H, 5.97; N, 4.05.

EXAMPLE 55

(1α,2β,3β,4α)-1,3-Di[N-propyl-N-(4-(thiazol-2-yloxybenzyl)aminocarbonyl]cyclobutane-2,4-dicarboxylic acid Using ethyl-4-hydroxybenzoate and 2-bromothiazole, ethyl 4-(thiazol-2-yloxy)benzoate was prepared by the method of Example 52A, except the reaction was heated to 120° C. overnight, and chromatography using 9:1 hexane-EtOAc was used for the purification. $^1$H NMR (CDCl$_3$) δ 8.10 (m, 2H), 7.35 (m, 2H), 7.28 (d, 1H), 6.90 (d, 1H), 4.38 (q, 2H), 1.39 (t, 3H). MS (DCl/NH$_3$) m/e 250 (M+H)$^+$, 267 (M+H+NH$_3$)$^+$.

Using the ester prepared above and the procedures described in Example 54D provided 4-(thiazol-2-yloxy) benzyl alcohol. $^1$H NMR (CDCl$_3$) δ 7.43 (m, 2H), 7.28 (m, 2H), 7.23 (d, 1H), 6.82 (d, 1H), 4.70 (d, 2H), 1.88 (t, 1H). MS (DCl/NH$_3$) m/e 208 (M+H)$^+$.

Using the alcohol prepared above and the procedures described in Example 54E, except chromatography using 4:1 hexane-EtOAc was used for purification, provided 4-(thiazol-2-yloxy)benzaldehyde. $^1$H NMR (CDCl$_3$) δ 10.00 (s, 1H), 7.95 (m, 2H), 7.46 (m, 2H), 7.30 (d, 1H), 6.95 (d, 1H). MS (DCl/NH$_3$) role 206 (M+H)$^+$, 223 (M+H+NH$_3$)$^+$.

Using the aldehyde prepared above and the procedures described in Example 51 A, except 3–5% MeOH in CHCl$_3$ was used for the chromatography, to provide N-propyl-N-(4-(thiazoly-2-yloxy)benzyl)amine. $^1$H NMR (CDCl$_3$) δ 7.39 (m, 2H), 7.23 (d, 1H), 7.23 (m, 2H), 6.80 (d, 1H), 5.56 (dd, 1H), 3.80 (s, 2H), 2.63 (t, 2H), 1.55 (m, 2H), 0.96 (t, 3H). MS (DCl/NH$_3$) role 249 (M+H)$^+$.

Using the amine prepared above, the title compound was prepared by the method of Example 51B. $^1$H NMR (DMSO-d$_6$) δ 7.40–7.20 (envelope, 12H), 4.77, 4.32 (both m, total 4H), 4.00, 3.90, 3.60 (all m, total 4H), 3.55–3.20, 3.02, 2.83 (envelope, m, m, total 4H), 1.50 (m, 4H), 0.80 (m, 6H). MS (FAB+) m/e 693 (M+H)$^+$. Anal calcd for $C_{34}H_{36}N_4O_8S_2$·0.5 $H_2O$: C, 58.19; H, 5.31; N, 7.98. Found: C, 58.42; H, 5.22; N, 7.96.

EXAMPLE 56

(1α,2β,3β,4α)--1,3-Di[N-propyl-N-(4-(pyrrol-1-ylmethyl) benzyl)aminocarbonyl]cyclobutane-2,4-dicarboxylic acid

EXAMPLE 56A

N-(4-(Pyrrol-1-ylmethyl)benzyl)amine

Using pyrrole and 4-(bromomethyl)benzonitrile and the method of Example 53A, except using DMF as the solvent, provided N-(4-cyanobenzyl)pyrrole. $^1$H NMR (CDCl$_3$) δ 7.62 (m, 2H), 7.14 (m, 2H), 6.69 (m, 2H), 6.24 (m, 2H), 5.15 (s, 2H). MS (DCl/NH$_3$) m/e 183 (M+H)$^+$, 200 (M+H+NH$_3$)$^+$.

Using the nitrile prepared above and the method of Example 54D, except after 1 hour at room temperature the reaction was heated under reflux for 75 minutes, provided the title compound. $^1$H NMR (CDCl$_3$) δ 7.28 (m, 2H), 7.10 (m, 2H), 6.69 (m, 2H), 6.19 (m, 2H), 5.05 (s, 2H) 3.85 (s, 2H). MS (DCl/N H3) m/e 187 (M+H)$^+$, 204 (M+H+NH$_3$)$^+$.

EXAMPLE 56B

N-[4-(Pyrrol-1-ylmethyl)benzyl]propylamide.

To the compound resulting from Example 56A (1.00 g, 5.38 mmol) and triethylamine (0.60 g, 0.82 mL, 5.93 mmol) in CH$_2$Cl$_2$ (8 mL) cooled to 0° C. was added propionyl chloride (0.50 g, 0.47 mL, 5.41 mmol) in CH$_2$Cl$_2$ (5.5 mL) dropwise. The bath was removed and the reaction mixture stirred for 10 minutes, then diluted with EtOAc. The resulting solution was washed with 3×1M H$_3$PO$_4$, 3×saturated NaHCO$_3$ and brine, dried over Na$_2$SO$_4$ and concentrated under reduced pressure to afford 1.25 g (96%) of the title compound as a white solid. $^1$H NMR (CDCl$_3$) δ 7.24 (d, 2H), 7.08 (d, 2H), 6.69 (m, 2H), 6.19 (m, 2H), 5.75 (br s, 1H), 5.05 (s, 2H) 4.40 (d, 2H), 2.23 (q, 2H), 1.18 (t, 3H). MS (DCl/NH$_3$) m/e 243 (M+H)$^+$, 260 (M+H+NH$_3$)$^+$.

EXAMPLE 56C

N-Propyl-N-(4-(pyrrol-1-ylmethyl)benzyl)amine

A solution of the compound resulting from Example 56B (1.20 g, 4.96 mmol) in THF (8 mL) was added to a solution of LAH in THF (9.9 mL of 1.0M LAH). The reaction mixture was heated under reflux 3 hours, then cooled to 5° C. Water (0.50 mL), 15% NaOH (0.50 mL), and water (1.50 mL) were added sequentially, and the mixture was stirred for 15 minutes. After the addition of Et$_2$O and MgSO$_4$, the mixture was filtered through a small plug of silica gel, which was rinsed with CH$_2$Cl$_2$. The filtrate was concentrated under reduced pressure and purified by chromatography eluting with 97:3 CHCl$_3$-MeOH to give a yellow oil (880 mg, 78%). $^1$H NMR (CDCl$_3$) δ 7.28 (d, 2H), 7.08 (d, 2H), 6.69 (m, 2H), 6.19 (m, 2H), 5.05 (s, 2H) 3.77 (s, 2H), 2.59 (t, 2H), 1.55 (m, 2H), 0.93 (t, 3H). MS (DCl/NH$_3$) m/e 229 (M+H)$^+$.

EXAMPLE 56D (1α,2β,3β,4α)-1,3-Di[N-propyl-N-(4-(pyrrol-1-ylmethyl) benzyl)aminocarbonyl]cyclobutane-2,4-dicarboxylic acid Using the compound resulting from Example 56C, the title compound was prepared by the method of Example 51B. $^1$H NMR (DMSO-d$_6$) δ 7.25–7.05 (envelope, 8H), 6.80 (m, 4H), 6.02 (m, 4H), 5.08 (m, 4H), 4.70, 4.25 (both m, total 4H), 4.05–3.80, 3.69–3.55 (both envelopes, total 4H), 3.55–3.20, 2.97, 2.78 (envelope, m, m, total 4H), 1.45 (m, 4H), 0.78 (m, 6H). MS (FAB+) m/e 653 (M+H)$^+$. Anal calcd for $C_{38}H_{44}N_4O_6$: C, 69.92; H, 6.79; N, 8.58. Found: C, 69.68; H, 6.89; N, 8.36.

EXAMPLE 57

(1α,2β,3β,4α)-1,3-Di{N-propyl-N-[4-(3-methylphenoxy) benzyl]aminocarbonyl}cyclobutane-2,4-dicarboxylic acid

EXAMPLE 57A 4-(3-Methylphenoxy) benzaldehyde m-Cresol (2.58 g, 24.0 mmol) in DMSO (5 mL) was added dropwise to a suspension of NaH (60%, 1.63 g, 40.4 mmol) in DMSO (10 mL) over a period of 15 minutes. After an additional 15 minutes, a solution of p-fluorobenzaldehyde (2.54 g, 20.5 mol) in DMSO (5 mL) was added. The reaction was heated at 125° C. for 3 hours, then cooled to room temperature and partitioned between 1N HCl and Et$_2$O. The Et$_2$O layer was washed with 15% NaOH and brine, dried over Na$_2$SO$_4$. Vacuum distillation (3.4 mm Hg, 154°–8° C.) afforded 2.35 g of an oil which was purified by chromatography eluting with 9:1 hexane-Et$_2$O to give 1.98 g (46%) of the title compound as a colorless oil. $^1$H NMR (CDCl$_3$) δ 9.92 (s, 1H), 7.85 (m, 2H), 7.30 (m, 1H), 7.05 (m, 3H), 6.90 (m, 2H), 2.38 (s, 3H). MS (DCl/NH$_3$) m/e 213 (M+H)$^+$, 230 (M+H+NH$_3$)$^+$.

EXAMPLE 57B (1α,2β,3β,4α)-1,3-Di{N-propyl-N-[4-(3-methylphenoxy)benzyl]aminocarbonyl}cyclobutane-2,4-dicarboxylic acid Using the compound resulting from Example 57A and the procedures described in Example 51A provided N-propyl-N-[4-(3-methylphenoxy)benzyl]amine. $^1$H NMR (CDCl$_3$) δ 7.28 (m, 2H), 7.30 (m, 1H), 6.95 (m, 2H), 6.90 (m, 1H), 6.80 (m, 2H), 3.77 (s, 2H), 2.33 (s, 3H), 2.62 (t, 2H), 1.55 (m, 2H), 0.93 (t, 3H). MS (DCI/NH$_3$) m/e 256 (M+H)$^+$.

Using the amine prepared above and the procedures described in Example 51B provided the title compound. $^1$H NMR (DMSO-d6) δ 7.27 (m, 6H), 6.93 (m, 6H), 6.80 (m, 4H), 4.70, 4.27 (both m, total 4H), 3.95, 3.60 (both m, total 4H), 3.55–3.20, 3.00, 2.82 (envelope, m, m, total 4H), 2.27 (m, 6H), 1.50 (m, 4H), 0.80 (m, 6H). MS (FAB+) m/e 707 (M+H)$^+$. Anal calcd for C$_{42}$H$_{46}$N$_2$O$_8$: C, 71.37; H, 6.56; N, 3.96. Found: C, 71.13; H, 6.52; N, 3.86.

EXAMPLE 58

(1α,2β,3β,4α)-1,3-Di{N-propyl-N-[4-(naphth-2-yloxy)benzyl]aminocarbonyl}cyclobutane-2,4-dicarboxylic acid Using 2-naphthol and the method of Example 57A, except the vacuum distillation was omitted, afforded 4-(naphth-2-yloxy)benzaldehyde. $^1$H NMR (CDCl$_3$) δ 9.94 (s, 1H), 7.90 (m, 4H), 7.78 (m, 1H), 7.50 (m, 3H), 7.28 (dd, 1H), 7.12 (m, 2H). MS (DCI/NH$_3$) m/e 249 (M+H)$^+$, 266 (M+H+NH$_3$)$^+$.

Using the aldehyde prepared above and the procedures described in Example 51A afforded N-propyl-N-[4-(naphth-2-yloxy)benzyl]amine. $^1$H NMR (CDCl$_3$) δ 7.82 (m, 2H), 7.70 (m, 1H), 7.42 (m, 2H), 7.32 (m, 1 H), 7.27 (m, 3H), 7.04 (m, 2H), 3.79 (s, 2H), 2.62 (t, 2H), 1.55 (m, 2H), 0.93 (t, 3H). MS (DCI/NH$_3$) m/e 292 (M+H)$^+$.

Using the amine prepared above and the procedures described in Example 51B afforded the title compound. $^1$H NMR (DMSO-d$_6$) δ 7.92 (m, 4H), 7.80 (m, 2H), 7.44 (m, 6H), 7.27 (m, 6H), 7.05 (m, 4H), 4.77, 4.30 (both m, total 4H), 4.00, 3.60 (both m, total 4H), 3.55–3.24, 3.03, 2.85 (envelope, m, m, total 4H), 1.50 (m, 4H), 0.80 (m, 6H). MS (FAB+) m/e 779 (M+H)$^+$. Anal calcd for C$_{48}$H$_{46}$N$_2$O$_8$·0.5 H20: C, 73.59; H, 5.98; N, 3.58. Found: C, 73.59; H, 5.78; N, 3.50.

EXAMPLE 59

(1α,2β,3β,4α)-1,3-Di{N-propyl-N-[(3-methyl-4-phenoxy)benzyl]aminocarbonyl}cyclobutane-2,4-dicarboxylic acid

EXAMPLE 59A

3-Methyl-4-phenoxybenzonitrile

Using phenol and 2-fluoro-5-nitrotoluene and the procedures described in Example 52A, except the reaction was heated to 60° C. overnight and vacuum distilled at 4.5 mm Hg, 174°–5° C., provided 3-methyl-4-phenoxynitrobenzene. $^1$H NMR (CDCl$_3$) δ 8.16 (dd, 1H), 8.00 (dd, 1H), 7.42 (m, 2H), 7.23 (m, 1H), 7.05 (m, 2H), 6.78 (d, 1H),2.42 (s, 3H). MS (DCI/NH$_3$) role 247 (M+H)+.

The nitro compound prepared above was reduced under H$_2$ using 10% Pd/C catalyst in MeOH to give 3-methyl-4-phenoxyaniline. $^1$H NMR (CDCl$_3$) δ 7.27 (m, 2H), 6.97 (m, 1H), 6.83 (m, 2H), 6.80 (d, 1H), 6.60 (d, 1H), 6.52 (m, 1H), 3.53 (br s, 2H), 2.11 (s, 3H). MS (DCI/NH$_3$) m/e 200 (M+H)$^+$, 217 (M+H+NH$_3$)$^+$.

The amine prepared above (2.75 g, 13.8 mmol) was added to 2N HCl (20 mL), then cooled to 5° C., giving a thick purple slurry. A solution of sodium nitrite (0.84 g, 14.2 mmol) in water (2 mL) was added dropwise, keeping the reaction temperature −5° C. Addition of another small portion of sodium nitrite to the reaction resulted in a positive HONO test with a KI-starch strip, so the pH was adjusted to 7–8 using solid Na$_2$CO$_3$. This solution was added in portions to a vigorously stirred mixture of toluene (10 mL) and a solution of sodium cyanide (1.65 g, 33.6 mmol) and copper (I) cyanide (1.45 g, 16.2 mmol) in water (15 mL), keeping the reaction temperature −5° C. The very thick, brown reaction mixture was diluted with more toluene, stirred at 5° C. for 15 minutes, then at room temperature for 2 hours. The reaction mixture was added to EtOAc and 2N HCl; the organic layer was dried with Na$_2$SO$_4$ and concentrated in vacuo. The residue obtained was chromatographed eluting with 95:5 hexane-Et$_2$O to give the title compound as an orange-red oil (500 mg, 17%). $^1$H NMR (CDCl$_3$) δ 7.55 (d, 1H), 7.40 (m, 3H), 7.20 (m, 1H), 7.00 (m, 2H), 6.79 (d, 1H), 2.35 (s, 3H). MS (DCI/NH$_3$) m/e 227 (M+H+NH$_3$)$^+$.

EXAMPLE 59B

3-Methyl-4-phenoxybenzaldehyde

To the compound resulting from Example 59A (490 mg, 2.34 mmol) dissolved in toluene (12 mL) and cooled to 0° C. was added 5 mL of 1.5M DIBAL in toluene. The reaction mixture was stirred at 0°–10° C. for 2.5 hours, then EtOAc and 1N HCl were added. The organic layer was washed with water and brine, dried over Na$_2$SO$_4$ and concentrated under reduced pressure. Chromatography of the residue eluting with 95:5 hexane-EtOAc gave the title compound as an orange oil (330 mg, 66%). $^1$H NMR (CDCl$_3$) δ 9.90 (s, 1H), 7.80 (d, 1H), 7.63 (dd, 1H), 7.40 (m, 2H), 7.19 (m, 1H), 7.03 (m, 2H), 6.85 (d, 1H), 2.40 (s, 3H). MS (DCI/NH$_3$) m/e 213 (M+H)$^+$, 230 (M+H+NH$_3$)$^+$.

EXAMPLE 59C (1α,2β,3β,4α)-1,3-Di{N-propyl-N-[(3-methyl-4-phenoxy)benzyl]aminocarbonyl}cyclobutane-2,4-dicarboxylic acid Using the compound resulting from Example 59B and the procedures described in Example 51A afforded N-propyl-N-(3-methyl-4-phenoxybenzyl)amine. $^1$H NMR (CDCl$_3$) δ 7.30 (m, 2H), 7.22 (d, 1H), 7.10 (dd, 1H), 7.03 (m, 1H), 6.88 (m, 3H), 3.76 (s, 2H), 2.64 (t, 2H), 2.22 (s, 3H), 1.58 (m, 2H), 0.95 (t, 3H). MS (DCI/NH$_3$) m/e 256 (M+H)$^+$.

Using the amine prepared above and the procedures described in Example 51B, the title compound was prepared. $^1$H NMR (DMSO-d$_6$) δ 7.35 (m, 4H), 7.19 (m, 2H), 7.07 (m, 4H), 6.84 (m, 6H), 4.70, 4.30 (both m, total 4H), 4.00, 3.60 (both m, total 4H), 3.55–3.20, 3.00, 2.83 (envelope, m, m, total 4H), 2.13 (m, total 3H), 1.50 (m, 4H), 0.80 (m, 6H). MS (FAB+) m/e 707 (M+H)$^+$. Anal calcd for C$_{42}$H$_{46}$N$_2$O$_8$: C, 71.37; H, 6.56; N, 3.96. Found: C, 71.11; H, 6.46; N, 3.82.

EXAMPLE 60

(1α,2β,3β,4α)-1,3-Di[N-propyl-N-(4-phenyl-2,3-butadien-1-yl)aminocarbonyl]cyclobutane-2,4-dicarboxylic acid

EXAMPLE 60A

N-Propargyl-2,5-bis(dimethylsilyl)pyrrolidine

Propargylamine (7.6 mL, 6.1 g, 0.11 mol) and triethylamine (34.0 mL, 24.8 g, 0.25 mol) were dissolved in CH$_2$Cl$_2$ (140 mL), then a solution of bis (chlorodimethylsilyl)ethane in CH$_2$Cl$_2$ (50 mL) was added dropwise. After 2 hours, the reaction mixture was washed with 10% aqueous NaH$_2$PO$_4$ and dried over Na$_2$SO$_4$. After filtration and concentration the residue was vacuum distilled at 7.5 mm Hg, 57°–60° C., to give the title compound (5.1 g) as a light yellow oil, which was ~75% pure. $^1$H NMR (CDCl$_3$) δ 3.56 (d, 2H), 2.12 (t, 1H), 0.71 (s, 4H), 0.12 (s, 12H).

EXAMPLE 60B

3-Benzylpropargylamine

The compound resulting from Example 60A (4.35 g of ~75% pure material, ~16.5 mmol) was dissolved in THF (87 mL), cooled to 0° C., then n-butyllithium (16.5 mL of 1.6M hexanes solution) was added dropwise, followed by 1,3-dimethyl-3,4,5,6-tetrahydro-2(1 H)-pyrimidinone (3.20 mL, 3.39 g, 26.5 mmol) and benzyl bromide (3.50 mL, 5.03 g, 29.4 mmol). The reaction was stirred at 0° C. for 3 hours, then 1N HCl was added. After washing with 3×Et$_2$O, the pH was adjusted to 10 with 4N NaOH, then extracted with 4×Et$_2$O. The second set of Et$_2$O layers were combined, dried over Na$_2$SO$_4$, filtered and concentrated to give a residue which was purified by silica gel chromatography eluting with a gradient of 99:1, 98.75:1.25, and 98:2 CHCl$_3$-MeOH to afford 1.41 g (59%) of the title compound as a light brown oil. $^1$H NMR (CDCl$_3$) δ 7.35,7.24 (both m, total 5H), 3.60 (t, 2H), 3.47 (t, 2H), 1.38 (br s, 2H). MS (DCI/NH$_3$) m/e 146 (M+H)$^+$, 163 (M+H+NH$_3$)$^+$.

EXAMPLE 60C

N-(3-Benzylpropargyl)trifluoroacetamide

The compound resulting from Example 60B (403 mg, 2.78 mmol) was dissolved in CH$_2$Cl$_2$ (10 mL), cooled to 0° C., then triethylamine (0.42 mL, 0.31 g, 3.03 mmol) was added followed by trifluoroacetic anhydride (0.40 mL, 0.59 g, 2.82 mmol). The reaction was stirred at 0° C. for 45 min., then EtOAc (50 mL) was added. After washing with 2×1M H$_3$PO$_4$, 2×saturated NaHCO$_3$, and brine, the solution was dried over Na$_2$SO$_4$, filtered and concentrated to give 615 mg (91%) of the title compound as a yellow oil. $^1$H NMR (CDCl$_3$) δ 7.33 (m, 5H), 4.20 (m, 2H), 3.62 (t, 2H); MS (DCI/NH$_3$) m/e 259 (M+H+NH$_3$)$^+$.

EXAMPLE 60D

N-Propyl-N-(4-phenyl-2,3-butadienyl)trifluoroacetamide

A solution of the compound resulting from Example 60C (570 mg, 2.36 mmol) in DMF (7 mL) was added dropwise to a mechanically stirred slurry of 60 % NaH (98 mg, 2.45 mmol) in DMF (3 mL). After adding 1-iodopropane (0.26 mL, 0.46 g, 2.73 mmol), the reaction was stirred at room temperature overnight. The reaction was then warmed to 60° C. for 3.5 hours, partitioned between saturated NH$_4$Cl and Et$_2$O, and extracted with 2×Et$_2$O. The combined Et$_2$O layers were dried over Na$_2$SO$_4$, filtered and concentrated to give a residue which was purified by chromatography eluting with 98:2 hexanes-EtOAc to afford 240 mg (36%) of the title compound as a yellow oil. $^1$H NMR (CDCl$_3$) δ 7.30 (m, 5H), 6.31 (m, 1H), 5.57 (m, 1H), 4.11 (m, 2H), 3.40 (m, 2H), 1.65 (m, 2H), 0.90 (m, 3H). MS (DCI/NH$_3$) m/e 284 (M+H)$^+$, 301 (M+H+NH$_3$)$^+$.

EXAMPLE 60E 1-(4-Phenyl-2,3-butadienyl)amine

To the compound resulting from Example 60D (230 mg, 0.81 mmol) dissolved in MeOH (3 mL) was added a solution of KOH (400 mg, 7.10 mmol) in water (0.8 mL). The reaction was heated under reflux for 45 minutes, cooled to room temperature, and then concentrated. Water was added to the residue, which was then extracted with 3×CH$_2$Cl$_2$. The combined organic extracts were washed with brine, dried over Na$_2$SO$_4$, filtered and concentrated to give 139 mg (90%) of the title compound as a dark brown oil. $^1$H NMR (CDCl$_3$) δ 7.30 (m, 4H), 7.20 (m, 1H), 6.22 (dt, 1H), 5.65 (dd, 1H), 3.39 (dd, 2H), 2.64 (t, 2H), 1.52 (m, 2H), 0.92 (t, 3H). MS (DCI/NH$_3$) m/e 188 (M+H)$^+$.

EXAMPLE 60F (1α,2β,3β,4α)-1,3-Di[N-propyl-N-(4-phenyl-2,3-butadien-1-yl)aminocarbonyl]cyclobutane-2,4-dicarboxylic acid Using the compound resulting from Example 60E, the title compound was prepared (as a mixture of two diastereomers) by the method of Example 51B. $^1$H NMR (DMSO-d$_6$) δ 7.40–7.10 (envelope, 10H), 6.40 (m, 2H), 5.75, 5.55 (both m, total 2H), 4.20–2.85 (envelope, 12H), 1.50 (m, 4H), 0.80 (m, 6H). MS (FAB+) (M+H)$^+$ 571. Anal calcd for C$_{34}$H$_{38}$N$_2$O$_6$·1.75 H$_2$O: C, 67.81; H, 6.95; N, 4.65. Found: C, 67.47; H, 6.89; N, 4.59.

EXAMPLE 61

(1α,2β,3β,4α)-1,3-Di{N-propyl-N-(4-phenylbut-2-yn-1-yl) aminocarbonyl}cyclobutane-2,4-dicarboxylic acid

EXAMPLE 61A

N-Propyl-3-benzylpropargylamine

To the compound resulting from Example 60B (1.0 g, 7.0 mmol) dissolved in DMF (15 mL) were added 1-iodopropane (0.68 mL, 1.18 g, 7.0 mmol) and potassium carbonate (2.7 g, 19.5 mmol). After warming to 80° C. for 3.5 hours, the reaction was cooled to room temperature, then water and Et$_2$O were added. The Et$_2$O layer was washed with brine, dried over Na$_2$SO$_4$, filtered, and concentrated to give a residue which was purified by chromatography eluting with EtOAc to afford 320 mg (24%) of the title compound as a yellow oil. $^1$H NMR (CDCl$_3$) δ 7.40–7.20 (envelope, 4H), 3.62 (s, 2H), 3.48 (s, 2H), 2.66 (t, 2H), 1.53 (m, 2H), 0.92 (t, 3H); MS (DCI/NH$_3$) m/e 188 (M+H)$^+$.

EXAMPLE 61B (1α,2β,3β,4α)-1,3-Di{N-propyl-(3-benzylpropargyl) aminocarbonyl}cyclobutane-2,4-dicarboxylic acid Using the compound resulting from Example 61 A, the title compound was prepared by the method of Example 51B. $^1$H NMR (DMSO-d$_6$) δ 7.40–7.10 (envelope, 10H), 4.20, 4.00, 3.88 (all m, total 6H), 3.70–3.05 (envelope, 1 OH), 1.55 (m, 4H), 0.82 (m, 6H). MS (FAB+) m/e 571 (M+H)$^+$. Anal calcd for C$_{34}$H$_{38}$N$_2$O$_6$·1.25 H20: C, 68.84; H, 6.88; N, 4.72. Found: C, 69.16; H, 6.81; N, 4.75.

EXAMPLE 62

(1α,2β,3β,4α)-1,3-Di[N-propyl-N-(4-phenylaminobenzyl) aminocarbonyl]cyclobutane-2,4-dicarboxylic acid

EXAMPLE 62A

N-Phenyl-N'-propionyl-1,4-phenylenediamine

A stirred mixture of 1.84 g (10.0 mmol, 1 eq.) of commercial N-phenyl-1,4-phenylenediamine ( a black solid) and 1.18 g (14.0 mmol, 1.4 eq.) of NaHCO$_3$ in 40 mL of CH$_2$Cl$_2$ was cooled to 0° C. To this suspension was added a solution of 0.96 mL (11.0 mmol, 1.1 eq.) of propionyl chloride in 10 mL of CH$_2$Cl$_2$ dropwise. The ice bath was removed and the mixture stirred for 1 hour and then poured into a seperatory funnel containing 50 mL of each CH$_2$Cl$_2$ and water. The organic phase was separated and extracted with 50 mL of saturated aqueous NaHCO$_3$ solution, dried over MgSO$_4$, filtered and concentrated. The residue was purified by flash column chromatography on silica gel eluting with 1:1 ethyl acetate-hexanes to give 1.79 g (75%) of the product. $^1$H NMR (300MHz, CDCl$_3$) δ 7.41 (d, 2H), 7.21–7.43 (m, 2H), 7.14 (bs, 1H), 6.96–7.07 (m, 4H), 6.90 (t, 1H), 5.66 (bs, 1H), 2.38 (q, 2H), 1.25 (t, 3H). MS (DCI) m/e 258 (M+NH$_4$+), 241 (M+H+).

EXAMPLE 62B

N-Phenyl-N'-propyl-4-phenylenediamine

A stirred solution of 1.5 g (6.2 mmol, 1 eq.) of the compound resulting from Example 62A in 10 mL of dry THF was cooled to 0° C. in an ice bath. To this solution was added 12.5 mL (12.5 mmol, 2 eq.) of a 1.0M solution of LiAlH$_4$ in THF dropwise. The ice bath was removed, and the mixture was stirred at ambient temperature for 24 hours. The heterogeneous mixture was cooled to 0° C. and quenched by the careful addition of 0.5 mL of water in 5 mL of THF followed by the addition of 0.5 mL of 15% aqueous NaOH solution and then an additional 1.5 mL of water. The mixture was then vigorously stirred for 5 minutes. Hexanes (25 mL) and Na$_2$SO$_4$ (2 g) were added and vigorous stirring continued for 20 minutes. The mixture was filtered through celite and the pad washed well with ethyl acetate and the filtrate concentrated. The residue was purified by flash column chromatography on SiO$_2$ eluting with 20% ethyl acetate-hexanes to give 1.26 g (89%) of the title compound as a brown oil. $^1$H NMR (300 MHz, CDCl$_3$) δ 7.18 (m, 2H), 7.01 (m, 2H), 6.82 (m, 2H), 6.77 (m, 1 H, 6.60 (m, 2H), 5.38 (bs, 1H), 3.53 (bs, 1H), 3.08 (t, 2H), 1.64 (hextet, 2H), 1.02 (t, 3H). MS (DCI) m/e 244 (M+NH$_4^+$), 227 (M+H$^+$).

EXAMPLE 62C (1α, 2β,3β,4α)-1,3-Di[N-propyl-N-(4-phenylaminobenzyl)aminocarbonyl]cyclobutane-2,4-dicarboxylic acid To a suspension of 1,2,3,4-cyclobutanetetracarboxlic anhydride (0.48 g, 2.47 mmol, 1 eq) in acetonitrile at 0° C. was added a solution of the amine resulting from Example 62B (1.23 g, 5.43 mmol, 2.2 eq.) in acetonitrile. The cooling bath was removed and the mixture stirred overnight. The resulting suspension was concentrated and partitioned between 3N aqueous HCl and 3 portions of ethyl acetate. The combined organic phases were extracted with brine, dried, filtered and concentrated. The residue was purified by column chromatography on SiO$_2$ eluting with a mixture of CHCl$_3$—CH$_3$OH—AcOH to give 0.25 g (16%) of the title compound and 0.77 g (48%) of the 1,2 isomer. $^1$H NMR (300 MHz, DMSO-d$_6$), δ 12.30 (bs, 2H), 8.32 (s, 2H), 7.26 (t, 4H), 7.11 (m, 12H), 6.87 (t, 2H), 3.64 (m, 2H), 3.51 (m, 2H), 3.27 (m, 3H), 3.09 (m, 2H), 1.37 (sextet, 4H), 0.76 (t, 6H). MS (FAB$^+$) m/e 648 (M$^+$). HRMS Calcd for C$_{38}$H$_{41}$N$_4$O$_6$: 648.2948. Found: 648.2931. Anal calcd for C$_{38}$H$_{40}$N$_4$O$_6$: C, 70.35; H, 6.21; N, 8.63. Found: C, 70.09; H, 6.37; N, 8.52.

EXAMPLE 63

(1α,2β,3β,4α)-1,3-Di[N-propyl-N-(4-phenylaminobenzyl)aminocarbonylcyclobutane-2,4-dicarboxylic acid

EXAMPLE 63A

4-Phenylaminobenzoic acid N-propylamide

To a stirred solution of 1.06 g (5.0 mmol, 1 eq.) of 4-phenylaminobenzoic acid, prepared by the method of Portnaya, et al., Zhur. Obshchei. Khim., 30: 2693 (1960), n-propylamine (0.82 mL, 10.0 mmol, 2 eq.) and 0.061 g (0.5 mmol, 0.1 eq.) of DMAP in THF at 0° C. was added 1.05 g (5.5 mmol, 1.1 eq.) of EDCl. The mixture was stirred overnight while the bath melted. The mixture was poured into 150 mL of ethyl acetate and extracted with 50 mL each of water, 1N aqueous HCl, water, and saturated aqueous NaHCO$_3$ solution. The ethyl acetate layer was then dried over Na$_2$SO$_4$, filtered and concentrated. The residue was purified by flash column chromatography on SiO$_2$ eluting with 1:1 ethyl acetate-hexanes to give 0.51 g (40%) of the title compound. $^1$H NMR (300 MHz, CDCl$_3$) δ 10.57 (bs, 2H), 7.21–7.41 (m, 9H), 3.96 (s, 2H), 2.75 (m, 2H), 1.64 (hextet, 2H), 0.92 (t, 3H). MS (DCI) m/e 255 (M+H)$^+$.

EXAMPLE 63b

N-Propyl-N-(4-phenylaminobenzyl) amine

To a stirred solution of 0.50 g (1.96 mmol, 1 eq.) of the compound resulting from Example 63A in 10 mL of dry THF at 0° C. was added 3.9 mL (3.9 mmol, 2 eq.) of a 1.0M solution of LiAlH$_4$ in THF. The ice bath was removed and stirring continued for 30 minutes. The solution was then brought to reflux for 20 hours and then cooled back to 0° C. The mixture was carefully quenched by the addition of 0.15 mL of water, 0.15 mL of 15% aqueous NaOH solution, and 0.45 mL of water and vigorously stirred for 10 minutes. Ethyl ether (20 mL) and MgSO$_4$ (2 g) were added and stirring continued for an additional 15 minutes. The heterogeneous mixture was filtered through a pad of SiO$_2$ (wetted with ether) and the pad was then washed with 100 mL of ether followed by 100 mL of 5% CH$_3$OH—CHCl$_3$. The filtrate was concentrated to give 0.398 g (85%) of the title compound as a yellow oil that was used without further purification. $^1$H NMR (300 MHz CDCl$_3$) δ 7.19–7.32 (m, 2H), 7.01–7.08 (m, 2H), 6.87–6.93 (m, 1H), 5.67 (bs, 1H), 3.72 (s, 2H), 2.61 (t, 2H), 1.53 (hextet, 2H), 1.39 (bs, 1H), 0.92 (t, 3H). MS (DOl) m/e 241, 182.

EXAMPLE 63C (1α,2β,3β,4α)-1,3-Di[N-propyl-N-(4-phenylaminobenzyl)aminocarbonylcyclobutane-2,4-dicarboxylic acid Following the procedures described in Example 62C, the compound resulting from Example 63B (0.378 g, 1.57 mmol, 2.2 eq.) and 0.140 g (0.71 mmol, 1 eq.) of 1,2,3,4-cyclobutanetetracarboxylic dianhydride were reacted to give 0.128 g (27%) of the title compound. $^1$H NMR (300 MHz, CDCl$_3$) δ 7.14–7.30 (m, 8H), 6.83–7.10 (m, 12H), 3.84–4.85 (m, 8H), 2.94–3.56 (m, 4H), 1.37–1.62 (m, 4H), 0.72–0.88 (m, 6H). MS (FAB$^+$) m/e 677 (M+H)$^+$. HRMS Calcd for C$_{40}$H$_{45}$N$_4$O$_6$ (M+H)$^+$ 677.3339; Found: 677.3331. Anal calcd for C$_{40}$H$_{45}$N$_4$O$_6$: C, 70.99; H, 6.55; N, 8.28. Found: C, 70.22; H, 6.57; N, 8.00.

EXAMPLE 64

(1α,2β,3β,4α)-1,3-Di[N-propyl-N-(4-phenylthiobenzyl)aminocarbonylcyclobutane-2,4-dicarboxylic acid

EXAMPLE 64A

N-Propyl-N-(4-phenylthiobenzyl) amine

To a stirred solution of 2.14 g (10 mmol, 1.0 eq.) of 4-phenylthiobenzaldehyde, prepared by the method of Sivasubramanian, S. and Ravichandran, K., Ind. J. Chem., 30b: 1148 (1991), and 0.6 mL (10.0 mmol, 1.0 eq.) of acetic acid in 40 mL of CH$_3$OH at 0° C. was added 1.6 mL (20.0 mmol, 2.0 eq.) of n-propylamine. After stirring 30 minutes at 0° C., NaCNBH$_3$ (0.69 g, 11 mmol, 1.1 eq.) was added, and the mixture was stirred for an additional 2 hours whereupon an additional 0.69 g of NaCNBH$_3$ was added. The reaction mixture was stirred an additional 14 hours and then poured into 200 mL of saturated NaHCO$_3$ solution and extracted with 3×50 mL of ethyl acetate. The combined organic phases were extracted with brine, dried (MgSO$_4$), filtered and concentrated. Purification of the residue by column chromatography on SiO$_2$ eluting with 10% CH$_3$OH—CHCl$_3$ containing a trace of AcOH gave 1.59 g (62%) of the title compound as a light yellow oil. Spectral analysis indicated the presence of ~1 eq. of AcOH. $^1$H NMR (300 MHz, CDCl$_3$) δ 7.54 (bs, 1H (AcOH); 7.21–7.37, m, 9H), 3.83 (s, 2H), 2.64 (t, 2H), 1.98 (s, 3H (AcOH), 1.60 (hextet, 2H), 0.92 (t, 3H). MS (DCI) m/e 258 (M+H)$^+$.

EXAMPLE 64B (1α,2β,3β,4α)-1,3-Di[N-propyl-N-(4-phenylthiobenzyl)aminocarbonylcyclobutane-2,4-dicarboxylic acid Following the procedures described in Example 62C, the compound resulting from Example 64A (0.566 g, 2.2 mmol, 2.2 eq.) and 0.196 g (1.0 mmol, 1.0 eq.) of 1,2,3,4-cyclobutanetetracarboxylic dianhydride were reacted to give 0.193 g (27%) of the title compound as an off white foam. $^1$H NMR (300 MHz, CDCl$_3$) δ 7.02–7.37 (m, 18H), 4.08–4.70 (m, 6H), 3.6–3.91 (m, 2H), 3.39 (m, 1H), 2.98–3.30 (m, 3H), 1.53 (m, 4H), 0.82 (m, 6H). MS (FAB$^+$) m/e 711 (M+H)$^+$. HRMS calcd for C$_{40}$H$_{43}$N$_2$O$_6$S$_2$ (M+H)$^+$ 711.2563. Found: 711.2546. Anal calcd for C$_{40}$H$_{42}$N$_2$O$_6$S$_2$: C, 67.58; H, 5.95; N, 3.94. Found: C, 67.31; H, 5.82; N, 3.76.

EXAMPLE 65

(1α,2β,3β,4α)-1,3-Di[N-propyl-N-(4-phenoxymethylbenzyl)aminocarbonyl]-2,4-cyclobutanedicarboxylic acid

EXAMPLE 65A

Methyl-4-phenoxymethylbenzoate

To a stirred mixture of 5.72 g (25.0 mmol, 1.0 eq.) of methyl-4-bromomethylbenzoate and 3.80 g (27.5 mmol, 1.1 eq.) of K$_2$CO$_3$ in 10 mL of DMF at ambient temperature was added a solution of 2.59 g (27.5 mmol, 1.1 eq.) of phenol in 10 mL of DMF dropwise, and the mixture stirred overnight. The reaction mixture was poured into 100 mL of water and extracted with 3×100 mL portions of 25% CH$_2$Cl$_2$-hexanes. The combined organic phases were washed with 3×100 mL portions of water, dried (MgSO$_4$), filtered and concentrated. The solid residue was recrystallized from ~50 mL of hexanes to give 5.31 g (88%) of the title compound as a white, crystalline solid. $^1$H NMR (300 MHz, CDCl$_3$) δ 8.05 (d, 2H), 7.51 (d, 2H), 7.26–7.33 (m, 2H), 6.95–7.02 (m, 3H), 5.13 (s, 2H), 3.92 (s, 3H). MS (DCI) m/e 260 (M+NH$_4$)$^+$.

EXAMPLE 65B

4-Phenoxymethylbenzoic acid

To a suspension of 2.42 g (10 mmol, 1.0 eq.) of the compound resulting from Example 65A in 20 mL of CH$_3$OH at 0° C. was added a solution of 0.97 g (15.0 mmol, 1.5 eq.) of KOH (87%) in 10 mL of CH$_3$OH. The suspension was allowed to reach ambient temperature overnight whereupon 5 mL of water was added. After stirring was continued for 3 additional hours, the mixture was poured into 200 mL of water and extracted with 3×50 mL of diethyl ether. The aqueous phase was acidified with 3N aqueous HCl and the resulting precipitate collected by filtration. Purification by recrystallization from acetone-CH$_3$OH gave 0.60 g (28%) of the title compound as a white, crystalline solid. $^1$H NMR (300 MHz, CDCl$_3$) δ 8.12 (d, 2H), 7.56 (d, 2H), 7.22–7.36 (m, 3H), 6.94–7.01 (m, 2H), 5.15 (s, 2H). MS (DCI) m/e 246 (M+NH$_4$)$^+$.

EXAMPLE 65C

N-Propyl-4-phenoxymethylbenzamide

To a stirred solution of 0.59 g (2.78 mmol, 1.0 eq.) of the compound resulting from Example 65B in 10 mL of THF at room temperature was added 0.495 g (3.05 mmol, 1.1 eq.) of 1,1'-carbonyldiimidazole. After the initial evolution of CO$_2$ was complete, the mixture was heated to reflux for 30 minutes and subsequently cooled to ambient temperature with a ice/water bath. The resulting nearly colorless solution was treated with 0.68 mL (8.33 mmol, 3.0 eq.) of n-propylamine and stirring was continued overnight. The reaction mixture was then partitioned between water (50 mL) and ethyl acetate (100 mL). The layers were separated, and the aqueous phase was extracted with an additional 50 mL portion of ethyl acetate. The combined organic phases were then washed with 50 mL each of water, saturated NaHCO$_3$ solution and brine, dried (MgSO$_4$), filtered and concentrated. The solid residue was purified by recrystallization form ethyl acetate to give 0.418 g (59%) of the title compound as a white solid. $^1$H NMR (300 MHz, CDCl$_3$) δ 7.78 (m, 2H), 7.49 (d, 2H), 7.25–7.32 (m, 2H), 6.93–7.00 (m, 3H), 6.17 (bs, 1H), 5.11 (s, 2H), 3.42 (m, 2H), 1.62 (hextet, 2H), 0.98 (t, 3H). MS (DCI) m/e 287 (M+NH$_4$)$^+$.

EXAMPLE 65D

N-Propyl-N-(4-phenoxymethylbenzyl)amine hydrochloride

To a stirred solution of 0.400 g (1.58 mmol, 1.0 eq.) of the compound resulting from Example 65C in 2 mL of dry THF at 0° C. was added 3.16 mL (3.16 mmol, 2 eq.) of a 1.0M solution of LiAlH$_4$ in THF dropwise. The ice bath was removed and the mixture heated to reflux for 18 hours. After cooling to 0° C., the excess hydride was carefully quenched by the sequential addition of 0.12 mL of water in 1 mL of THF, 0.12 mL of 15% aqueous NaOH solution and 0.36 mL of water. The resulting suspension was vigorously stirred for 10 minutes followed by the addition of ether (15 mL) and MgSO$_4$ (2 g) and the vigorous stirring continued for an additional 15 minutes. The reaction mixture was filtered through a pad of SiO$_2$ (pre-wetted with ether) and the pad was washed well with ethyl acetate. The filtrate was concentrated to dryness and the residue dissolved in THF and treated with a slight excess of aqueous HCl. The solution was concentrated to dryness again (using toluene to remove the excess water). The solid residue was purified by recrystallization from methanol-acetone to give 0.314 g (72%) of the title compound as a white crystalline solid. $^1$H NMR (300 MHz, CD$_3$OD) δ 7.52 (q, 4H), 7.25 (m, 2H), 6.89–7.00 (m, 3H), 5.13 (s, 2H), 4.20 (s, 2H), 3.01 (m, 2H), 1.72 (m, 2H), 1.02 (t, 3H).

EXAMPLE 65E (1α,2β,3β,4α)-1,3-Di[N-propyl-N-(4-phenoxymethylbenzyl)aminocarbonyl]-2,4-cyclobutanedicarboxylic acid To a stirred suspension of 0.098 g (0.5 mmol, 1.0 eq.) of 1,2,3,4-cyclobutanetetracarboxylic dianhydride in 3 mL of acetonitrile at 0° C. was added 0.15 mL (1.05 mmol, 2.1 eq.) of $Et_3N$. After 15 minutes the compound resulting from Example 65D (0.276 g, 1.0 mmol, 2.0 eq.) was added and the mixture allowed to reach room temperature and stirring continued for 66 hours. The reaction mixture was poured into 20 mL of 4N aqueous $H_2SO_4$ and extracted with 3×20 mL of ethyl acetate. The combined organic phases were washed with water and brine, dried ($MgSO_4$), filtered and concentrated. The residue was purified by column chromatography on $SiO_2$ eluting with 94:5:1 $CHCl_3$—$CH_3OH$—acetic acid to give the title compound (0.100 g, 28%) followed by the 1,2 isomer. (0.093 g, 26%) as a white foam. $^1H$ NMR ($CDCl_3$), δ 7.21–7.44 (m, 12H), 6.92–7.02 (m, 6H), 5.05 (m, 4H), 4.68–4.88 (m, 2H), 4.12–4.48 (m, 4H), 3.69–3.89 (m, 2H), 3.51 (m, 1H), 2.66–3.38 (m, 3H), 1.59 (m, 4H), 0.86 (m, 6H). MS ($FAB^-$) m/e 705, ($FAB^+$) 707. HRMS (FAB) Calcd for $C_{42}H_{47}N_2O_8$ ($M+H^+$) 707.3332. Found: 707.3314. Anal calcd for $C_{42}H_{46}N_2O_8$: C, 71.37; H, 6.56; N, 3.96. Found: C, 71.03; H, 6.68; N, 3.85.

EXAMPLE 66

(1α,2β,3β,4α)-1,3-Di[N-propyl-N-(4-phenoxyphenyl)aminocarbonyl]cyclobutane-2,4-dicarboxylic acid

EXAMPLE 66A

N-(4-Phenoxy)phenylpropionamide

To a solution of 4-phenoxyaniline (4.62 g, 25 mmol) in methylene chloride (50 mL and pyridine (10 mL) was added propionyl chloride (3.3 mL, 37.5 mmol). After 1 hour, the reaction mixture was diluted with ether (150 mL), washed with water (50 mL), 10% sodium carbonate solution (50 mL), 10% HCl (50 mL), saturated copper sulfate (50 mL), water (50 mL) and brine (30 mL), dried over anhydrous magnesium sulfate, filtered, and concentrated. The crude amide was used without further purification. $^1H$ NMR (300 MHz, $CDCl_3$) δ 7.49 (d, 2 H), 7.31 (t, 2 H), 7.11–6.95 (m, 5 H), 2.40 (q, 2 H), 1.25 (t, 3 H).

EXAMPLE 66B

N-Ethyl-(4-phenoxy)aniline

To a solution of the compound resulting from Example 66A in THF (30 mL) was added lithium aluminum hydride (1.0M in THF, 20 mL). After 14 hours, the reaction was cooled using an ice bath, and water (0.80 mL), 15% NaOH (0.80 mL) and water (2.4 mL) were carefully added sequentially. The resulting milky mixture was filtered through celite, washed with ether, and concentrated to give the title compound (5.16 g, 91% for steps A and B) in good purity. $^1H$ NMR (300 MHz, $CDCl_3$) δ 7.28 (m, 2 H), 6.99 (t, 1 H), 6.92 (m, 4 H), 6.60 (d, 2 H), 3.55 (bs, 1 H), 3.06 (t, 2 H), 1.65 (sextet, 2 H), 1.01 (t, 3 H).

EXAMPLE 66C (1α,2β,3β,4α)-1,3-Di[N-propyl-N-(4-phenoxyphenyl)aminocarbonyl]cyclobutane-2,4-dicarboxylic acid A mixture of the compound resulting from Example 66B (0.908 g, 4.0 mmol), 1,2,3,4-cyclobutanetetracarboxylic dianhydride (0.314 g, 1.6 mmol), triethylamine (0.69 mL, 4.8 mmol) and DMAP (20 mg) in acetonitrile (10 mL) were stirred overnight. The resulting reaction mixture was concentrated and partitioned between 20% aqueous HCl and 3 portions of ethyl acetate. The combined organic phases were washed with brine, dried over magnesium sulfate, filtered and concentrated. The residue was purified by column with 1:1 $CHCl_3$—EtOAc, followed by 50:50:2:1 $CHCl_3$—EtOAc—MeOH—AcOH to give the title compound as the first fraction (0.372 g, 36%) and its regio-isomer as the second fraction (0.514 g, 49%). $^1H$ NMR (500 MHz, DMSO-$d_6$), δ 12.39 (br.s., 2 H), 7.44 (t, 4 H), 7.29 (d, 4 H), 7.18 (t, 2 H), 7.09 (d, 4 H), 7.06 (d, 4 H), 3.66 (m, 2 H), 3.47 9dd, 2 H), 3.32 (m, 2 H), 3.10 (dd, 2 H), 1.37 (m, 4 H), 0.78 (t, 6 H). MS ($FAB^+$) m/e 651 ($M+H$)$^+$.

EXAMPLE 67

(1α,2β,3β,4α)-1,3-Di[N-propyl-N-(2-(4-phenoxyphenyl)ethyl)aminocarbonyl]cyclobutane-2,4-dicarboxylic acid

EXAMPLE 67A

4-Phenoxystyrene

To a suspension of methyltriphenylphosphium bromide (7.85 g, 22 mmol) in THF (10 mL) was added potassium tert-butoxide (1.0M solution in THF, 22 mL). After 30 minutes, 4-phenoxybenzaldehyde (3.96 g, 20 mmol) was added to the above mixture. The reaction was diluted with equal volume of hexane after 20 minutes and filtered through silica gel. The residue was rinsed and washed with 20% ether in hexane. Concentration of the filtrate gave the crude product as an off white solid which was used without further purification.

EXAMPLE 67B 2-(4-Phenoxyphenyl)ethyl alcohol

To the compound resulting from Example 67A in THF (40 mL) was added borane-methyl sulfide solution (10M, 1.6 mL, 16 mmol). After 3 hours, the reaction was cooled with an ice-water bath, and anhydrous ethanol (5 mL) was added carefully to destroy excess borane. Aqueous 15% sodium hydroxide solution (4 mL) was added, followed by 30% hydrogen peroxide (4 mL). The resulting mixture was refluxed for 1 hour, cooled to room temperature, then extracted with ether (80 mL). The organic phase was then washed with water (20 mL×2) and brine (20 mL), dried with anhydrous magnesium sulfate, filtered, and concentrated. The residue was then purified by column chromatography eluting with 20% ethyl acetate in hexane, followed by 100% ether to give the title compound as the second fraction (2.32 g, 54%, for steps A and B). $^1H$ NMR (300 MHz, $CDCl_3$) δ 7.37–6.94 (m, 9 H), 3.87 (q, 2 H), 2.86 (t, 2 H), 1.37 (t, 1 H).

EXAMPLE 67C

4-(2-Chloroethyl)phenyl phenyl ether

To a −78° C. solution of the compound resulting from Example 67B (3.64 g, 17.0 mmol) in anhydrous methylene chloride (40 mL) was slowly added phosphorus trichloride (2.61 g, 19.0 mmol). The cold bath was then removed, and the reaction was allowed to warm to room temperature over 1 hour. The reaction mixture was then slowly poured into an ice-cooled solution of saturated sodium bicarbonate (50 mL) and extracted with ether (100 mL). The organic phase was washed with water (30 mL×2) and brine (20 mL), dried over anhydrous magnesium sulfate, filtered through silica gel, and concentrated. The crude product was used for next step without further purification. $^1$H NMR (300 MHz, CDCl$_3$) δ 7.72–6.93 (m, 9 H), 3.56 (t, 2 H), 3.15 (t, 2 H).

EXAMPLE 67D

2-(4-Phenoxyphenyl)ethylphthalimide

A solution of the crude compound resulting from Example 67C and potassium phthalimide (3.78 g, 20.4 mmol) in THF (40 mL) was refluxed for 16 hours and then concentrated to near dryness. The residue was triturated with 1:1 ether-hexane (5 mL), and the resulting solid was filtered and air dried. The crude product was used directly for the next step. $^1$H NMR (300 MHz, CDCl$_3$) δ 7.85 (m, 2 H), 7.72 (m, 2 H), 7.33–6.92 (m, 9 H), 3.92 (t, 2 H), 2.98 (t, 2 H).

EXAMPLE 67E

2-(4-Phenoxyphenyl)ethylamine

The suspension of the crude compound resulting from Example 67D in ethanol (20 mL) was refluxed with hydrazine (0.65 mL, 20.4 mmol). The reaction mixture became homogeneous after about 10 minutes, and white precipitate started to form shortly thereafter. After 16 hours of refluxing, the reaction mixture was cooled to room temperature, filtered, and washed with ethanol (5 mL×3). The filtrate was diluted with ether (100 mL), washed with 10% sodium carbonate (20 mL), water (30 mL) and brine (20 mL), dried over anhydrous potassium carbonate, filtered and concentrated. The crude amine was used directly for the next step. $^1$H NMR (300 MHz, CDCl$_3$) δ 7.35–6.94 (m, 9 H), 2.98 (t, 2 H), 2.72 (t, 2H).

EXAMPLE 67F

N-(2-(4-Phenoxyphenyl)ethyl)propionamide

To the solution of crude amine resulting from Example 67E in methylene chloride (20 mL) and pyridine (5 mL) was added propionyl chloride (3.0 mL, 34 mmol). After 6 hours, the reaction was diluted with ethyl acetate (80 mL), washed with water (20 mL), 10% aqueous hydrochloric acid (20 mL), water (20 mL), saturated copper sulfate (20 mL) and brine (20 mL), dried over anhydrous magnesium sulfate, filtered, and concentrated. The residue was purified by column chromatography eluting with 50% ethyl acetate in hexane to give the desired product (1.23 g, 27% for the last 4 steps). $^1$H NMR (300 MHz, CDCl$_3$) δ 7.36–6.95 (m, 9 H), 5.46 (bs, 1 H), 3.51 (q, 2 H), 2.80 (t, 2 H), 2.19 (q, 2 H), 1.15 (t, 3 H).

EXAMPLE 67G

N-Propyl-N-[2-(4-phenoxy)phenyl]ethylamine

To a solution of the compound resulting from Example 67F (1.23 g, 4.57 mmol) in THF (10 mL) was slowly added lithium aluminum hydride (1.0M in THF, 4.6 mL). After the resulting mixture was refluxed for 3 hours, it was cooled to 0° C., and water (0.18 mL), 15% aqeous NaOH (0.18 mL), and water (0.54 mL) were carefully added sequentially. White precipitate formed, and the mixture was filtered through celite, washed with ether, and concentrated. The crude amine (1.05 g, 88%) obtained in this manner was in good purity as judged by NMR. $^1$H NMR (300 MHz, CDCl$_3$) δ 7.35–6.92 (m, 9 H), 3.30 (bs, 1 H), 2.83 (m, 2 H), 2.60 (t, 2 H), 2.37 (dd, 2 H), 1.49 (m, 2 H), 0.92 (t, 3 H).

EXAMPLE 67H

(1α,2β,3β,4α)-1,3-Di[N-propyl-N-(2-(4-phenoxyphenyl)ethylaminocarbonyl]cyclobutane-2,4-dicarboxylic acid A mixture of the compound resulting from Example 67G (0.942 g, 3.69 mmol), 1,2,3,4-cyclobutanetetracarboxylic dianhydride (0.290 g, 1.48 mmol), triethylamine (0.62 mL, 4.4 mmol), DMAP (50 mg) in acetonitrile (10 mL) were combined according to the procedures described in Example 66C to give the title compound as the first fraction (0.436 g, 42%) and its regio-isomer as the second fraction (0.477 g, 46%). $^1$H NMR (500 MHz, DMSO), δ 7.40–6.91 (m, 18 H), 3.88–2.64 (m, 16 H), 1.63–1.41 (m, 4 H), 0.88–0.77 (m, 6 H). MS (FAB$^+$)m/e 707 (M+H)$^+$.

EXAMPLE 68

(1α,2β,3β,4α)-1,3-Di[N-(2-methoxyethyl)-N-(4-phenoxybenzyl)aminocarbonyl]cyclobutane-2,4-dicarboxylic acid

EXAMPLE 68A

N-(2-Methoxymethyl-N-(4-phenoxybenzyl)amine

A mixture of 4-phenoxybenzaldehyde (1.98 g, 10 mmol) and 2-methoxyethylamine (0.751 g, 10 mmol) in ethanol (10 mL) was stirred for 1 hour. Acetic acid (1 mL) and sodium cyanoborohydride (1M in THF, 10 mL) were added, and the reaction was stirred for 14 hours. The reaction was then partitioned between ether and 10% aqueous sodium hydroxide solution. The organic layer was further washed with water and brine, dried over anhydrous potassium carbonate, filtered and concentrated. The title compound was pure as judged by NMR and was used for next step without further purification. $^1$H NMR (300 MHz, CDCl$_3$) δ 7.30 (m, 4 H), 7.09 (t, 1 H), 6.98 (m, 4 H), 3.80 (s, 2 H), 3.51 (t, 2 H), 3.37 (s, 3 H), 2.51 (t, 2 H).

EXAMPLE 68B

(1α,2β,3β,4α)-1,3-Di[N-(2-methoxyethyl)-N-(4-phenoxybenzyl)aminocarbonyl]cyclobutane-2,4-dicarboxylic acid A mixture of the compound resulting from Example 68A (1.38 g, 5.36 mmol), 1,2,3,4-cyclobutanetetracarboxylic dianhydride (0.421 g, 2.15 mmol), triethylamine (0.90 mL, 6.5 mmol) and DMAP (50 mg) in acetonitrile (15 mL) were combined according to the procedures described in Example 66C to give the title compound as the first fraction (0.468 g, 31%) and its regio-isomer as the second fraction (0.807 g, 53%) ¹H NMR (500 MHz, DMSO) δ 7.40–6.97 (m, 18 H), 4.88–4.66 (m, 2 H), 4.45–4.27 (4 s's, 2 H), 4.13–3.90 (m, 2 H), 3.67–3.48 (m, 4 H), 3.47–3.30 (m, 4 H), 3.18–3.12 (4 s's, 6 H), 3.20–3.05 (m, 2 H). MS (FAB⁺) m/e (M+H)⁺.

EXAMPLE 69

(1α,2β,3β,4α)-1,3-Di[N-(2-methylthioethyl)-N-(4-phenoxybenzyl)aminocarbonyl]cyclobutane-2,4-dicarboxylic acid

EXAMPLE 69A

N-(2-Methylthioethyl)-N-(4-phenoxybenzyl)amine

Following the procedure described in Example 68A, 4-phenoxybenzaldehyde (1.98 g, 10 mmol) and 2-methylthioethylamine (0.912 g, 10 mmol) were combined to give the title compound (2.53 g, 93%) ¹H NMR (300 MHz, CDCl₃) δ 7.32 (m, 4 H), 7.09. (t, 1 H), 6.97 (m, 4 H), 3.80 (s, 2 H), 2.84 9t, 2 H), 2.68 (t, 2 H), 2.10 (s, 3 H).

EXAMPLE 69B (1α,2β,3β,4α)-1,3-Di[N-{2-methylthioethyl)-N-(4-phenoxybenzyl)aminocarbonyl]cyclobutane-2,4-dicarboxylic acid A mixture of the compound resulting from Example 69A (0.682 g, 2.5 mmol), 1,2,3,4-cyclobutanetetracarboxylic dianhydride (0.196 g, 1.0 mmol), triethylamine (0.42 mL, 3.0 mmol) and DMAP (12 mg) in acetonitrile (10 mL) were combined according to the procedures described in Example 66C to give the title compound as the first fraction (0.214 g, 29%) and its regio-isomer as the second fraction (0.274 g, 37%). ¹H NMR (500 MHz, CDCl₃) δ 7.30–6.85 (m, 18 H), 4.79–4.63 (m, 2 H) 4.40–4.08 (m, 4 H), 3.86–3.48 (m, 2 H), 3.37–3.10 (m, 4 H), 2.53 (m, 4 H), 2.02 (4 s's, 6 H). MS (FAB⁺) m/e 743 (M+H)⁺.

EXAMPLE 70

(1α,2β,3β,4α)-1,3-Di[N-(2-ethylthioethyl)-N-(4-phenoxybenzyl)aminocarbonyl]cyclobutane-2,4-dicarboxylic acid

EXAMPLE 70A

N-(2-Ethylthioethyl)-N-(4-phenoxybenzyl)amine

Following the procedure described in Example 68A, 4-phenoxybenzaldehyde (1.98 g, 10 mmol) and 2-(ethylthio) ethylamine hydrogen chloride (1.42 g, 10 mmol) were combined to give the title compound (2.72 g, 95%). ¹H NMR (300 MHz, CDCl₃), δ 7.33 (m, 4 H), 7.09 (t, 1 H), 6.98 (m, 4 H), 3.78 (s, 2 H), 2.84 (t, 2 H), 2.71 (t, 2 H), 2.54 (q, 2 H), 1.26 (t, 3 H).

EXAMPLE 70B (1α,2β,3β,4α)-1,3-Di[N-(2-ethylthioethyl)-N-(4-phenoxybenzyl)aminocarbonyl]cyclobutane-2,4-dicarboxylic acid A mixture of the compound resulting from Example 70A (0.718 g, 2.5 mmol), 1,2,3,4-cyclobutanetetracarboxylic dianhydride (0.196 g, 1.0 mmol), triethylamine (0.42 mL, 3.0 mmol) and DMAP (24 mg) in acetonitrile (10 mL) were combined according to the procedures described in Example 66C to give the title compound as the first fraction (0.207 g, 27%) and its regio-isomer as the second fraction (0.398 g, 52%). ¹H NMR (500 MHz, CDCl₃) δ 7.36–6.91 (m, 18 H), 4.73–4.43 (m, 4 H),4.35–4.20 (m, 2 H), 3.98–3.31 (m, 6 H), 2.62 (m, 4 H), 2.46 (m, 4 H), 1.18 (m, 6 H). MS (FAB⁺) m/e 771 (M+H)⁺.

EXAMPLE 71

(1α,2β,3β,4α)-1,3-Di[N-(2-benzylthioethyl)-N-(4-phenoxybenzyl)aminocarbonyl]cyclobutane-2,4-dicarboxylic acid

EXAMPLE 71A

N-(2-Benzylthio)ethyl-N-(4-phenoxy)benzylamine

A suspension of 2-aminoethanethiol hydrochloride (2.27 g, 20.0 mmol), benzyl chloride (2.42 mL, 21.0 mmol) and cesium carbonate (19.5 g, 60 mmol) in DMF (100 mL) was stirred overnight. The reaction mixture was then diluted with ethyl acetate (200 mL) and filtered into a separation funnel. The solid residue was washed with ether (50 mL×3). The combined filtrates were then washed with water (80 mL×5) and brine (50 mL), dried over potassium carbonate and filtered. The filtrate was concentrated first with rotary evaporator (water bath at 80° C.), then by high vacuum (1 mm Hg) to give 2-benzylthioethylamine in good purity. The crude product was used for next step without further purification.

Following the procedure described in Example 68A, 4-phenoxybenzaldehyde (4.16 g, 21.0 mmol) and 2-benzylthioethylamine (crude product from the above reaction, 20.0 mmol) were combined to give the title compound (4.82 g, 69.0% for two steps). ¹H NMR (300 MHz, CDCl₃) δ 7.40–7.20 (m, 9 H), 7.09 (t, 1 H), 6.97 (m, 4 H), 4.57 (dt, 2 H), 3.73 (s, 2 H), 3.70 (s, 2 H), 2.77 (t, 2 H), 2.61 (t, 2 H).

EXAMPLE 71B (1α,2β,3β,4α)-1,3-Di[N-(2-benzylthioethyl}-N-(4-phenoxybenzyl)aminocarbonyl]cyclobutane-2,4-dicarboxylic acid A mixture of the compound resulting from Example 71A (4.36 g, 12.5 mmol), 1,2,3,4-cyclobutanetetracarboxylic dianhydride (0.980 g, 5.0 mmol), triethylamine (2.1 mL, 15.0 mmol) and DMAP (100 mg) in acetonitrile (10 mL) were combined according to the procedures described in Example 66C to give the title compound as the first fraction (0.95 g, 21%) and its regio-isomer as the second fraction (1.71 g, 38%). ¹H NMR (500 MHz, DMSO), δ 7.39–6.92 (m, 28 H), 4.82–4.63 (m, 2 H), 4.39–4.27 (m, 2 H), 4.13–3.92 (m, 2 H), 3.98–3.45 (m, 8 H), 3.25 (m, 1 H), 3.10 (m, 1 H), 2.70–2.48 (m, 4 H). MS (FAB⁺) m/e 895 (M+H)⁺.

EXAMPLE 72

(1α,2β,3β,4α)-1,3-Di[N-(furan-2-ylmethyl)-N-(4-phenoxybenzyl)aminocarbonyl]cyclobutane-2,4-dicarboxylic acid

EXAMPLE 72A

N-(Furan-2-yl)methyl-N-(4-phenoxy)benzylamine

Following the procedure described in Example 68A, 4-phenoxybenzaldehyde (1.98 g, 10 mmol) and furfurylamine (0.971 g, 10 mmol) were combined to give the title compound (2.43 g, 87%). ¹H NMR (300 MHz, CDCl₃) δ 7.30 (m, 5 H), 7.09 (t, 1 H), 6.98 (m, 4 H), 6.34 (m, 1 H), 6.19 (m, 1 H), 3.80 (s, 2 H), 3.77 (s, 2 H).

EXAMPLE 72B (1α,2β,3β,4α)-1,3-Di[N-(furan-2-ylmethyl)-N-(4-phenoxybenzyl)aminocarbonyl]cyclobutane-2,4-dicarboxylic acid A mixture of the compound resulting from Example 72A (0.698 g, 2.5 mmol), 1,2,3,4-cyclobutanetetracarboxylic dianhydride (0.196 g, 1.0 mmol), triethylamine (0.42 mL, 3.0 mmol) and DMAP (12 mg) in acetonitrile (10 mL) were combined according to the procedures described in Example 66C to give the title compound as the first fraction (0.251 g, 34%) and its regio-isomer as the second fraction (0.438 g, 58%). ¹H NMR (500 MHz, CDCl₃+CD₃OD) δ 7.45–6.95 (m, 20 H), 6.34–6.21 (m, 4 H), 4.98–4.87 (m, 2 H), 4.48–4.20 (m, 4 H), 3.90 (m, 1 H), 3.75 (m, 1 H). MS (FAB⁺) m/e 755 (M+H)⁺.

EXAMPLE 73

(1α,2β,3β,4α)-1,3-Di[N-(thien-2-ylmethyl)-N-(4-phenoxybenzyl)aminocarbonyl]cyclobutane-2,4-dicarboxylic acid

EXAMPLE 73A

N-(Thien-2-yl)methyl-N-(4-phenoxy)benzylamine

Following the procedure described in Example 68A, 4-phenoxybenzaldehyde (1.98 g, 10 mmol) and 2-thienylmethylamine (1.13 g, 10 mmol) were combined to give the title compound (2.87 g, 97%). ¹H NMR (300 MHz, CDCl₃), δ 7.35–6.92 (m, 12 H), 4.01 (s, 2 H), 3.81 (s, 2 H).

EXAMPLE 73B (1α,2β,3β,4α)-1,3-Di[N-(thien-2-ylmethyl)-N-(4-phenoxybenzyl)aminocarbonyl]cyclobutane-2,4-dicarboxylic acid A mixture of the compound resulting from Example 73A (0.738 g, 2.5 mmol), 1,2,3,4-cyclobutanetetracarboxylic dianhydride (0.196 g, 1.0 mmol), triethylamine (0.42 mL, 3.0 mmol) and DMAP (12 mg) in acetonitrile (10 mL) were combined according to the procedures described in Example 66C to give the title compound as the first fraction (0.193g, 25%) and its regio-isomer as the second fraction (0.382 g, 49%). ¹H NMR (500 MHz, CDCl₃) δ 7.37–6.86 (m, 24 H), 4.96–4.78 (m, 2 H), 4.77–4.54 (m, 2 H), 4.52–4.21 (m, 6 H), 3.89 (m, 1 H), 3.81 (m, 1 H). MS (FAB⁺) m/e 787 (M+H)⁺.

EXAMPLE 74

(1α,2β,3β,4α)-1,3-Di[N-(2-hydroxyethyl)-N-(4-phenoxybenzyl)aminocarbonyl]cyclobutane-2,4-dicarboxylic acid

EXAMPLE 74A

N-(2-tert-Butyldimethylsiloxy)ethyl-N-(4-phenoxy)benzylamine

Following the procedure described in Example 68A, 4-phenoxybenzaldehyde (1.98 g, 10 mmol) and 2-aminoethyl alcohol (0.641 g, 10.5 mmol) were combined to give crude N-(2-hydroxy)ethyl-N-(4-phenoxy)benzylamine (contaminated with about 25 mol % 2-aminoethyl alcohol). ¹H NMR (300 MHz, CDCl₃) δ 7.30 (m, 4 H), 7.10 (dt, 1 H), 6.98 (m, 4 H), 3.80 (s, 2 H), 3.67 (t, 2 H), 2.83 (t, 2 H).

To a solution of crude N-(2-hydroxy)ethyl-N-(4-phenoxy)benzylamine (0.487 g, 2 mmol) and triethylamine (0.42 mL, 3.0 mmol) in dichloromethane (10 mL) was added tert-butyldimethylsilyl chloride (0.452 g, 3 mmol). After 60 hours, ammonium chloride (half saturated, 10 mL) was added, and the reaction was stirred for another 4 hours. The reaction was then extracted with ether (80 mL), and the organic layer was washed with saturated sodium bicarbonate (15 mL), water (20 mL×2) and brine (20 mL), dried over sodium sulfate, and filtered. The filtrate was concentrated, and the crude product was purified with flash chromagography eluting with 1:1 hexane-ethyl acetate followed by 100% ethyl acetate to give the title compound (413 mg, 57.8%). ¹H NMR (300 MHz, CDCl₃) δ 7.36–7.24 (m, 4 H), 7.11 (m, 1 H), 7.01 (m, 4 H), 3.78 (s, 2 H), 3.65 (t, 2 H), 2.75 (t, 2 H), 0.90 (s, 9 H), 0.06 (s, 6 H).

EXAMPLE 74B (1α,2β,3β,4α)-1,3-Di[N-(2-hydroxyethyl)-N-(4-phenoxybenzyl)aminocarbonyl]cyclobutane-2,4-dicarboxylic acid A solution of the compound resulting from Example 74A (701 mg, 1.96 mmol), 1,2,3,4-cyclobutanetetracarboxylic dianhydride (196 mg, 1.0 mmol), triethylamine (0.42 mL, 3.0 mmol) and DMAP (12 mg) in acetonitrile (10 mL) was stirred overnight. Concentrated hydrofluoric acid (1 mL) was added, and the reaction was stirred for another 1 hour. The reaction was treated with hydrochloric acid (0.5N, 15 mL), and extracted with chloroform (10 mL), 4:1 chloroform-methanol (10 mL×5). The combined extracts were washed with brine, dried over sodium sulfate, and filtered. The residue after concentration of the filtrate was redissolved in methanol-ethyl acetate (10 mL), treated with (trimethylsilyl)diazomethane, and concentrated again. The residue was purified by flash column chromatography to give 0.432 g of a mixture of the 1,2-diamide and 1,3-diamide regioisomers (ratio about 60:40 judging from NMR). The mixture was then refluxed with methanol (10 mL) and LiOH (1.0N in water, 3 mL) overnight. The reaction was concentrated, redissolved in water (10 mL), and washed with ether (10 mL×2). The aqueous layer was acidified with hydrochloric acid (3N, 3 mL), and extracted with ethyl acetate (20 mL×3). The combined ethyl acetate extracts were washed with brine (10 mL), dried over sodium sulfate, and filtered. Concentration of the filtrate gave the title compound as a minor component (about 40%) in the mixture with its 1,3-diamide-2,4-diacid regio-isomer. ¹H NMR of the mixture (500 MHz, DMSO) δ 7.42–6.86 (m), 4.92–4.66 (m), 4.44–4.37 (m from minor isomer), 4.30–4.22 (m from the major isomer), 4.14–4.05 (m from the major isomer), 4.95–4.85 (m from the minor isomer), 3.67–2.90 (m). MS (FAB-) m/e 681 (M–H)⁺.

EXAMPLE 75

(1α,2β,3β,4α)-1,3-Di[N-(2-ethylthioethyl)-N-(4-phenylthiobenzyl)aminocarbonyl]cyclobutane-2,4-dicarboxylic acid Following the procedures described in Example 68A, 4-phenylthiobenzaldehyde (1 mol equiv.) and 2-(ethylthio)ethylamine hydrochloride (1 mol equiv.) are combined to give N-(2-ethylthio)ethyl-N-(4-phenylthio)benzylamine.

A mixture of the amine from above (2.05 mol equiv.), 1,2,3,4-cyclobutanetetracarboxylic dianhydride (1.0 mol equiv.), triethylamine (3 mol equiv) and DMAP (0.1 mol equiv) in acetonitrile are combined according to the procedures described in Example 66C to give the title compound.

EXAMPLE 76

(1α,2β,3β,4α)-1,3-Di[N-(4-phenoxybenzyl)-N-(3-methoxyphenethyl) aminocarbonyl]cyclobutane-2,4-dicarboxylic acid

EXAMPLE 76A

N-(4-Phenoxybenzyl)-N-(3-methoxyphenethyl) amine

A solution of 4-benzoxybenzaldehyde (2.5 g, 12.6 mmol), 3-methoxyphenethylamine (1.9 g, 12.6 mmol), a catalytic amount of p-toluenesulfonic acid monohydrate in absolute ethanol (12 mL) was stirred at 80° C. for 1.5 hours. After cooling to room temperature, $NaBH_4$ (0.49 g, 13.0 mmol) was added in portions. The reaction mixture was stirred at 80° C. for 1 hour, then cooled to room temperature, and the ethanol was removed in vacuo. Water was added to the residue and the mixture was extracted with ethyl acetate. The combined extracts were washed with saturated NaCl, dried over $MgSO_4$, filtered, and the solvent removed in vacuo to afford a colorless oil which was purified by silica gel chromatography eluting with 20% ethyl acetate in hexane saturated with $NH_3$ to afford the title compound (3.2 g, 76%) as a colorless oil. MS (DCl/$NH_3$) m/e 334 (M+H)$^+$. $^1$H NMR (CDCl$_3$, 300 MHz) δ 2.82 (t, 2H), 2.92 (t, 2H), 3.77 (s, 2H), 3.80 (s, 3H), 6.80 (m, 3H), 6.98 (m, 3H), 6.08 (t, 1H), 7.22 (m, 3H), 7.32 (t, 2H).

EXAMPLE 76B (1α,2β,3β,4α)-1,3-Di [N-(4-phenoxybenzyl)-N-(3-methoxyphenethyl) aminocarbonyl]cyclobutane-2,4-dicarboxylic acid A solution of the compound resulting from Example 76A (1.26 g, 3.8 mmol), 1,2,3,4-cyclobutanetetracarboxylic dianhydride (0.38 g, 1.95 mmol), triethylamine (0.053 mL, 3.8 mmol), and $CH_3CN$ (14 mL) was stirred at room temperature for 3 hours. The solvent was removed in vacuo, and the residue was dissolved in ethyl acetate, washed successively with 1N HCl and saturated NaCl, dried over $MgSO_4$, filtered, and evaporated to afford a white foam. The crude product (1.8 g) containing both isomers was purified by silica gel chromatography eluting with 97:2.5:0.5 CHCl$_3$—MeOH—HOAc. The faster running isomer was collected to afford 0.59 g (35%) of the desired product. $^1$H NMR (300 MHz, CDCl$_3$) δ 2.71 (q, 4H), 3.30 (m, 1H), 3.45 (t, 2H), 3.65 (d,1H), 3.72 (m, 1H), 3.72 (s, 6H), 3.85 (q, 1H), 4.16 (m, 4H), 4.38 (m, 3H), 4.65 (dd, 1H), 6.70 (m, 5H), 6.95 (m, 7H), 6.92 (m, 5H), 7.08 (m, 4H), 7.15 (d, 3H), 7.30 (m, 7H). MS (FAB) m/e 863 (M+H)$^+$.

EXAMPLE 77

(1α,2β,3β,4α)-1,3-Di [N-(4-phenoxybenzyl)-N-(3,4-dimethoxyphenethyl) aminocarbonyl]cyclobutane-2,4-dicarboxylic acid Using the procedures described in 76A, but substituting 3,4-dimethoxyphenethylamine for 3-methoxyphenethylamine, provided N-(4-phenoxybenzyl)-N-(3,4-dimethoxyphenethyl)amine. $^1$H NMR (300 MHz, CDCl$_3$) δ 2 78 (t, 2H), 2.90 (t, 2H), 3.78 (s, 2H) 3.88 (s, 3H), 6.78 (m, 3H), 6.98 (t, 4 H), 7.09 (t, 1H), 7.26 (t, 2H), 7.32 (t, 2H). MS (DCl/$NH_3$) m/e 364 (M+H)$^+$.

The amine prepared above was reacted by the procedures described in Example 76B to provide the title compound. $^1$H NMR (300 MHz, CDCl$_3$) δ 2.72 (t, 4H), 3.31 (m, 2 H), 3.45 (m, 2H), 3.68 (m, 2H), 3.70 (m, 12H), 4.15 (m, 3H), 4.3 (m, 2H), 4.5 (d, 1H), 6.70 (m, 6H), 6.92 (m, 7H), 7.11 (m, 6H), 7.30 (m, 5H). MS (FAB) m/e 923 (M+H)$^+$.

EXAMPLE 78

(1α,2β,3β,4α)-1,3-Di [N-(4-phenoxybenzyl)-N-phenethylaminocarbonyl]cyclobutane-2,4-dicarboxylic acid Using the procedures described in Example 76A, but substituting phenethylamine for 3-methoxyphenethylamine, provided N-(4-phenoxybenzyl)-N-phenethylamine. $^1$H NMR (300 MHz, CDCl$_3$) δ 2.85 (t, 2H), 2.93 (t, 2H), 3.80 (s, 2H), 6.98 (m, 4H), 7.10 (t, 1H), 7.30 (m, 9H) MS (DCl/$NH_3$) m/e 304 (M+H)$^+$.

The amine prepared above was reacted by the procedures described in Example 76B to provide the title compound. $^1$H NMR (300 MHz, CDCl$_3$) δ 2.79 (t, 4H), 3.41 (t, 3H), 3.50–3.90 (m, 3H), 4.20 (m, 2H), 4.30 (m, 1H), 4.40 (m, 2H), 4.60 (d, 1H), 6 90 (m, 8H), 7.10 (m, 8H), 7.20 (m, 7H), 7.28 (m, 5H). MS (FAB) m/e 841 (M+K)$^+$.

EXAMPLE 79

(1α,2β,3β,4α)-1,3-Di [N-(4-phenoxybenzyl)-N-(3-phenyl-1-propyl)aminocarbonyl]cyclobutane-2,4-dicarboxylic acid Using the procedures described in Example 76, but substituting 3-phenyl-1-propylamine for 3-methoxyphenethylamine, provided N-(4-phenoxybenzyl)-N-(3-phenyl-1-propyl)amine. $^1$H NMR (300 MHz, CDCl$_3$) δ 1.85 (p, 2H), 2.70 (m, 4H), 3.75 (s, 2H), 7.00 (t, 3H), 7.10 (t, 1H), 7.20 (m, 3H), 7.30 (m, 7H). MS (DCl/$NH_3$) m/e 318 (M+H)$^+$.

The amine prepared above was reacted by the procedures described in Example 76B to provide the title compound. $^1$H NMR (300 MHz, CDCl$_3$) δ 1.80 (q, 4H), 2.50 (t, 4H), 3.20 (t, 3H), 3.40 (m, 1H), 3.72 (m, 2H), 4.20 (m, 2H), 4.30–4.61 (m, 4H), 6.82 (m, 5H), 6.94 (m, 5H), 7.06 (t, 11H), 7.21 (d, 4H), 7.28 (m, 5H). MS (FAB) m/e 831 (M+H)$^+$.

EXAMPLE 80

(1α,2β,3β,4α)-1,3-Di [N-(4-phenoxybenzyl)-N-(4-phenyl-1-butyl)aminocarbonyl]cyclobutane-2,4-dicarboxylic acid Using the procedures described in Example 76A, but substituting N-(4-phenyl-1-butyl)amine for 3-methoxyphenethylamine, provided N-(4-phenoxybenzyl)-N-(4-phenyl-1-butyl)amine. $^1$H NMR (300 MHz, CDCl$_3$) δ 1.50–1.72 (m, 4H), 2.65 (m, 4 H), 3.25 (s, 2H), 6.98 (t, 4H), 7.09 (t, 1H), 7.19 (m, 3H), 7.30 (m, 6H). MS (DCl/$NH_3$) m/e 332 (M+H)$^+$.

The amine prepared above was reacted by the procedures described in Example 76B to provide the title compound. $^1$H NMR (300 MHz, CDCl$_3$), δ 1.55 (s, 6 H), 2.55 (s, 4H), 3.20 (m, 4H), 3.48 (m, 1H), 3.80 (m, 3H), 4.18 (m, 2H), 4.30–4.58(m, 4H), 4.67 (t, 1H), 6.90 (m, 7H), 7.10 (m, 10 H), 7.28 (m, 9H). MS (FAB) m/e 859 (M+H)$^+$.

EXAMPLE 81

(1α,2β,3β,4α)-1,3-Di [N-(4-phenoxybenzyl)-N-(2-methylnaphthyl) aminocarbonyl]cyclobutane-2,4-dicarboxylic acid

EXAMPLE 81A

4-Phenoxybenzyl alcohol

A solution of 4-phenoxybenzaldehyde (10.0 g, 50 mmol) and 10 mL dry THF was added dropwise to a 0° C. suspension of lithium aluminum hydride (2.1 g, 55.3 mmol) and 100 mL dry THF. The reaction mixture was stirred for 1 hour at 0° C., then was quenched successively with 2.1 mL H20, 2.1 mL 10% NaOH, and 6.3 mL $H_2O$. The resultant slurry was stirred for 1.5 hours at room temperature, then was filtered through Celite® and the filtrate was evaporated under reduced pressure to afford the title compound (9.9 g) as a white solid. $^1$HNMR (300 MHz, $CDCl_3$) δ 1.68 (t, 1H), 4.68 (d, 2H), 7.00 (m, 4H), 7.10 (t, 1H), 7.35 (m, 4H). MS ($DCl/NH_3$) m/e 183 (M+1, $-H_2O$)$^+$.

EXAMPLE 81B

4-Phenoxybenzyl phthalimide

The compound resulting from Example 81A (5.0 g, 25 mmol) was added to a solution of lithium bromide (4.4 g, 51 mmol), trimethylsilyl chloride (8.2 mL, 64 mmol), and 51 mL acetonitrile. The reaction mixture was stirred at reflux for 2 hours, then was cooled to room temperature. Water (25 mL) was added, the acetonitrile was removed under reduced pressure, and the aqueous layer was extracted with ether. The combined organic extracts were washed with saturated aqueous sodium bicarbonate and brine, dried ($MgSO_4$), filtered, and the solvent evaporated in vacuo to afford 5.35 g clear oil. The crude bromide (20.3 mmol) was stirred at room temperature for 24 hours with potassium phthalimide (4.2 g, 22.1 mmol) and 45 mL DMF. Water was added, and the mixture was extracted with methylene chloride. The combined organic extracts were washed with water (2×), 1N HCl and brine, dried ($MgSO_4$), filtered, and evaporated under reduced pressure to afford the title compound (7.9 g) as a white solid. $^1$HNMR (300 MHz, $CDCl_3$) δ 4.83 (s, 2H), 6.95 (dd, 4H), 7.10 (t, 1H), 7.31 (t, 2H), 7.42 (d, 2H), 7.71 (2H), 7.88 (m, 2H). MS ($DCl/NH_3$) m/e 347 (m+18)$^+$.

EXAMPLE 81C

N-(4-Phenoxybenzyl)amine

The compound resulting from Example 81B (6.7 g, 20.4 mmol), hydrazine (2.1 mL, 35 wt. % in water) and 130 mL absolute ethanol were stirred at reflux for 4 hours. After cooling to room temperature, the solid present was filtered and air dried briefly. The solid was then partitioned between 1N KOH and methylene chloride. The layers were separated and the aqueous layer was extracted 2 more times with methylene chloride. The combined organic layers were washed with water and brine, dried ($MgSO_4$), filtered, and evaporated in vacuo to afford the title compound (2.7 g) as a clear oil. $^1$HNMR (300 MHz, $CDCl_3$) δ 1.48 (s, 2H), 3.87 (s, 2H), 7.00 (m, 3H), 7.10 (t, 1H), 7.30 (m, 5H). MS ($DCl/NH_3$) m/e 200 (M+H)$^+$, 217 (M+$NH_4$)$^+$.

EXAMPLE 81D

N-(4-Phenoxybenzyl)-N-(2-naphthoyl)amine

A soluton of 2-naphthoyl chloride (0.94 g, 4.9 mmol), and 2 mL methylene chloride was added dropwise to a 0° C. solution of the compound resulting from Example 81C (0.98 g,4.9 mmol) and triethylamine (0.75 mL, 5.4 mmol) in 23 mL of methylene chloride. The reaction mixture was stirred at 0° C. for 4 hours. Water was added and the layers were separated. The aqueous layer was extracted with methylene chloride. The combined organic extracts were washed successively with 1N KOH, 1N HCl, water and saturated NaCl solution, dried ($MgSO_4$), filtered, and evaporated to afford the title compound (1.6 g) as a white solid. $^1$HNMR (300 MHz, $CDCl_3$) δ 4.70 (d, 2H), 6.55 (br s, 1H), 7.01 (d, 3H), 7.10 (t, 1H), 7.35 (dd, 3H), 7.57 (m, 2H), 7.90 (m, 4H), 8.30 (s, 1H). MS ($DCl/NH_3$) m/e 354 (M+H)$^+$, 371 (M+$NH_4$)$^+$.

EXAMPLE 81E

N-(4-Phenoxybenzyl)-N-(2-naphthylmethyl)amine

A solution of the compound resulting from Example 81D (1.6 g, 4.5 mmol), $BH_3$·THF (9.5 mL, 1.0M solution ), and 40 mL anhydrous THF was stirred at reflux for 2 hours. After cooling to room temperature, 5 mL MeOH was added and the solvents were removed/n vacuo. Hydrogen chloride gas dissolved in methanol (25 mL) was added to the residue, and the solution was stirred at reflux for 1 hour. After cooling to room temperature, the solvents were evaporated/n-vacuo. The residue was treated with 1N KOH and water and then extracted three times with $CH_2Cl_2$. The combined organic layers were washed with water and saturated NaCl solution, dried ($MgSO_4$), filtered, and concentrated in vacuo to afford an oil which was flash chromatographed on silica gel eluting with 3:1 hexane-ethyl acetate to afford the title compound (0.65 g) as a white solid. $^1$HNMR (300 MHz, $CDCl_3$) δ 3.82 (s, 2H), 4.00 (s, 2H), 7.0 (t ,4H), 7.10 (t, 1H), 7.32 (m, 4H), 7.48 (m, 3H), 7.81. (t, 4H). MS ($DCl/NH_3$) m/e 340 (M+H)$^+$.

EXAMPLE 18F (1α,2β,3β,4α)-1,3-Di [N-(4-phenoxybenzyl)-N-(2-methylnaphthyl) aminocarbonyl]cyclobutane-2,4-dicarboxylic acid The compound resulting from Example 81E was reacted by the procedures described in Example 76B to provide the title compound. $^1$HNMR (300 MHz, $CDCl_3$) δ 3.89 (m, 2H), 4.30–4.50 (m, 6H), 4.70 (dd, 1H), 4.92 (dd, 1H), 6.88 (m, 8H), 7.08 (m, 6H), 7.25 (m,8H), 7.36 (m, 8H), 7.52 (d , 1H), 7.54 (s, 1H), 7.70 (m, 5H). MS (FAB) m/e 875 (M+H)$^+$.

EXAMPLE 82

(1α,2β,3β,4α)-1,3-Di [N-((2R)-2-methyl-5-phenylpentyl)-N-(n-propyl)aminocarbonyl] cyclobutane-2,4-dicarboxylic acid

EXAMPLE 82A (2R)-5-Phenyl-2-methylpentanoic acid (4S)-3-((2R)-5-Phenyl-2-methyl-1 -oxopentyl)-4-isopropyl-1,3-oxazolidin -2-one (0.25 g, 0.83 mmol), prepared by the method described in J. Org. Chem. 59: 2261, (1994), was dissolved in 4.2 mL of 4:1 THF:$H_2O$, cooled to 0° C. and purged with $N_2$. 30% Hydrogen peroxide (0.34 mL) was added dropwise, followed by a dropwise addition of a solution of LiOH·$H_2O$ (31.9 mg, 1.3 mmol) and 1.7 mL $H_2O$. The reaction mixture was stirred at 0° C. for 1 hour, then a solution of sodium sulfite (0.42 g, 3.3 mmol) in 2.5 mL of $H_2O$ was added. THF was evaporated in vacuo, and $H_2O$ was added to the residue. This mixture was washed with CH$_2$Cl$_2$ (3×). The aqueous layer was cooled to 0° C., acidified with aqueous hydrochloric acid and extracted (5×) with EtOAc. The combined EtOAc extracts were dried (MgSO$_4$), filtered, and concentrated in vacuo to afford the title compound (0.11 g) as a colorless oil. $^1$HNMR (300 MHz, CDCl$_3$) δ 1.18 (d, 3H), 1.50 (m, 3H), 1.60–1.80 (m, 3H), 2.5 (m, 1H), 2.62 (t, 2H), 7.08 (m, 3H), 7.29 (m, 2H). MS (DCI/NH$_3$) m/e 210 (M+NH$_4$)$^+$.

EXAMPLE 82B

N-((2R)-5-Phenyl-2-methyl-1-oxopentyl)-N-(n-propyl)amine

A solution of the compound resulting from Example 82A (0.12 g, 0.63 mmol), n-propylamine (0.052 mL, 0.63 mmol), EDCl (0.14 g, 0.73 mmol), HOBT (0.02 g, 1.4 mmol), Et$_3$N (0.10 mL, 0.73 mmol), and 3.5 mL anydrous THF was stirred at room temperature for 24 hours. Water was added, and the mixture was extracted with EtOAc (3×). The combined organic layers were washed with 5% sodium bicarbonate, H$_2$O, 1N HCl and saturated NaCl solution, dried (MgSO$_4$), filtered, and concentrated in vacuo to afford the title compound (0.13 g) as a colorless oil. $^1$H NMR (300 MHz, CDCl$_3$) δ 0.90 (t, 3H), 1.12 (d, 3H), 1.38–1.58 (m, 3H), 1.59–1.78 (m, 3H), 2.15 (m, 1H), 2.60 (m, 2H), 3.20 (q, 2H), 5.35 (brs, 1H) 7.20 (t, 3H), 7.28 (m,2H). MS (DCI/NH$_3$) m/e 234 (M+H)$^+$.

EXAMPLE 82C

N-((2R)-5-Phenyl-2-methylpentyl)-N-(n-propyl)amine

Lithium aluminum hydride (0.043 g, 1.12 mmol) was added to a solution of the compound resulting from Example 82B (0.13 g, 0.56 mmol) and 1.5 mL anhydrous THF. The reaction mixture was stirred at reflux for 4.5 hours, cooled to 0° C. and treated sequentially with 0.043 mL of H$_2$O, 0.043 mL of 1N NaOH, and 0.13 mL of H$_2$O. The resultant slurry was filtered through Celite®, and the solids were washed with CH$_2$Cl$_2$ and filtered. The combined filtrates were concentrated in vacuo to afford the title compound (0.11 g) as a colorless oil. $^1$H NMR (300 MHz, CDCl$_3$) δ 0.90 (m, 6H), 1.11–1.23 m, 1H), 1.36–1.54 (m, 2H), 1.64 (m, 4H), 2.38 (dd, 1H), 2.55 (m, 5H), 7.18 (d, 3H), 7.28 (t, 2H). MS (DCI/NH$_3$) m/e 220 (M+H)$^+$.

EXAMPLE 82D (1α,2β,3β,4α)-1,3-Di [N-((2R)-2-methyl-5-phenylpentyl)-N-(n-propyl)aminocarbonyl] cyclobutane-2,4-dicarboxylic acid Using the compound resulting from Example 82C and the procedures described in Example 76B, the title compound was prepared. $^1$H NMR (300 MHz, CDCl$_3$) δ 0.88 (m, 12H), 1.13 (m, 4H), 1.35 (m, 4H), 1.55 (m, 5H), 1.60–1.92 (m, 4H), 2.59 (t, 3H), 3.00–3.30 (m, 6H), 3.40 (m, 1H), 3.72 (m, 2H), 4.12 (t, 2H), 7.15 (m, 5H ), 7.25 (m, 5H). MS (FAB) m/e 635 (M+H)$^+$.

EXAMPLE 83

(1α,2β,3β,4α)-1,3-Di [(3-phenylpiperidin-1-yl) carbonyl]cyclobutane-2,4-dicarboxylic acid

EXAMPLE 83A

3-Phenylpiperidine

A mixture of 3-phenylpyridine (8.0 g, 51.5 mmol), PtO$_2$ (0.8 g), 234 mL of H$_2$O, and 16 mL of concentrated HCl was hydrogenated in a Parr shaker at room temperature for 24 hours. The mixture was filtered, and the filtrate was cooled to 0° C. and was basified with 10N NaOH solution. The mixture was extracted (4×) with CH$_2$Cl$_2$. The combined organic layers were washed with saturated NaCl solution, dried (MgSO$_4$), filtered, and concentrated in vacuo to afford the title compound (7.5 g ) as a clear oil. $^1$H NMR (300 MHz, CDCl$_3$) δ 1.62 (t, 2H), 1.80 (m, 1H), 2.01 (m, 1H), 2.67 (m, 3H), 3.05–3.23 (m, 2H), 7.20 (d, 2H), 7.29 (t, 3H). MS (DCI/NH$_3$) m/e 162 (M+H)$^+$.

EXAMPLE 83B (1α,2β,3β,4α)-1,3-Di [(3-phenylpiperidin-1-yl) carbonyl]cyclobutane-2,4-dicarboxylic acid Using the compound resulting from Example 83A and the procedures described in Example 76B, the title compound was prepared. $^1$H NMR (300 MHz, DMSO-d$_6$) δ 1.60–1.80 (m, 3H), 1.81–1.98(m, 2H), 2.43–2.65 (m, 6H), 2.70–2.82 (m, 1H), 2.90–3.16 (m, 2H), 3.50–3.70 (m, 3H), 3.72–3.93 (m, 3H), 4.40 (q, 2H), 7.29 (m, 10H). MS (FAB) m/e 519 (M+H)$^+$.

EXAMPLE 84

(1α,2β,3β,4α)-1,3-Di [N-benzyl-N-{syn-(4-acetoxy-5-methyl) -6-phenylhexyl}aminocarbonyl] cyclobutane-2,4-dicarboxylic acid

EXAMPLE 84A syn-(1-ethyl-2-hydroxy)-5-benzyloxypentylphenyl ketone

TiCl$_4$ (1.0M solution in CH$_2$Cl$_2$, 16.8 mL) was added dropwise to a −78° C. solution of propiophenone (2.05 g, 15.2 mmol) in 77 mL CH$_2$Cl$_2$. After 5 minutes at −78° C., Et$_3$N (2.3 mL, 16.8 mmol) was added, and the reaction mixture was stirred at −78° C. for 0.5 hours. 4-Benzyloxybutyraldehyde (3.0 g, 16.8 mmol), prepared by the method described in Heterocycles 28(2): 663, (1989), was added dropwise, neat. The reaction mixture was stirred for 0.5 hours at −78° C. and then was quenched by the addition of 50% saturated NH$_4$Cl solution. The solution was warmed to room temperature and extracted with CH$_2$Cl$_2$. The combined organic extracts were washed with saturated NaCl solution, dried (MgSO$_4$), filtered, concentrated, and flash chromatographed on silica gel eluting with 85:15 hexane-ethyl acetate to afford the title compound (3.67 g) as a clear oil. $^1$H NMR (300 MHz, CDCl$_3$) δ 1.28 (d, 3H), 1.60 (t,3H), 1.67–1.88 (m, 2H), 3.52 (m, 3H), 4.03 (m, 1H), 4.51 (s, 2H), 7.32 (s, 5H), 7.48 (t, 2H), 7.59 (t, 2H), 7.95 (d, 2H). MS (DCI/NH$_3$) m/e 313 (M+H)$^+$.

EXAMPLE 84B syn-(1-methyl-2-acetoxy)-5-benzyloxypentylphenyl ketone

Acetic anhydride (1.1 mL, 11.7 mmol) was added dropwise to a 0° C. solution of the compound resulting from Example 84A and a catalytic amount of DMAP in 100 mL CH$_2$Cl$_2$. The reaction mixture was stirred for 24 hours at room temperature, then 0.1N HCl was added. The mixture was extracted with $CH_2Cl_2$ (3×). The combined organic layers were washed with saturated NaCl solution, dried ($MgSO_4$), filtered, and concentrated to afford the title compound (2.9 g) as a colorless oil. $^1H$ NMR (300 MHz, $CDCl_3$) δ 1.21 (d, 3H), 1.58–1.75 (m, 4H), 2.00 (s, 3H), 3.42 (t, 2H), 3.65 (m, 1H), 4.46 (s, 2H), 5.30 (m, 1H), 7.30 (t, 5H), 7.47 (t, 2H), 7.58 (t, 1H), 7.90 (m, 2H). MS (DCI/$NH_3$) m/e 386 $(M+NH_4)^+$.

EXAMPLE 84C

Benzyl-[syn-(4-acetoxy-5-methyl)-6-hydroxy-6-phenyl]hexyl ether

A solution of the compound resulting from Example 84B (0.5 g, 1.4 mmol), $CeCl_3 \cdot 7H_2O$, and 5 mL of MeOH was stirred at 0° C. as $NaBH_4$ (0.16 g, 4.2 mmol) was added portionwise. The reaction mixture was stirred at 0° C. for 0.25 hours, then 25 mL of 3N HCl was added (cautiously), followed by the addition of saturated NaCl solution. The solution was extracted with ether (3×). The combined organic layers were washed with saturated NaCl solution, dried ($MgSO_4$), filtered, and concentrated in vacuo to afford the title compound (0.5 g) as a colorless oil (as a mixture of diastereomeres). $^1H$ NMR (300 MHz, $CDCl_3$) δ 0.60 (d, 1.5H), 0.97 (d, 1.5 H), 1.57–1.74 (m, 4H), 1.85–1.98 (m, 1H), 2.02 (s, 1.5H), 2.15 (s, 1.5H), 3.45 (t, 1H), 3.51 (m, 1H), 4.12 (dd, 0.5H), 4.50 (d, 2H), 4.75 (m, 0.5H), 4.90 (m, 0.5H), 5.43 (m, 0.5H), 7.32 (m,. 10H). MS (DCI/$NH_3$) m/e 374 $(M+NH_4)^+$.

EXAMPLE 84D

Benzyl [syn-(4-acetoxy-5-methyl)-6-trifluoroacetoxy-6-phenyl]hexyl ether

Trifluoroacetic anhydride (0.2 mL, 1.4 mmol) was added dropwise to a 0° C. solution of the compound resulting from Example 84C (0.5 g, 1.4 mmol), pyridine (0.11 mL), and 7 mL $CH_2Cl_2$. The reaction mixture was stirred at 0° C. for 4.5 hours then quenched with 0.1N HCl and extracted with $CH_2Cl_2$ (3×). The combined organic layers were washed with 0.1N HCl, dried ($MgSO_4$), filtered, and concentrated in vacuo to afford the title compound (0.59 g) as a colorless oil (as a mixture of diastereomeres). $^1H$ NMR (300 MHz, $CDCl_3$) δ 0.78 (d, 1.5H), 1.10 (d, 1.5H), 1.50 (m, 1H), 1.64 (m, 2H), 1.78 (m, 1H), 2.02 (d, 3H), 2.32 (m, 1H), 3.39 (t, 1H), 3.50 (m, 2H), 4.98 (d, 2H), 4.67 (m, 0.5H), 5.29 (m, 0.5H), 5.52 (d, 0.5H), 5.78 (d, 0.5H), 7.30 (m, 10H). MS (DCI/$NH_3$) m/e 470 $(M+NH_4)^+$.

EXAMPLE 84E syn-(4-Acetoxy-5-methyl)-6-phenyl-1-hexanol

A mixture of the compound resulting from Example 84D (0.59 g, 1.3 mmol), Pd/C (0.16 g, 10%, dry), and 50 mL of EtOAc was hydrogenated in a Parr shaker at room temperature for 39 hours. The mixture was filtered and concentrated in vacuo, and the residue was flash chromatographed on silica gel eluting with 8:2 hexane-EtOAc to afford the title compound (0.18 g) as a colorless oil. $^1H$ NMR (300 MHz, $CDCl_3$) δ 0.89 (d, 3H), 1.45–1.60 (m, 3H), 1.69 (m, 2H), 2.00 (br s, 1H), 2.09 (s, 3H), 2.33 (dd, 1H), 2.77 (dd,1H), 3.64 (t, 2H), 4.92 (m, 1H), 7.08–7.22 (m, 2H), 7.28 (m, 3H). MS (DCI/$NH_3$) m/e 268 $(M+NH_4)^+$.

EXAMPLE 84F

1-Iodo-syn-(4-acetoxy-5-methyl)-6-phenylhexane

A solution of the compound resulting from Example 84E (0.33 g, 1.39 mmol) and 9.2 mL anhydrous $CH_3CN$ was stirred at room temperature as the following were added sequentially: imidazole (0.24 g, 3.5 mmol), triphenylphosphine (0.40 g, 1.5 mmol), and iodine (0.39 g, 1.5 mmol). The reaction mixture was stirred at room temperature for 1.25 hours, then $H_2O$ was added, and the mixture was extracted with $CH_2Cl_2$. The combined organic layers were washed with saturated sodium thiosulfate solution and saturated NaCl, dried ($MgSO_4$), filtered, and concentrated in vacuo to afford a white solid. The solid was triturated with hexane (3×), decanting after each. The hexane layers were combined, concentrated in vacuo, and the residue obtained flash chromatographed on silica gel eluting with 95:5 hexane-EtOAc to afford the title compound (0.38 g) as a colorless oil. $^1H$ NMR (300 MHz, $CDCl_3$) δ 1.55 (s, 3H), 1.70 (t, 2H), 1.75–1.86 (m, 2H), 1.99 (m, 1H), 2.09 (s, 3H), 2.34 (dd, 1H), 2.77 (dd, 1H), 3.20 (t, 2H), 4.90 (m, 1H), 7.10–7.22 (m, 3H), 7.28 (m, 2H). MS (DCI/$NH_3$) m/e 378 $(M+NH_4)^+$.

EXAMPLE 84G

N-(Benzyl)-N-(t-butyloxycarbonyl)-N-[(syn-4-acetoxy-5-methyl)-6-phenylhexyl]amine A solution of N-benzyl-N-t-butyloxycarbonylamine (0.22 g, 1.05 mmol), prepared by the method described in J. Heterocyclic Chem. 22(5): 1173, (1985), and 0.45 mL of anhydrous DMF was added dropwise to a 0° C. suspension of NaH (0.043 g 1.05 mmol, 60% dispersion, hexane washed) in 1.7 mL of anhyrous DMF. The sodium salt was formed for 0.5 hours at room temperature, then a solution of the compound resulting from Example 84F (0.38 g, 1.05 mmol) in 0.5 mL of anhydrous DMF was added dropwise. The reaction mixture was stirred for 2 days at room temperature. Ice water was added and the solution was extracted (3×) with ethyl acetate. The combined organic layers were washed with $H_2O$, cold 0.1N HCl and saturated NaCl solution, dried ($MgSO_4$), filtered, and concentrated in vacuo to afford the title compound (0.46 g) as a colorless oil. $^1H$ NMR (300 MHz, $CDCl_3$) δ 0.82 (d, 3H), 1.39–1.57 (m, 13H), 1.92 (br s, 1H), 2.06 (s, 3H), 2.30 (dd, 1H), 2.72 (dd, 1H), 3.18 (br d, 2H), 4.29–4.49 (m, 2H), 4.85 (s, 1H), 7.10 (d, 2H), 7.19–7.38 (m , 8H). MS (DCI/$NH_3$) m/e 440 $(M+H)^+$, 457 $(M+NH_4)^+$.

EXAMPLE 84H

N-Benzyl-N-[(syn-4-acetoxy-5-methyl)-6-phenylhexyl]amine

Trifluoroacetic acid (7.7 mL) was added to a 0° C. solution of the compound resulting from Example 84G (0.46 g, 1.07 mmol) and 7.7 mL $CH_2Cl_2$. The reaction was stirred for 0.5 hours at 0° C. and for 1.5 hours at room temperature. The solvent was evaporated in vacuo. Toluene was added and evaporated in vacuo (2×). Amberlite resin (IRA-400-OH, 0.5 g, washed successively with $H_2O$, EtOH, ether, and dried) and 15 mL of $CH_2Cl_2$ was added and the suspension was stirred for 18 hours at room temperature. The suspension was filtered and concentrated in vacuo to afford the title compound (0.33 g) as a colorless oil. $^1H$ NMR (300 MHz, $CDCl_3$) δ 0.85 (d, 3H), 1.58 (m, 4H), 1.95 (s, 1H), 2.07 (s, 3H), 2.31 (m, 2H), 2.68 (s, 1H), 2.74 (dd, 2H), 3.82 (s, 2H), 4.85 (m, 1H), 7.08–7.22 (m, 3H), 7.28 (m, 3H), 7.37 (m, 4H). MS (DCI/$NH_3$) m/e 340 $(M+H)^+$.

EXAMPLE 84I (1α,2β,3β,4α)-1,3-Di [N-benzyl-N-{syn-(4-acetoxy-5-methyl)-6-phenylhexyl}aminocarbonyl] cyclobutane-2,4-dicarboxylic acid Using the procedures described in Example 76B, but substituting the compound resulting from Example 84H provided the title compound. $^1$H NMR (300 MHz, DMSO-$d_6$) δ 0.72–0.89 (m, 6H), 1.22–1.60 (m, 8H), 1.85 (m, 2H), 1.95–2.08 (m, 6H), 2.16–2.41 (m, 3H), 2.62–2.72 (m, 2H), 3.02–3.32 (m, 4H), 3.63–4.09 (m, 4H), 4.10–4.40 (m, 3H), 4.58–4.79 (m, 4H), 6.98–7.31 (m, 20H). MS (FAB) m/e 875 (M+H)$^+$.

EXAMPLE 85

(1α,2β,3β,4α)-1,3-Di[N-benzyl-N-((2R)-5-phenyl-2-methylpentyl)aminocarbonyl]cyclobutane-2,4-dicarboxylic acid

EXAMPLE 85A

N-(Benzyl)-N-(5-phenyl-2(R)-methyl-1-oxopentyl) amine

Using the procedures described in Example 82B, the compound resulting from Example 82A, and substituting benzylamine for n-propylamine provided the title compound. $^1$H NMR (300 MHz, CDCl$_3$), δ 1.16 (d, 3H), 1.40–1.80 (m, 4H), 2.20 (q, 1H), 2.60 (m, 2H), 4.45 (d, 2H), 5.62 (br s, 1H), 7.15 (m, 3H), 7.28 (m, 7H). MS (DCI/NH$_3$) m/e 282 (M+H)$^+$.

EXAMPLE 85B

N-Benzyl-(5-phenyl-2(R)-methylpentyl)amine

Using the procedures described in Example 82C, and substituting the compound obtained in Example 85A for 82B provided the title compound. $^1$H NMR (300 MHz, CDCl$_3$) δ 0.92 (d, 3H), 1.19 (m, 1H), 1.47 (m, 1H), 1.65 (m, 4H), 2.42 (m, 1H), 2.60 (m, 3H), 3.78 (m, 2H), 7.18 (m, 2H), 7.30 (m, 8H). MS (DCI/NH$_3$) m/e 268 (M+H)$^+$.

EXAMPLE 85

(1α,2β,3β,4α)-1,3-Di[N-benzyl-N((2R)-5-phenyl-2-methylpentyl)aminocarbonyl]cyclobutane-2,4-dicarboxylic acid Using the procedures described in Example 76B and sustituting the compound resulting from Example 85B provided the title compound. $^1$H NMR (300 MHz, CDCl$_3$) δ 0.85 (m, 6H), 1.02–1.18 (m, 2H), 1.25–1.37 (m, 2H), 1.42–1.55 (m, 2H), 1.58–1.72 (m, 2H), 1.72–1.92 (m, 2H), 2.43–2.60 (m, 4H), 2.98–3.18 (m, 3H), 3.25–3.40 (m, 1H), 3.60–3.86 (m, 2H), 4.04–4.28 (m, 2H), 4.29–4.40 (m, 1H), 4.43–4.57 (m, 2H), 4.58–4.92 (m, 1H), 7.12 (m, 8H), 7.25 (m, 12H). MS (FAB) m/e 731 (M+H)$^+$.

EXAMPLE 86

(1α,2β,3β,4α)-1,3-Di [N-benzyl-N-{(E)-(2R)-2-methyl-5-phenyl-4-pentenyl}aminocarbonyl] cyclobutane-2,4-dicarboxylic acid

EXAMPLE 86A (E)-(2R)-5-Phenyl-2-methyl-4-pentenoic acid

Using the procedure described in Example 82A and substituting (2R,4S)-3-phenyl-2-methyl-1-oxo-4-(E)-pentenyl-4-isopropyl -1,3-oxazolidin-2-one, prepared by the method described in J. Org. Chem. 59: 2261 (1994), provided the title compound. $^1$HNMR (300 MHz, CDCl$_3$) δ 1.25 (d, 3H), 2.39 (m, 1H), 2.63 (m, 2H), 6.15 (m, 1H), 6.45 (d, 1H), 7.22 (m, 1H), 7.25–7.48 (m, 4H). MS (DCI/NH$_3$) m/e 208 (M+NH$_4$)$^+$.

EXAMPLE 86B

N-Benzyl-N-[2(R)-methyl-1-oxo-5-phenyl-4(E)-pentenyl]amine

Using the procedure described in Example 82B, substituting the compound resulting from Example 86A and sustituting benzylamine for n-propylamine, provided the title compound. $^1$H NMR (300 MHz, CDCl$_3$) δ 1.25 (d, 3H), 2.36 (m, 2H), 2.60 (m, 1H), 4.30–4.60 (m, 2H), 5.73 (br s, 1H), 6.15 (m, 1H), 6.43 (d, 1H), 7.15–7.35 (m, 10H). MS (DCI/NH$_3$) m/e (M+H)$^+$.

EXAMPLE 86C

N-Benzyl-N-[(2R)-2-methyl-5-phenyl-4(E)-pentenyl]amine

Using the procedure described in Example 82C and substituting the compound resulting from Example 86B provided the title compound. $^1$H NMR (300 MHz, CDCl$_3$) δ 0.90 (d, 3H), 1.60 (br s, 1H), 1.83 (m, 1H), 2.09 (m, 1H), 2.32 (m, 1H), 2.45–2.67 (m, 2H), 3.80 (s, 2H), 6.21 (m, 1H), 6.39 (m, 1H), 7.18–7.42 (m, 10H). MS (DCI/NH$_3$) m/e 266 (M+H)$^+$.

EXAMPLE 86D (1α,2β,3β,4α)-1,3-Di [N-benzyl-N-{(E)-(2R)-2-methyl-5-phenyl-4-pentenyl}aminocarbonyl] cyclobutane-2,4-dicarboxylic acid Using the procedure described in Example 76B and substituting the compound resulting from Example 86C, the title compound was prepared. $^1$H NMR (300 MHz, CDCl$_3$) δ 0.90 (m, 8H), 1.30 (m, 3H), 2.00 (m, 3H), 2.22 (m, 2H), 3.00–3.48 (m, 3H), 3.85–3.94 (m, 2H), 4.34 (m, 1H), 4.45–4.75 (m, 2H), 6.10 (m, 2H), 6.35 (m, 2H), 7.10–7.40 (m, 20H). MS (FAB) m/e 727 (M+H)$^+$.

EXAMPLE 87

(1α,2β,3β,4α)-1,3-Di[N-(S)-α-Methylbenzyl-N-(4-phenoxybenzyl)aminocarbonyl]cyclobutane-2,4-dicarboxylic acid To a slurry of 1,2,3,4-cyclobutanetetracarboxylic dianhydride (0.3 g, 1.5 mmol) in CH$_3$CN (5 mL) was added N-(S)-α-methylbenzyl-N-(4-phenoxybenzyl)amine (1.02 g, 3.41 mmol) in CH$_3$CN (10 mL) and 0.1 mL Et$_3$N. The slurry was stirred for 5 minutes at 20° C. resulting in a homogeneous solution. The solution was stirred 20 hours at 20° C., then concentrated in vacuo to a white foam. The foam was dissolved in 100 mL ethyl acetate, washed successively with 50 mL 1N H$_3$PO$_4$ and 10% NaCl solution, dried over anhydrous sodium sulfate, filtered and concentrated in vacuo to afford 1.0 g of a white foamy solid. The crude product containing both isomers was purified by silica gel chromatography eluting with 94:5:1 CHCl$_3$—MeOH—HOAc. The faster moving product was isolated in 4% yield and characterized as the title compound. $^1$H NMR (CDCl$_3$, 500 MHz) δ 7.31–6.73 (m, 28H), 5.92–5.88 (m, 2H), 5.22–5.19 (m, 1H), 4.71–4.65 (d, 1H), 4.40–4.34 (m, 2H), 4.24–3.78 (m, 4H), 1.52–1.50 (s, 3H), 1.32–1.30 (s, 3H). MS (FAB$^+$) m/e 803; (FAB$^-$) m/e 801.

EXAMPLE 88

Dimethyl (1α,2β,3β,4α)-1,3-Di[N-Benzyl-N-(4-phenoxybenzyl)aminocarbonyl]cyclobutane-2,4-dicarboxylate To a solution of the compound resulting from Example 16 (0.3 g, 0.39 mmol) in ethyl ether (10 mL) was added diazomethane (22 mL) until a yellow color persisted. The slurry was stirred 2 hours at 20° C. The reaction mixture was concentrated in vacuo to a yellow oil. The crude product was purified by silica gel chromatography eluting with 99:1 CHCl$_3$—MeOH. The title compound was isolated in 42% yield. $^1$H NMR (CDCl$_3$, 500 MHz) δ 7.37–6.92 (m, 28H), 4.97–4.91 (m, 2H), 4.67–4.58 (m, 2H), 4.38–4.26 (m, 4H), 4.12–4.06 (m, 1H), 3.89–3.83 (m, 1H), 3.54–3.47 (s, 6H). MS (FAB$^+$) m/e 803; (FAB$^-$) m/e 801.

EXAMPLE 89

(1α,2α,3β,4β)-1,3-Di[(N-4-Methoxybenzyl-N-(4-phenoxybenzyl)aminocarbonyl]cyclobutane-2,4-dicarboxylic acid To a slurry of 1,2,3,4-cyclobutanetetracarboxylic dianhydride (0.3 g, 1.5 mmol) in CH$_3$CN (10 mL) was added N-(4-methoxybenzyl)-N-(4-phenoxybenzyl)amine (1.1 g, 3.4 mmol) in CH$_3$CN (10 mL) and 0.1 mL Et$_3$N. The slurry was stirred for 5 minutes at 20° C., resulting in a homogeneous solution. The solution was stirred 20 hours at 20° C., then concentrated in vacuo to a white foam. The foam was dissolved in 100 mL ethyl acetate and washed successively with 50 mL 1NH$_3$PO$_4$ and 10% NaCl solution, then dried over anhydrous Na$_2$SO$_4$, filtered and concentrated in vacuo to afford 1.0 g of white foamy solid. The crude product containing both isomers was purified by silica gel chromatography eluting with 94:5:1 CHCl$_3$—MeOH—HOAc. The faster moving product was isolated in 17% yield and characterized as the title compound. $^1$H NMR (DMSO-d$_6$, 500 MHz) δ 12.75 (broad s, 2H), 7.40–6.79 (m, 26H), 4.76–4.85 (m, 2H), 4.58–4.63 (m, 2H), 4.14–3.93 (m, 8H), 3.72–3.68 (s, 6H). MS(FAB$^+$) m/e 835; (FAB$^-$) m/e 833.

EXAMPLE 90

(1α,2α,3β,4β)-1,3-Di[(N-(R)-α-Methylbenzyl-N-(4-phenoxybenzyl) aminocarbonyl]cyclobutane-2,4-dicarboxylic acid To a slurry of 1,2,3,4-cyclobutanetetracarboxylic dianhydride (0.3 g, 1.5 mmol) in CH$_3$CN (10 mL) was added N-(R)-α-Methylbenzyl-N-(4-phenoxybenzyl)amine (0.96 g, 3.15 mmol) in CH$_3$CN (10 mL) and 0.1 mL Et$_3$N. The slurry was stirred for 5 minutes at 20° C., resulting in a homogeneous solution. The solution was stirred 20 hours at 20° C., then concentrated in vacuo to a white foam. The foam was dissolved in 100 mL ethyl acetate and washed successively with 50 mL 1N H$_3$PO$_4$ and 10% NaCl solution, then dried over anhydrous Na$_2$SO$_4$, filtered and concentrated in vacuo to afford 1.0 g of white foamy solid. The crude product containing both isomers was purified by silica gel chromatography eluting with 94:5:1 CHCl$_3$—MeOH—HOAc. The faster moving product was isolated in 18% yield and characterized as the title compound. $^1$H NMR (DMSO-d$_6$, 500 MHz) δ 7.30–6.77 (m, 28H), 6.03–5.95 (m, 2H), 5.22–5.18 (m, 2H), 4.74–4.71(d, 2H), 4.48–4.09 (m, 2H), 3.61–3.59 (m, 2H), 1.51–1.48 (t, 3H), 1.39–1.26 (t, 3H). MS(FAB$^+$) m/e 803; (FAB$^-$) m/e 801.

EXAMPLE 91

(1α,2α,3β,4β)-1,3-Di[(N-Cyclohexylmethyl-N-(4-phenoxybenzyl)aminocarbonyl]cyclobutane-2,4-dicarboxylic acid To a slurry of 1,2,3,4-cyclobutanetetracarboxylic dianhydride (0.3 g, 1.5 mmol) in CH$_3$CN (10 mL) was added N-cyolohexylmethyl-N-(4-phenoxybenzyl)amine (0.95 g, 3.21 mmol) in CH$_3$CN (10 mL) and 0.1 mL of Et$_3$N. The slurry was stirred for 5 minutes at 20° C., resulting in a homogeneous solution. The solution was stirred 20 hours at 20° C., then concentrated in vacuo to a white foam. The foam was dissolved in 100 mL ethyl acetate and washed successively with 50 mL of 1N H$_3$PO$_4$ and 10% NaCl solution, then dried over anhydrous Na$_2$SO$_4$, filtered and concentrated in vacuo to afford 1.0 g of a white foamy solid. The crude product containing both isomers was purified by silica gel chromatography eluting with 94:5:1 CHCl$_3$—MeOH—HOAc. The faster moving product was isolated in 9% yield and characterized as the title compound. $^1$H NMR (DMSO-d$_6$, 500 MHz) δ 7.31–6.88 (m, 18H), 4.64–4.51 (m, 4H), 4.35–4.25 (m, 2H), 3.77–3.65 (m, 2H), 3.19–3.03 (m, 6H), 1.66–1.61 (broad m, 8H), 1.24–1.11 (broad m, 8H), 0.90–0.86 (m, 4H).

EXAMPLE 92

(1α,2α,3β,4β)-1,3-Di[4-(4-phenoxyphenyl)-1,2,3,6-tetrahydropyridin-1-ylcarbonyl]cyclobutane-2,4-dicarboxylic acid

EXAMPLE 92A

N-tert-Butyloxycarbonyl-4-piperidone

4-Piperidone monohydrate hydrochloride (5 g, 0.033 mol) was added to 50 mL distilled water and stirred until dissolved. To this solution was added solid sodium bicarbonate (3 g, 0.035 mol) followed by tert-butyl dicarbonate (7.2 g, 0.033 mol), and the resulting clear solution was stirred for 20 hours at room temperature. The slurry was treated with 100 mL of ethyl acetate and stirred until all solids dissolved. The layers were separated, and the organic layer was washed with 30 mL of 1N H$_3$PO$_4$ and 30 mL of 10% NaCl, dried over anhydrous Na$_2$SO$_4$, filtered and concentrated in vacuo to afford 5.6 g (86%) of the title compound. $^1$H NMR (300 MHz, CDCl$_3$) δ 3.75–3.68 (t, 4H), 2.47–2.40 (t, 4H), 1.5 (s, 9H). MS (DCI/NH$_3$) m/e 200 (M+H)$^+$, 217 (M+H+NH$_3$)$^+$.

EXAMPLE 92B

N-tert-Butyloxycarbonyl-4-hydroxy-4-(4-phenoxyphenyl)piperidine

4-Bromo diphenyl ether (1 g, 4 mmol) in 5 mL THF was cooled to −78° C. and treated with 1.3M sec-butyllithium (4 mL) in cyclohexane. The mixture was stirred for 5 minutes, then a solution of the compound resulting from Example 92A (0.8 g, 4 mmol) in 5 mL of THF was added dropwise over 2 minutes. The resulting yellow solution was stirred for 4 hours at −78° C., allowed to warm to room temperature over 2 hours and then stirred for 12 hours at room temperature. The reaction was quenched with 40 mL of 10% NH₄Cl solution and stirred for 1 hour. The layers were separated, and the aqueous layer was extracted twice with 50 mL of ethyl ether. The combined organic extracts were washed with 50 mL of 10% NaCl solution, dried over anhydrous Na₂SO₄, filtered and concentrated in vacuo to afford 1.5 g of the title compound as a light yellow oil. $^1$H NMR (CDCl₃, 300 MHz) δ 7.45–6.75 (m, 9H), 3.75–3.68 (t, 4H), 2.47–2.40 (t, 4H), 1.5 (s, 9H). MS (DCI/NH₃) m/e 370 (M+H)$^+$, 387 (M+H+NH₃)$^+$.

EXAMPLE 92C 4-(4-Phenoxyphenyl)-1,2,3,6-tetrahydropyridine

To a 250 mL round bottomed flask fitted with a Dean-Stark trap and condenser was charged with 3.5 g (9.5 mmol) of the compound resulting from Example 92B and 100 mL of toluene. The resulting solution was treated with 5.4 g (0.0284 mol) p-toluene sulfonic acid hydrate, and the mixture was refluxed for 4 hours collecting 0.6 mL of water in the Dean Stark trap. The mixture was cooled to room temperature, and the toluene was removed in vacuo leaving a thick syrup. The residue was treated with 50 mL of 1N NaOH and then extracted with 100 mL of CH₂Cl₂. The organic layer was washed with 30 mL of saturated NaHCO₃ solution and 30 mL of 10% NaCl solution, dried over anhydrous MgSO₄, filtered and concentrated in vacuo to afford 1.2 g of the title compound as a light yellow oil. $^1$H NMR (CDCl₃, 300 MHz) δ 7.45–6.75 (m, 9H), 6.1–6.05 (m, 1H), 3.55–3.51 (m, 2H), 3.15–3.08 (t, 2H), 2.48–2.42 (m, 2H). MS (DCI/NH₃) m/e 251 (M+H)$^+$, 270 (M+H+NH₃)$^+$.

EXAMPLE 92D (1α,2α,3β,4β)-1,3-Di[4-(4-phenoxyphenyl)-1,2,3,6-tetrahydropyridin-1-ylcarbonyl]cyclobutane-2,4-dicarboxylic acid To a slurry of 1,2,3,4-cyclobutanetetracarboxylic dianhydride (0.2 g, 1.02 mmol) in CH₃CN (10 mL) was added the compound resulting from Example 92C (0.6 g, 2.40 mmol) in CH₃CN (10 mL) and 0.1 mL Et₃N. The slurry was stirred for 5 minutes at 20° C., resulting in a homogeneous solution. The solution was stirred 20 hours at 20° C., then concentrated in vacuo to a white foam. The foam was dissolved in 100 mL ethyl acetate and washed successively with 50 mL 1N H₃PO₄ and 10% NaCl solution, then dried over anhydrous Na₂SO₄, filtered and concentrated in vacuo to afford 0.8 g of a white foamy solid. The crude product containing both isomers was purified by silica gel chromatography eluting with 94:5:1 CHCl₃—MeOH—HOAc. The faster moving product was isolated in 18% yield and characterized as the title compound. $^1$H NMR (DMSO-d₆, 500 MHz), δ 7.55–6.78 (m, 18H), 6.12–6.09 (broad d, 2H), 4.17–3.80 (m, 4 H), 3.79–3.05 (m, 10 H), 2.53–2.42 (broad m, 4H). MS (FAB$^+$) m/e 699; (FAB$^-$) m/e 697.

EXAMPLE 93

(1α,2β,3β,4α)-1,3-Di[N-Cyclopropylmethyl-N-(4-phenoxybenzyl)aminocarbonyl]cyclobutane-2,4-dicarboxylic acid

EXAMPLE 93A

N-Cyclopropylmethyl-N-(4-phenoxybenzyl)amine

4-Phenoxybenzaldehyde (3.0 g, 15.1 mmol) and cyclopropylmethylamine (1.1 g, 15.1 mmol) were dissolved in methanol (85 mL) under a nitrogen at room temperature. Sodium cyanoborohydride (0.95 g, 15.1 mmol) was added, and stirring was continued for 48 hours. The solvent was evaporated, and the residue was suspended in ether, washed with brine, and dried over Na₂SO₄. The ether was evaporated, and the crude product was chromatographed on silica gel eluting with 3% methanol in methylene chloride to provide 3.0 g (78%) of the title compound as a colorless oil. $^1$H NMR (CDCl₃, 300 MHz) δ 0.08–0.15 (m, 2H), 0.45–0.55 (m, 2H), 0.93–1.05 (m, 1H), 1.45 (br s, 1H), 2.50 (d, J=7.5 Hz, 2H), 3.78 (s, 2H), 6.95–7.03 (m, 4H) 7.05–7.13 (m, 1H), 7.25–7.38 (m, 4H). MS (DCI/NH₃) m/e 254 (M+H)$^+$.

EXAMPLE 93B (1α,2β,3β,4α)-1,3-Di[N-cyclopropylmethyl-N-(4-phenoxybenzyl)aminocarbonyl]cyclobutane-2,4-dicarboxylic acid A slurry of 1,2,3,4-cyclobutanetetracarboxylic dianhydride (1.0 g, 5.0 mmol) in acetonitrile (17 mL) under a nitrogen at room temperature was treated with a solution of N-cyclopropylmethyl-N-(4-phenoxybenzyl)amine (2.5 g, 10.0 mmol) in acetonitrile (20 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile (7 mL), triturated with water, and lyophilized to provide 1.2 g (34%) of the title compound as a white powder. m.p. 94°–95° C. $^1$H NMR (DMSO-d₆, 300 MHz) δ 0.01–1.25 (m, 4H), 0.27–0.52 (m, 4H), 0.80–0.96 (m, 2H), 2.68–2.92 (m, 2H), 3.20–3.55 (m, 2H), 3.56–3.68 (m, 2H), 3.89–3.98 (m, 9H), 4.00–4.10 (m, 1H), 4.28–4.58 (m, 2H), 4.65–4.89 (m, 2H), 6.85–7.04 (m, 8H), 7.08–7.30 (m, 6H), 7.33–7.43 (m, 4H), 12.11–12.20 (br s, 2H). MS (FAB) m/e 703 (M+H)$^+$.

EXAMPLE 94

(1α,2β,3β,4α)-1,3-Di[N-(4-fluorobenzyl)-N-(4-phenoxybenzyl)aminocarbonyl]cyclobutane-2,4-dicarboxylic acid

EXAMPLE 94A

N-(4-Fluorobenzyl)-N-(4-phenoxybenzyl)amine

4-Phenoxybenzaldehyde (1.0 g, 5.0 mmol) and 4-fluorobenzylamine (631 mg, 5.0 mmol) were dissolved in methanol (17 mL) under a nitrogen at room temperature. Sodium cyanoborohydride (317 mg, 5.0 mmol) was added, and stirring was continued for 48 hours. The solvent was evaporated, and the residue was suspended in ether, washed with brine, and dried over Na₂SO₄. The ether was evaporated, and the crude product was chromatographed on silica gel eluting with 3% methanol in methylene chloride to provide 1.5 g (97%) of the title compound as a colorless oil. $^1$H NMR (CDCl₃, 300 MHz) δ 1.55 (s, 1H), 3.76 (s, 2H), 3.78 (s, 2H), 6.95–7.15 (m, 7H), 7.25–7.40 (m, 6H). MS (DCI/N H₃) m/e 308 (M+H)$^+$.

EXAMPLE 94B (1α,2β,3β,4α)-1,3-Di[N-(4-fluorobenzyl)-N-(4-phenoxybenzyl)aminocarbonyl]cyclobutane-2,4-dicarboxylic acid A slurry of 1,2,3,4-cyclobutanetetracarboxylic dianhydride (450 mg, 2.3 mmol) in acetonitrile (4 mL) under nitrogen at room temperature was treated with a solution of N-(4-fluorobenzyl)-N-(4-phenoxybenzyl)amine (1.4 g, 4.6 mmol) in acetonitrile (6 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile (5 mL), triturated with water, and lyophilized to provide 890 mg (48%) of the title compound as a white powder. m.p. 95°–98° C. $^1$H NMR (DMSO-$d_6$, 300 MHz) δ 3.66–3.74 (m, 2H), 3.95–4.24 (m, 2H), 4.62–4.73 (m, 4H), 4.80–4.88 (m, 4H), 6.90–7.28 (m, 18H), 7.34–7.42 (m, 8H), 12.62–12.75 (br s, 2H). MS (FAB) m/e 811 (M+H)$^+$.

EXAMPLE 95

(1α,2β,3β,4α)-1,3-Di[N-(dibenzofuran-2-ylmethyl)-N-(4-phenoxybenzyl)aminocarbonyl]cyclobutane-2,4-dicarboxylic acid

EXAMPLE 95A

2-Acetyldibenzofuran

Aluminum chloride (23.8 g, 178.4 mmol) was added portionwise to a solution of dibenzofuran (30.0 g, 178.4 mmol) and acetyl chloride (14.0 g, 178.4 mmol) in dichloroethane at 0° C. After 8 hours, the reaction was quenched with 6N HCl. The layers were separated and the methylene chloride layer was dried (MgSO$_4$), filtered and concentrated to provide a yellow solid. The solid was recrystallized 3 times from hexane to provide 10.6 g (28%) of the title compound as a white solid. $^1$H NMR (CDCl$_3$, 300 MHz) δ 2.7 (s, 3H), 7.4 (dt, J=7.5 Hz, 0.5 Hz, 1H), 7.5 (dt, J=7.5 Hz, 0.5 Hz, 1H), 7.65 (d, J=7.5 Hz, 2H), 8.0 (d, J=7.5 Hz, 1H), 8.15 (dd, J=7.5 Hz, 0.5 Hz), 8.6 (d, J=0.5 Hz). MS (DCI/NH$_3$) m/e 211 (M+H)$^+$.

EXAMPLE 95B

2-Carboxydibenzofuran

Bromine (2.3 g, 14.4 mmol) was added to a solution of NaOH (1.57 g, 39.2 mmol) in H$_2$O at 0° C. Dioxane (8 mL) and the compound resulting from Example 95A (1.0 g, 4.8 mmol) were then added, and the solution was refluxed for 3 hours. The solution was cooled to room temperature and washed with methylene chloride (2×100 mL). The water layer was acidified to pH 0 with concentrated HCl, and the resulting white solid was filtered. The crude product was recrystallized from ethyl acetate to provide 526 mg (52%) of the title compound as a white solid. $^1$H NMR (DMSO-$d_6$, 300 MHz), δ 7.45 (dt, J=7.5 Hz, 0.5 Hz, 1H), 7.6 (dr, J=7.5 Hz, 0.5 Hz, 1H), 7.8 (m, 2H), 8.15 (dd, J=7.5 Hz, 0.5 Hz, 1H), 8.33 (dd, J=7.5 Hz, 0.5 Hz, 1H), 8.8, (d, J=0.5 Hz, 1H). MS (DCI/NH$_3$) m/e 213 (M+H)$^+$.

EXAMPLE 95C

2-Propylaminocarbonyldibenzofuran

A solution of the compound resulting from Example 95B (400 mg, 1.9 mmol) and N-methylmorpholine (202 mg, 2.0 mmol) in THF at −10° C. was treated with isobutyl chloroformate (272.1 mg, 2.0 mmol). After 15 minutes, n-propylamine (561.5 mg, 9.5 mmol) was added, and the solution was stirred at 10° C. for 1 hour and room temperature for 1 hour. The volatiles were removed under reduced pressure, and the residue was partitioned between ethyl acetate and water. The ethyl acetate layer was dried (MgSO$_4$), filtered and concentrated to provide a white solid. Chromatography of the solid eluting with 20% ethyl acetate-hexane provided 477 mg (99%) of the title compound as a white powder. $^1$H NMR (CDCl$_3$, 300 MHz) δ 1.15 (t, J=7.5 Hz, 3H), 1.65 (m,.2H), 2.8 (t, J=7.5 Hz, 2H), 3.95 (s, 1H), 7.25–7.6 (m, 6H), 7.95 (m, 1H). MS (DCI/N H$_3$) m/e 254 (M+H)$^+$.

EXAMPLE 95D

N-Propyl-N-(dibenzofuran2-ylmethyl)amine

The compound resulting from Example 95C (470 mg, 1.9 mmol) in THF (6 mL) was treated with BH$_3$·THF (5.6 mL of a 1M solution) and refluxed for 18 hours. The solution was then treated with HCl-saturated methanol (35 mL) and refluxed an additional 18 hours. Removal of all volatiles provided an oil which was triturated with 10% NaHCO$_3$ and extracted with methylene chloride. The combined organic extracts were dried (Na$_2$SO$_4$), filtered and concentrated to provide 160 mg (36%) of the title compound as a yellow oil. $^1$H NMR δ 0.95 (t, J=7.5 Hz, 3H), 1.4 (br s, 1H), 1.6 (m, 2H), 2.65 (t, J=7.5 Hz, 2H), 3.95 (s, 2H), 7.30–7.6 (m, 6H), 7.95 (m, 1H). MS (DCI/NH$_3$) 240 (M+H)$^+$.

EXAMPLE 95E (1α,2β,3β,4α)-1,3-Di[N-(dibenzofuran-2-ylmethyl)-N-(4-phenoxybenzyl)aminocarbonyl]cyclobutane-2,4-dicarboxylic acid A slurry of 1,2,3,4-cyclobutanetetracarboxylic dianhydride (44 mg, 0.23 mmol) in acetonitrile (800 μL) under nitrogen at room temperature was treated with a solution of the compound resulting from Example 95D (108 mg, 0.45 mmol) in acetonitrile (900 μL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile (15 mL), triturated with water, and lyophilized to provide 76 mg (49%) of the title compound as a white powder. m.p. 99°–101° C. $^1$H NMR (DMSO-$d_6$, 300 MHz) δ 0.7–0.85 (m, 6H), 1.40–1.6 (m, 4H), 2.85–3.15 (m, 2H), 3.30–3.75 (envelope, 4H), 4.1–4.2 (m, 2H), 4.39–4.60 (m, 2H), 4.81–5.1 (m, 2H), 7.28–7.7 (m, 10H), 7.95–7.82 (m, 4H), 12.3–12.6 (br s, 2H). MS (FAB) m/e 675 (M+H)$^+$.

EXAMPLE 96

(1α,2β,3β,4α)-1,3-Di[N-((2R)-2-(1-naphthyl)eth-2-yl) -N-(4-phenoxybenzyl)aminocarbonyl] cyclobutane-2,4-dicarboxylic acid

EXAMPLE 96A

N-((2R)-2-(1-Naphthyl)eth-2-yl)-N-(4-phenoxybenzyl)amine

4-Phenoxybenzaldehyde (2.34 g, 11.8 mmol) and (2R)-2-(1-naphthyl)eth-2-ylamine (2.02 g, 11.8 mmol) were dissolved in methanol (39 mL) under a nitrogen at room temperature. Sodium cyanoborohydride (742 mg, 11.8 mmol) was added, and stirring was continued for 48 hours. The solvent was evaporated and the residue was suspended in ether, washed with brine, and dried over $Na_2SO_4$. The ether was evaporated, and the crude product was chromatographed on silica gel eluting with 3% methanol in methylene chloride to provide 3.21 g (77%) of the title compound as a colorless oil. $^1$H NMR ($CDCl_3$, 300 MHz), δ 1.52 (d, J=6 Hz, 3H), 1.64 (s, 1H), 3.7 (dd, J=13.5 Hz, 7.5 Hz, 2H), 4.7 (q, J=7.5 Hz, 1H), 6.95 (m, 4H), 7.08 (m, 1H), 7.3 (m, 4H), 7.5 (m, 3H), 7.75 (m, 2H), 7.9 (m, 1H), 8.15 (m, 1H). MS ($DCl/NH_3$) m/e 354 $(M+H)^+$.

EXAMPLE 96B

(1α,2β,3β,4α)-1,3-Di[N-((2R)-2-(1-naphthyl)eth-2-yl) -N-(4-phenoxybenzyl)aminocarbonyl] cyclobutane-2,4-dicarboxylic acid A slurry of 1,2,3,4-cyclobutanetetracarboxylic dianhydride (610 mg, 3.1 mmol) in acetonitrile (6.2 mL) under nitrogen at room temperature was treated with a solution of the compound resulting from Example 96A (2.20 g, 6.2 mmol) in acetonitrile (7.8 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile (5 mL), triturated with water, and lyophilized to provide 26 mg (9%) of the title compound as a white powder. m.p. 97° C. $^1$H NMR (DMSO-$d_6$, 500 MHz), δ 1.25–1.84 (envelope, 6H), 3.6–5.0 (envelope, 10H), 6.0–8.5 (envelope, 32 H), 12.2 (br s, 2H). MS (FAB) m/e 904 $(M+H)^+$.

EXAMPLE 97

(1α,2β,3β,4α)-1,3-Di[N-cyclopentyl-N-(4-phenoxybenzyl)aminocarbonyl]cyclobutane-2,4-dicarboxylic acid

EXAMPLE 97A

N-Cyclopentyl-N-(4-phenoxybenzyl)amine

4-Phenoxybenzaldehyde (5.0 g, 25.1 mmol) and cyclopentylamine (2.5 g, 25 mmol) were dissolved in methanol (85 mL) under nitrogen at room temperature. Sodium cyanoborohydride (1.57 g, 25.0 mmol) was added, and stirring was continued for 48 hours. The solvent was evaporated, and the residue was suspended in ether, washed with brine, and dried over $Na_2SO_4$. The ether was evaporated, and the crude product was chromatographed on silica gel eluting with 3% methanol in methylene chloride to provide 5.5 g (83%) of the title compound as a colorless oil. $^1$H NMR ($CDCl_3$, 300 MHz), δ 1.31–1.45 (m, 2H), 1.49–1.65 (m, 2H), 1.65–1.80 (m, 3H), 1.81–1.95 (m, 2H), 3.15 (p, J=7.5 Hz, 1H), 3.75 (s, 2H), 6.94–7.04 (m, 4H), 7.05–7.14 (m, 1H), 7.25–7.40 (m, 4H). MS ($DCl/NH_3$) m/e 268 $(M+H)^+$.

EXAMPLE 97B

(1α,2β,3β,4α)-1,3-Di[N-cyclopentyl-N-(4-phenoxybenzyl)aminocarbonyl]cyclobutane-2,4-dicarboxylic acid A slurry of 1,2,3,4-cyclobutanetetracarboxylic dianhydride (2.0 g, 10 mmol) in acetonitrile (33 mL) under nitrogen at room temperature was treated with a solution of the compound resulting from Example 97A (5.4 g, 20.0 mmol) in acetonitrile (40 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile (15 mL), triturated with water, and lyophilized to provide 2.2 g (30%) of the title compound as a white powder. m.p. 94°–95° C. $^1$H NMR (DMSO-$d_6$, 300 MHz) δ 1.35–1.85 (envelope, 18H), 3.48–3.58 (m, 1H), 3.60–3.68 (m, 1H), 3.98–4.36 (m, 4H), 4.45–4.55 (m, 2H), 6.82–7.04 (m, 8H), 7.06–7.17 (m, 3H), 7.18–7.28 (m, 3H), 7.29–7.44 (m, 4H), 12.01–12.27 (br s, 2H). MS (FAB) m/e 731 $(M+H)^+$.

EXAMPLE 98

(1α,2β,3β,4α)-1,3-Di[N-cyclohexyl-N-(4-phenoxybenzyl)aminocarbonyl]cyclobutane-2,4-dicarboxylic acid

EXAMPLE 98A

N-Cyclohexyl-N-(4-phenoxybenzyl)amine

4-Phenoxybenzaldehyde (5.0 g, 25.0 mmol) and cyclohexylamine (2.5 g, 25 mmol) were dissolved in methanol (85 mL) under nitrogen at room temperature. Sodium cyanoborohydride (1.57 g, 25.0 mmol) was added, and stirring was continued for 48 hours. The solvent was evaporated and the residue was suspended in ether, washed with brine, and dried over $Na_2SO_4$. The ether was evaporated, and the crude product was chromatographed on silica gel eluting with 3% methanol in methylene chloride to provide 6.4 g (91%) of the title compound as a colorless oil. $^1$H NMR ($CDCl_3$, 300 MHz) δ 1.05–1.35 (m, 5H), 1.55–1.65 (m, 1H), 1.70–1.80 (m, 3H), 1.85–2.00 (m, 2H), 2.45–2.55 (m, 1 H) 3.80 (s, 2H), 6.95–7.04 (m, 4H), 7.05 (tt, J=7.5, 1.5 Hz, 1H), 7.25–7.35 (m, 4H). MS ($DCl/NH_3$) m/e 282 $(M+H)^+$.

EXAMPLE 98B

(1α,2β,3β,4α)-1,3-Di[N-cyclohexyl-N-(4-phenoxybenzyl)aminocarbonyl]cyclobutane-2,4-dicarboxylic acid A slurry of 1,2,3,4-cyclobutanetetracarboxylic dianhydride (2.0 g, 10 mmol) in acetonitrile (33 mL) under nitrogen at room temperature was treated with a solution of the compound resulting from Example 98A (5.6 g, 20.0 mmol) in acetonitrile (40 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile (15 mL), triturated with water, and lyophilized to provide 2.9 g (38%) of the title compound as a white powder. m.p. 130°–131° C. $^1$H NMR (DMSO-$d_6$, 300 MHz) δ 0.82–1.78 (envelope, 22H), 3.48–3.69 (m, 2H), 3.64–3.73 (m, 1H), 3.84–3.94(m, 1H), 4.10–4.64 (m, 4H), 6.80–7.05 (m, 8H), 7.07–7.18 (m, 3H), 7.19–7.44 (m, 7H), 12.15–12.29 (br s, 2H). MS (FAB) m/e 779 $(M+H)^+$.

EXAMPLE 99

(1α,2β,3β,4α)-1,3-Di[N-cyclobutyl-N-(4-phenoxybenzyl)aminocarbonyl]cyclobutane-2,4-dicarboxylic acid

EXAMPLE 99A

N-Cyclobutyl-N-(4-phenoxybenzyl)amine

4-Phenoxybenzaldehyde (5.0 g, 25.0 mmol) and cyclobutylamine (1.8 g, 25.0 mmol) were dissolved in methanol (85 mL) under nitrogen at room temperature. Sodium cyanoborohydride (1.57 g, 25.0 mmol) was added, and stirring was continued for 48 hours. The solvent was evaporated, and the residue was suspended in ether, washed with brine, and dried over $Na_2SO_4$. The ether was evaporated, and the crude product was chromatographed on silica gel eluting with 3% methanol in methylene chloride to provide 5.63 g (89%) of the title compound as a colorless oil. $^1$H NMR ($CDCl_3$, 300 MHz) δ 1.56–1.80 (m, 5H), 2.15–2.30 (m, 2H), 3.25–3.39 (m, 1H), 3.68 (s, 2H), 6.94–7.04 (m, 4H), 7.05–7.15 (tt, J=7.5, 1.5 Hz, 1H), 7.25–7.38 (m, 4H). MS (DCI/$NH_3$) m/e 254 (M+H)$^+$.

EXAMPLE 99B (1α,2β,3β,4α)-1,3-Di[N-cyclobutyl-N-(4-phenoxybenzyl)aminocarbonyl]cyclobutane-2,4-dicarboxylic acid A slurry of 1,2,3,4-cyclobutanetetracarboxylic dianhydride (2.0 g, 10 mmol) in acetonitrile (33 mL) under nitrogen at room temperature was treated with a solution of the compound resulting from Example 99A (5.2 g, 20.0 mmol) in acetonitrile (40 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile (15 mL), triturated with water, and lyophilized to provide 2.3 g (33%) of the title compound as a white powder. m.p. 122°–125° C. $^1$H NMR (DMSO-$d_6$, 300 MHz) δ 1.44–1.64 (m, 4H), 1.80–2.19 (m, 10H), 3.48–3.57 (m, 1H), 3.60–3.80 (m, 2H), 3.90–4.50 (m, 1H), 4.20–4.75 (m, 4H) 6.84–7.02 (m, 8H), 7.04–7.28 (m, 6H), 7.30–7.44 (m, 4H), 12.20–12.31 (br s, 2H). MS (FAB) m/e 703 (M+H)$^+$.

EXAMPLE 100

(1α,2β,3β,4α)-1,3-Di[N-cyclobutylmethyl-N-(4-phenoxybenzyl)aminocarbonyl]cyclobutane-2,4-dicarboxylic acid

EXAMPLE 100A

N-(Cyclobutylmethyl)-N-(4-phenoxybenzyl)amine

A cooled (0° C.) solution of N-(4-phenoxybenzyl) cyclobutanecarboxamide (0.60 g, 2.1 mmol) in THF (7 mL) was treated with 1M solution of LAH in THF (2.1 mL). The solution was refluxed for 2 hours then cooled to 0° C. and quenched with $Na_2SO_4·10\ H_2O$. The suspension was diluted with THF and filtered through a pad of celite. Evaporation of the solvent provided 0.56 g (99%) of the title compound as a colorless oil. $^1$H NMR ($CDCl_3$, 500 MHz) δ 1.15 (br s, 1H), 1.62–1.70 (m, 2H), 1.80–1.98 (m, 3H), 2.02–2.10 (m, 2H), 2.50 (p, J=7.5 Hz, 1H), 2.65 (d, J=7.5 Hz, 2H), 3.75 (s, 2H), 6.95–7.02 (m, 4H) 7.05–7.10 (tt, J=7.5, 1.5 Hz, 1H), 7.25–7.35 (m, 4H). MS (DCI/$NH_3$) m/e 268 (M+H)$^+$.

EXAMPLE 100B (1α,2β,3β,4α)-1,3-Di[N-cyclobutylmethyl-N-(4-phenoxybenzyl)aminocarbonyl]cyclobutane-2,4-dicarboxylic acid A slurry of 1,2,3,4-cyclobutanetetracarboxylic dianhydride (0.092 g, 0.47 mmol) in acetonitrile (3 mL) under nitrogen at room temperature was treated with a solution of the compound resulting from Example 100A (0.25 g, 0.94 mmol) in acetonitrile (2 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile (2 mL), triturated with water, and lyophilized to provide 100 mg (29%) of the title compound as a white powder. m.p. 88°–90° C. $^1$H NMR (DMSO-$d_6$, 300 MHz) δ 1.55–2.00 (m, 12H), 2.90–3.01 (m, 1H), 3.04–3.15 (m, 1H), 3.35–3.46 (m, 3H), 3.51–3.68 (m, 3H), 3.82–5 3.97 (m, 1H), 4.00–4.14 (m, 1H), 4.18–4.35 (m, 2H), 4.60–4.83 (m, 2H), 6.89–7.05 (m, 8H), 7.09–7.17 (m, 2H), 7.18–7.28 (m, 4H), 7.34–7.44 (m, 4H), 12.00–12.27 (br s, 2H). MS (FAB) m/e 731 (M+H)$^+$.

EXAMPLE 101

(1α,2β,3β,4α)-1,3-Di[N-cyclopentylmethyl-N-(4-phenoxybenzyl)aminocarbonyl]cyclobutane-2,4-dicarboxylic acid

EXAMPLE 101A

N-Cyclopentylmethyl-N-(4-phenoxybenzyl)amine

4-Phenoxybenzaldehyde (3.0 g, 15.1 mmol) and cyclopentylmethylamine (1.49 g, 15.1 mmol) were dissolved in methanol (85 mL) under nitrogen at room temperature. Sodium cyanoborohydride (0.95 g, 15.1 mmol) was added, and stirring was continued for 48 hours. The solvent was evaporated, and the residue was suspended in ether, washed with brine, and dried over $Na_2SO_4$. The ether was evaporated, and the crude product was chromatographed on silica gel eluting with 3% methanol in methylene chloride to provide 3.4 g (80%) of the title compound as a colorless oil. $^1$H NMR ($CDCl_3$, 300 MHz) δ 1.10–1.24 (m, 2H), 1.45–1.67 (m, 2H), 1.71–1.90 (m, 3H), 2.06 (p, J=7.5 Hz, 1H), 2.58 (d, J=7.5 Hz, 2H), 3.79 (s, 2H), 6.95–7.05 (m, 4H) 7.09 (tt, J=7.5, 1.5 Hz, 1H), 7.28–7.38 (m, 4H). MS (DCI/$NH_3$) m/e 282 (M+H)$^+$.

EXAMPLE 101B (1α,2β,3β,4α)-1,3-Di[N-cyclopentylmethyl-N-(4-phenoxybenzyl)aminocarbonyl]cyclobutane-2,4-dicarboxylic acid A slurry of 1,2,3,4-cyclobutanetetracarboxylic dianhydride (2.0 g, 10 mmol) in acetonitrile (33 mL) under nitrogen at room temperature was treated with a solution of the compound resulting from Example 101 A (5.6 g, 20.0 mmol) in acetonitrile (20 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile (15 mL), triturated with water, and lyophilized to provide 2.8 g (37%) of the title compound as a white powder. m.p. 94°–95° C. $^1$H NMR (DMSO-$d_6$, 300 MHz) δ 1.00–1.22 (m, 4H), 1.34–1.70 (m, 16H), 2.00–2.18 (m, 2H), 2.75–3.00 (m, 1H), 3.13–3.70 (m, 2H), 3.66–4.06 (m, 1H), 4.22–4.40 (m, 2H), 4.60–4.78 (m, 2H), 6.85–7.04 (m, 8H), 7.08–7.29 (m, 6H), 7.32–7.44 (m, 4H), 12.17–12.34 (br s, 2H). MS (FAB) m/e 759 (M+H)$^+$.

EXAMPLE 102

(1α,2β,3β,4α)-1,3-Di[N-((2R)-Sec-butyl)-N-(4-phenoxybenzyl)aminocarbonyl]cyclobutane-2,4-dicarboxylic acid

EXAMPLE 102A

N-((R)-sec-butyl)-N-(4-phenoxybenzyl)amine

4-Phenoxybenzaldehyde (8.13 g, 41.0 mmol) and (2R)-sec-butylamine (3.0 g, 41.0 mmol) were dissolved in methanol (137 mL) under nitrogen at room temperature. Sodium cyanoborohydride (2.58 g, 41.0 mmol) was added, and stirring was continued for 48 hours. The solvent was evaporated, and the residue was suspended in ether, washed with brine, and dried over $Na_2SO_4$. The ether was evaporated, and the crude product was chromatographed on silica get eluting with 3% methanol in methylene chloride to provide 8.01 g (77%) of the title compound as a colorless oil. $[\alpha]_D$=−17.6°. $^1$H NMR (CDCl$_3$, 300 MHz) δ 0.9 (t, J=7.5 Hz, 3H), 1.1 (d, J=7.5 Hz, 3H), 1.3–1.6 (m, 2H), 1.7 (br s, 1H), 2.65 (m, 1H), 3.75 (dd, J=12 Hz, 2H), 6.94–7.15 (m, 4H), 7.05–7.15 (m, 1H), 7.25–7.38 (m, 4H). MS (DCl/NH$_3$) m/e 254 (M+H)$^+$.

EXAMPLE 102B (1α,2β,3β,4α)-1,3-Di[N-((2R)-sec-butyl)-N-(4-phenoxybenzyl)aminocarbonyl]cyclobutane-2,4-dicarboxylic acid A slurry of 1,2,3,4-cyclobutanetetracarboxylic dianhydride (457 mg, 2.3 mmol) in acetonitrile (7.7 mL) under nitrogen at room temperature was treated with a solution of N-((2R)-sec-butyl)-N-(4-phenoxybenzyl)amine (1.19 g, 4.6 mmol) in acetonitrile (9.3 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile (5 mL), triturated with water, and lyophilized to provide 740 mg (45%) of the title compound as a white powder. m.p. 111°–112° C. $^1$H NMR (DMSO-d$_6$, 300 MHz) ,50.6–1.6 (envelope, 18H), 3.4–4.6 (envelope, 8H), 6.82–7.45 (envelope, 18 H), 12.4 (br s, 2H). MS (FAB) m/e 707 (M+H)$^+$.

EXAMPLE 103

(1α,2β,3β,4α)-1-[N-Benzyl-N-(4-phenoxybenzyl)aminocarbonyl]-3-[N-(thien-2-ylmethyl)-N-(4-phenoxybenzyl)aminocarbonyl]cyclobutane-2,4-dicarboxylic acid The title compound was prepared by the procedures described in Example 40. $^1$H NMR (CDCl$_3$, 500 MHz) δ 3.50–3.75 (m, 2H), 4.0–4.3 (m, 3H), 4.33–4.56 (m, 3H), 4.62–4.89 (m, 4H), 6.89–7.49 (m, 26H). MS m/e 781 (M+H)$^+$.

EXAMPLE 104

(1α,2β,3β,4α)-1,3-Di[N-(3,4-Dichlorobenzyl)-N-(4-phenoxybenzyl)aminocarbonyl]cyclobutane-2,4-dicarboxylic acid To a slurry of 1,2,3,4-cyclobutanetetracarboxylic dianhydride (0.26 g, 1.33 mmol) in CH$_3$CN (5 mL) was added N-(3,4-dichlorobenzyl)-N-(4-phenoxybenzyl)amine (1.00 g, 2.8 mmole) in CH$_3$CN (10 mL). The slurry was stirred for 5 minutes at 20° C., resulting in a homogeneous solution. This solution was stirred 20 hours at 20° C., then concentrated in vacuo to a white foam. The foam was dissolved in 100 mL of ethyl acetate and washed successively with 50 mL 1N H$_3$PO$_4$ and 10% NaCl solution, dried over anhydrous sodium sulfate, filtered and concentrated in vacuo to afford 1.0 g of a white foamy solid. The crude product containing both isomers was purified by silica gel chromatography eluting with 94:5:1 CHCl$_3$—MeOH—HOAc. The faster moving product was isolated in 12% yield and characterized as the title compound. $^1$H NMR (CDCl$_3$, 300 MHz) δ 7.39–6.87 (m, 24H), 4.81–4.71 (m, 2H), 4.59–4.09 (m, 8H), 3.88–3.81 (m, 2H). MS (FAB$^+$) m/e 913; (FAB$^-$): 911.

Inhibition of Protein Farnesyltransferase

In vitro inhibition of protein farnesyltransferase may be measured by the following procedure. (Procedures for determination of the inhibition of farnesylation of the oncogene protein Ras are described by Goldstein, et al., J. Biol. Chem., 266: 15575–15578 (1991) and by Singh in U.S. Pat. No. 5,245,061 both of which are incorporated herein by reference.)

Rat brain protein farnesyltransferase activity was measured using the biotin-lamin substrate (which is known to undergo farnesylation in a manner analogous to Ras protein) and radioactive farnesyl diphosphate provided by Amersham Life Science in their commercial scintillation proximity assay kit for the determination of farnesyltransferase. The enzyme was purified according to Reiss, Y., et al., Cell, 62: 81–88 (1990), utilizing steps one through three. The specific activity of the enzyme was approximately 10 nmol substrate farnesylated/mg enzyme/hour. The percent inhibition of the farnesylation caused by the compounds of the invention (at 10×10$^{-6}$M) compared to an uninhibited control sample was evaluated in the same Amersham test system. The results for the compounds of the invention are shown in Table 1. The data show that the compounds of the invention are inhibitors of protein farnesyltransferase.

TABLE 1

| In vitro Inhibition of Protein Farnesyltransferase | | | |
|---|---|---|---|
| Ex. No. | % Inhibition at 10 μM | Example No. | % Inhibition at 10 μM |
| 14 | 34 | 15 | 45 |
| 16 | 98 | 17 | 49 |
| 18 | 55 | 19 | 80 |
| 21 | 27 | 22 | 78 |
| 24 | 31 | 25 | 59 |
| 26 | 69 | 27 | 69 |
| 28 | 28 | 29 | 38 |
| 30 | 37 | 31 | 74 |
| 32 | 54 | 33 | 64 |
| 34 | 40 | 36 | 24 |
| 37 | 22 | 38 | 85 |
| 39 | 66 | 40 | 94* |

TABLE 1-continued

In vitro Inhibition of Protein Farnesyltransferase

| Ex. No. | % Inhibition at 10 μM | Example No. | % Inhibition at 10 μM |
|---|---|---|---|
| 41 | 63 | 42 | 67 |
| 43 | 54* | 44 | 81 |
| 47 | 50 | 48 | 61 |
| 49 | 23 | 50 | 35 |
| 51 | 68 | 52 | 51 |
| 53 | 69 | 54 | 59 |
| 55 | 22* | 56 | 78 |
| 57 | 26* | 58 | 31* |
| 59 | 54 | 60 | 23* |
| 61 | 73 | 62 | 69 |
| 63 | 68 | 64 | 64 |
| 65 | 52* | 66 | 88 |
| 67 | 61* | 68 | 49 |
| 69 | 31* | 70 | 77 |
| 71 | 32* | 72 | 82* |
| 73 | 92* | 74 | 22* |
| 76 | 66 | 77 | 48 |
| 78 | 83 | 79 | 43 |
| 80 | 51 | 81 | 62* |
| 82 | 21* | 83 | 37 |
| 84 | 93* | 85 | 58* |
| 86 | 61* | 87 | 86 |
| 89 | 50 | 90 | 66* |
| 91 | 36 | 92 | 45* |
| 93 | 74 | 94 | 99 |
| 95 | 55 | 96 | 71* |
| 97 | 32 | 98 | 31 |
| 99 | 52 | 100 | 21* |
| 101 | 26* | 102 | 37 |

*Indicates inhibition at 1 μM

Inhibition of Squalene Synthase

In vitro inhibition of squalene synthase may be measured by the following procedure.

Rat liver microsomal squalene synthase activity was measured using radioactive farnesyl diphosphate as a substrate and quantitating squalene synthesis by counting the radioactive squalene formed.

Rat liver microsomes, the source of enzyme, were prepared according to the method of Gillies, P. J., et al., Exp. Molec. Pathol. 44: 329–339 (1986), a modification of the procedure of Erickson, S. K., and Cooper, A. D., Metabolism, 29: 991–996 (1980). Approximately 30 μg of microsomal protein was incubated for 10 minutes at 37° C. with 11 μM of $^3$H-farnesyl diphosphate, 49 mCi/mmol, and test compound in the presence of squalene (2 μL), $Mg^{++}$, KF, reduced B-nicotinamide adenine dinucleotide phosphate, dithiothreitol, and $K_2PO_4$, pH 7.35, in a total volume of 200 μL. Oxygen was excluded from the closed incubation tube by degassing with nitrogen. The reaction was terminated by the addition of ethanolic KOH and after degassing with $N_2$, the microsomal membranes were solubilized by heating at 60° C. for 30 minutes. The squalene was extracted into hexane, and the squalene was separated from all other radioactive molecules by passage over an activated alumina column. The solution was collected in scintillation vials, evaporated to dryness, liquid scintillation fluid was added, and the radioactivity was determined in a liquid scintillation counter. The per cent inhibition at a dose of 1 μM compared to controls with no test compound was determined. The % inhibition values for the compounds of the invention are shown in Table 2. The data show that compounds of the invention are inhibitors of squalene synthase.

TABLE 2

In vitro Inhibition of Squalene Synthase

| Ex. No. | % Inhibition at 1 μM | Example No. | % Inhibition at 1 μM |
|---|---|---|---|
| 14 | 47 | 15 | 26* |
| 16 | 25 | 17 | 52 |
| 18 | 89* | 19 | 52* |
| 20 | 41* | 21 | 33* |
| 22 | 47* | 23 | 25* |
| 24 | 85* | 25 | 24 |
| 26 | 33* | 27 | 35 |
| 28 | 49* | 29 | 50* |
| 30 | 63* | 31 | 23 |
| 32 | 40* | 33 | 43* |
| 34 | 29* | 40 | 49 |
| 42 | 36 | 44 | 30 |
| 51 | 27 | 53 | 23 |
| 54 | 23 | 57 | 37 |
| 58 | 50 | 59 | 46 |
| 63 | 44 | 64 | 33 |
| 67 | 47 | 68 | 52 |
| 69 | 23 | 70 | 76 |
| 71 | 25 | 72 | 32 |
| 73 | 24 | 76 | 23 |
| 77 | 23 | 78 | 32 |
| 79 | 54 | 80 | 42 |
| 87 | 76 | 89 | 47 |
| 91 | 41 | 93 | 52 |
| 94 | 20 | 97 | 49 |
| 98 | 55 | 99 | 20 |
| 100 | 46 | 101 | 34 |
| 102 | 48 | | |

*% Inhibition at 10 μM

The compounds of the present invention can be used in the form of salts derived from inorganic or organic acids. These salts include but are not limited to the following: acetate, adipate, alginate, titrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting the carboxylic acid function with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful (in humans and other mammals) for inhibiting protein farnesyltransferase and the farnesylation of Ras. These inhibitors of protein farnesyltransferase are also useful for treating cancer in humans and other mammals. Examples of the kinds of cancers which may be treated with the compounds of the invention include, but are not limited to, lung carcinoma, colorectal carcinoma, exocrine pancreatic carcinoma and myeloid leukemias.

The ability of the compounds of the invention to treat carcinoma can be demonstrated according to the methods referenced below; the determination of in vitro and in vivo antitumor activity of several different classes of compounds is described. Mazerska Z., Woynarowska B., Stefanska B., Borowski S., Drugs Exptl. Clin. Res. 13(6): 345–351 (1987). Bissery, MC, Guenard F, Guerritte-Voegelein F, Lavelie F., Cancer Res. 51: 4845–4852 (1991). Rose W., Anti-cancer Drugs 3: 311–321 (1992). Rygaard J, and Povlsen C. O., Acta Pathol. Microbiol. Scand. 77: 758 (1969).

These inhibitors of protein farnesyltransferase are also useful for preventing restenosis in humans and other mammals. The ability of the compounds of the invention to prevent restenosis can be demonstrated according to the methods described by Kranzhofer, R. et al. Circ. Res. 73: 264–268 (1993), Mitsuka, M. et al. Circ. Res. 73: 269–275 (1993) and Santoian, E. C. et al. Circulation 88: 11–14 (1993).

The compounds of the invention are also useful (in humans and other mammals) for inhibiting squalene synthase. The compounds of the invention are also useful for inhibiting cholesterol biosynthesis. The compounds of the invention are also useful for treating atherosclerosis and inhibiting progression of atherosclerosis. The compounds of the invention are also useful for treating hyperlipidemia. The compounds of the invention are also useful for treating fungal infections.

The compounds of the invention are also useful for treating acne in humans. Methods to demonstrate this activity, appropriate doses and means of administration are disclosed in PCT patent application WO 94/22870, published Oct. 13, 1994 which is incorporated herein by reference.

The ability of the compounds of the invention to inhibit cholesterol biosynthesis can be demonstrated in vivo according to the following method. The in vivo inhibition of cholesterol synthesis can be determined in a monkey model in which the monkeys are dosed, fasted overnight and bled in the morning. Plasma samples are prepared and analyzed for total cholesterol, HDL-cholesterol and triglycerides.

The ability of the compounds of the invention to treat fungal infections can be demonstrated according to the method described by S. Shadomy and M. A. Pfaller. 1991. Laboratory Studies with Antifungal Agents: Susceptibility Tests and Quantitation in Body Fluids, pp. 1173–1183. In A. Balows, W. J. Hausler, Jr., K. L. Herrmann, H. Isenberg and H. J. Shadomy, Eds. Manual of Clinical Microbiology, 5th Ed. American Society for Microbiology, Washington, D.C. The antifungal activity of squalene synthase inhibitors has been reported by a number of researchers including Dufresne, et al., Tetrahedron 48/47 10221–10226 (1992) and Dawson, M. J., et al., J. Antibiot. (Tokyo) 45: 639–647 (1992).

For use as a chemotherapeutic agent, the total daily dose administered to a host in single or divided doses may be in amounts, for example, from 0.01 to 500 mg/kg body weight daily, preferably in amounts from 0.1 to 20 mg/kg body weight daily and more preferably in amounts from 0.5 to 10 mg/kg body weight daily. Dosage unit compositions may contain such amounts of submultiples thereof to make up the daily dose.

For use as a lipid lowering or antifungal agent, the total daily dose administered to a host in single or divided doses may be in amounts, for example, from 0.001 to 1000 mg/kg body weight daily and more preferred from 1.0 to 30 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capabale of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

While the compounds of the invention can be administered as the sole active pharmaceutical agent for the treatment of cancer, they can also be used in combination with one or more other chemotherapeutic agents.

Representative examples of chemotherapeutic agents are described in Holleb, et al., *Clinical Oncology*, American Cancer Society, United States (1991) p 56 et seq. These agents include alkylating agents such as the nitrogen mustards (mechloethamine, melphalan, chlorambucil, cyclophosphamide and ifosfamide), nitrosoureas (carmustine, lomustine, semustine, streptozocin), alkyl sulfonates (busulfan), triazines (dacarbazine) and ethyenimines (thiotepa, hexamethylmelamine); folic acid analogues (methotrexate); pyrimidine analogues (5-fluorouracil, cytosine arabinoside); purine analogues (6-mercaptopurine, 6-thioguanine); antitumor antibiotics (actinomycin D, the antracyclines (doxorubicin), bleomycin, mitomycin C, methramycin); plant alkaloids such as vinca alkaloids (vincristine, vinblastine) and etoposide (VP-16); hormones and hormone antagonists (tamoxifen and corticosteroids); and miscellaneous agents (cisplatin, taxol, brequinar).

The above compounds to be employed in combination with the farnesyl protein transferase inhibitor of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other chemotherapeutic agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

While the compounds of the invention can be administered as the sole active pharmaceutical agent for lipid lowering, they can also be used in combination with one or more other cardiovascular agents independently selected from HMG CoA reductase inhibitors, antihyperlipoproteinemic agents and serum cholesterol lowering agents.

Representative HMG CoA reductase inhibitors include lovastatin, pravastatin, velostatin, simvastatin and the like.

Representative antihyperlipoproteinemic agents include probucol and the like.

Representative serum cholesterol lowering agents include Lopid® (gemfibrozil), bile acid sequestrants such as cholestyramine, colestipol, polidexide (DEAE-Sephadex), clofibrate, nicotinic acid and its derivatives, neomycin, p-aminosalicylic acid, bezafibrate and the like.

The above compounds to be employed in combination with the squalene synthase inhibitor of the invention wile be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other cardiovascular agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula

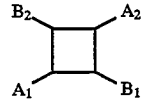

wherein
  $A_1$ and $A_2$ are independently —C(O)NR$_1$R$_2$ wherein
    $R_1$ at each occurrence is independently selected from
      (i) hydrogen,
      (ii) loweralkyl,
      (iii) cycloalkyl,
      (iv) cycloalkylalkyl,
      (v) aryl,
      (vi) arylalkyl,
      (vii) alkenyl,
      (viii) alkynyl,
      (ix) carboxyalkyl,
      (x) heterocyclicalkyl,
      (xi) aryloxyarylalkyl,
      (xii) aryloxyalkyl,
      (xiii) arylalkyl substituted arlyalkyl,
      (xiv) arylalkoxyarylalkyl,
      (xv) arylalkoxyaryl, and
    $R_2$ at each occurrence is independently selected from
      (i) aryl, (ii) arylalkyl,
(iii) alkenyl,
(iv) alkynyl,
(v) arylalkenyl,
(vi) arylalkynyl,
(vii) heterocyclicalkyl,
(viii) aryloxyalkyl,
(ix) arylalkyl wherein the alkyl group is substituted with —$OR_{10}$ wherein $R_{10}$ is hydrogen or alkanoyl and
(x) aryl, arylalkyl or heterocyclicalkyl wherein the aryl group, the aryl part of the arylalkyl group or the heterocyclic part of the heterocyclicalkyl group is substituted with —Y—$R_3$ wherein at each occurrence Y is independently selected from
(a) a covalent bond,
(b) —C(O)—,
(c) —$CH_2$—,
(d) —O—,
(e) —S—,
(f) —NH—,
(g) —$CH_2O$—,
and at each occurrence $R_3$ is independently selected from
(a) aryl,
(b) arylalkyl,
(c) cycloalkyl,
(d) cycloalkylalkyl,
(e) heterocyclic and
(f) (heterocyclic)alkyl,
or $R_1$ and $R_2$ taken together with the nitrogen atom to which they are attached form a nitrogen-containing heterocycle;
$B_1$ and $B_2$ are independently —C(O)—$OR_7$ wherein at each occurrence $R_7$ is independently selected from hydrogen and a carboxy protecting group;
or a pharmaceutically acceptable salt thereof.

2. A compound as defined by claim 1 wherein
$A_1$ and $A_2$ are independently —C(O)$NR_1R_2$ wherein at each occurrence at each occurrence $R_1$ is independently selected from (i) loweralkyl, (ii) arylalkyl, (iii) cycloalkyl, (iv) carboxyalkyl, and (v) heterocyclicalkyl and at each occurrence $R_2$ is independently selected from (i) arylalkyl, (ii) arylalkenyl, and (iii) arylalkyl or heterocyclicalkyl wherein the the aryl part of the arylalkyl group or the heterocyclic part of the heterocyclicalkyl group is substituted with —Y—$R_3$ wherein at each occurrence Y is independently selected from (a) —$CH_2$— and (b) —O—, at each occurrence $R_3$ is independently selected from (a) aryl, (b) arylalkyl, (c) heterocyclic and (d) (heterocyclic)alkyl, or $R_1$ and $R_2$ taken together with the nitrogen atom to which they are attached form a nitrogen-containing heterocycle; and
$B_1$ and $B_2$ are independently —C(O)—$OR_7$ wherein at each occurrence $R_7$ is independently selected from hydrogen and a carboxy protecting group;
or a pharmaceutically acceptable salt thereof.

3. A compound as defined by claim 1 wherein
$A_1$ and $A_2$ are independently —C(O)$NR_1R_2$ wherein at each occurrence $R_1$ is independently selected from (i) loweralkyl, (ii) arylalkyl, (iii) cycloalkyl, (iv) carboxyalkyl, and (v) heterocyclicalkyl and at each occurrence $R_2$ is independently selected from 4-(phenoxy)benzyl, 3-(phenoxy)benzyl, 3-(4-fluorophenoxy)benzyl, 4-(benzyl)benzyl, benzyl, 5-phenylpentyl, 4-(phenoxymethyl)benzyl, 4-acetoxy-5-methyl-6-phenylhexyl, 2-methyl-5-phenylpentyl, and E-2-methyl-5-phenylpent-4-enyl, or $R_1$ and $R_2$ taken together with the nitrogen atom to which they are attached is 4-(4-phenoxyphenyl)-1,2,3,6-tetrahydropyridin-1-yl; and
$B_1$ and $B_2$ are independently —C(O)—$OR_7$ wherein at each occurrence $R_7$ is independently selected from hydrogen and a carboxy protecting group;
or a pharmaceutically acceptable salt thereof.

4. A compound as defined by claim 1 wherein
$A_1$ and $A_2$ are independently —C(O)$NR_1R_2$ wherein at each occurrence $R_1$ is independently selected from (i) loweralkyl, (ii) cycloalkyl, (iii) benzyl, (iv) 4-fluorobenzyl, (v) 1-phenylethyl, (vi) carboxymethyl, (vii) furan-2-ylmethyl and thien-2-ylmethyl and at each occurrence $R_2$ is independently selected from 4-(phenoxy)benzyl, 3-(phenoxy)benzyl, 3-(4-fluorophenoxy)benzyl, 4-(benzyl)benzyl, benzyl, 5-phenylpentyl, 4-(phenoxymethyl)benzyl, 4-acetoxy-5-methyl-6-phenylhexyl, 2-methyl-5-phenylpentyl, and E-2-methyl-5-phenylpent-4-enyl, or $R_1$ and $R_2$ taken together with the nitrogen atom to which they are attached is 4-(4-phenoxyphenyl)-1,2,3,6-tetrahydropyridin-1-yl; and
$B_1$ and $B_2$ are independently —C(O)—$OR_7$ wherein at each occurrence $R_7$ is independently selected from hydrogen and a carboxy protecting group;
or a pharmaceutically acceptable salt thereof.

5. A compound of the formula

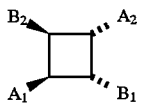

wherein
$A_1$ and $A_2$ are independently—C(O)$NR_1R_2$ wherein
$R_1$ at each occurrence is independently selected from
(i) hydrogen,
(ii) loweralkyl,
(iii) cycloalkyl,
(iv) cycloalkylalkyl,
(v) aryl,
(vi) arylalkyl,
(vii) alkenyl,
(viii) alkynyl,
(ix) carboxyalkyl,
(x) heterocyclicalkyl,
(xii) aryloxyarylalkyl,
(xiii) arylalkyl substituted arylalkyl,
(xiv) aryloxyaryl,
(xv) arylalkoxyarylalkyl,
(xvi) arylalkoxyaryl, and
$R_2$ at each occurrence is independently selected from
(i) aryl,
(ii) arylalkyl,
(iii) alkenyl,
(iv) alkynyl,
(v) arylalkenyl,
(vi) arylalkynyl,
(vii) heterocyclicalkyl,
(viii) aryloxyalkyl,
(ix) arylalkyl wherein the alkyl group is substituted with —$OR_{10}$ wherein $R_{10}$ is hydrogen or alkanoyl and (x) aryl, arylalkyl or heterocyclicalkyl wherein the aryl group, the aryl part of the arylalkyl group or the heterocyclic part of the heterocyclicalkyl group is substituted with —Y—$R_3$ wherein at each occurrence Y is independently selected from
(a) a covalent bond,
(b) —C(O)—,
(c) —$CH_2$—,
(d) —O—,
(e) —S—,
(f) —NH—,
(g) —$CH_2O$—, and at each occurrence $R_3$ is independently selected from
(a) aryl,
(b) arylalkyl,
(c) cycloalkyl,
(d) cycloalkylalkyl,
(e) heterocyclic and
(f) (heterocyclic)alkyl, or $R_1$ and $R_2$ taken together with the nitrogen atom to which they are attached form a nitrogen-containing heterocycle;

$B_1$ and $B_2$ are independently —C(O)—$OR_7$ wherein at each occurrence $R_7$ is independently selected from hydrogen and a carboxy protecting group;

or a pharmaceutically acceptable salt thereof.

6. A compound as defined by claim 5 wherein $A_1$ and $A_2$ are independently —C(O)$NR_1R_2$ wherein at each occurrence $R_1$ is independently selected from (i) hydrogen, (ii) loweralkyl, (iii) cycloalkyl, (iv) cycloalkylalkyl, (v) aryl, (vi) arylalkyl, (vii) arylalkyl substituted arylalkyl, (viii) aryloxyaryl, (ix) aryloxyarylalkyl, (x) arylalkoxyarylalkyl, (xi) arylalkoxyaryl, (xii) alkenyl, (xiii) alkynyl, (xiv) carboxyalkyl, and (xv) heterocyclicalkyl; and $R_2$ at each occurrence is independently selected from (i) aryl, (ii) arylalkyl, (iii) alkenyl, (iv) alkynyl, (v) arylalkenyl, (vi) arylalkynyl, (vii) heterocyclicalkyl, (viii) aryloxyalkyl, (ix) arylalkyl wherein the alkyl group is substituted with —$OR_{10}$ wherein $R_{10}$ is hydrogen or alkanoyl and (x) aryl, arylalkyl or heterocyclicalkyl wherein the aryl group, the the aryl part of the arylalkyl group or the heterocyclic part of the heterocyclicalkyl group is substituted with —Y—$R_3$ wherein at each occurrence Y is independently selected from (a) a covalent bond, (b) —C(O)—, (c) —$CH_2$—, (d) —O—, (e) —S—, (f) —NH—, and (g) —$CH_2O$—, and at each occurrence $R_3$ is independently selected from (a) aryl, (b) arylalkyl, (c) cycloalkyl, (d) cycloalkylalkyl, (e) heterocyclic and (f) (heterocyclic)alkyl, or $R_1$ and $R_2$ taken together with the nitrogen atom to which they are attached form a nitrogen-containing heterocycle; and $B_1$ and $B_2$ are independently —C(O)—$OR_7$ wherein at each occurrence $R_7$ is independently selected from hydrogen and a carboxy protecting group;

or a pharmaceutically acceptable salt thereof.

7. A compound as defined by claim 5 wherein $A_1$ and $A_2$ are independently —C(O)$NR_1R_2$ wherein at each occurrence at each occurrence $R_1$ is independently selected from (i) loweralkyl, (ii) arylalkyl, (iii) cycloalkyl, (iv) carboxyalkyl, and (v) heterocyclicalkyl and at each occurrence $R_2$ is independently selected from (i) arylalkyl, (ii) arylalkenyl, and (iii) arylalkyl or heterocyclicalkyl wherein the the aryl part of the arylalkyl group or the heterocyclic part of the heterocyclicalkyl group is substituted with —Y—$R_3$ wherein at each occurrence Y is independently selected from (a) —$CH_2$— and (b) —O—, at each occurrence $R_3$ is independently selected from (a) aryl, (b) arylalkyl, (c) heterocyclic and (d) (heterocyclic)alkyl, or $R_1$ and $R_2$ taken together with the nitrogen atom to which they are attached form a nitrogen-containing heterocycle; and $B_1$ and $B_2$ are independently —C(O)—$OR_7$ wherein at each occurrence $R_7$ is independently selected from hydrogen and a carboxy protecting group;

or a pharmaceutically acceptable salt thereof.

8. A compound as defined by claim 5 wherein $A_1$ and $A_2$ are independently —C(O)$NR_1R_2$ wherein at each occurrence $R_1$ is independently selected from (i) loweralkyl, (ii) arylalkyl, (iii) cycloalkyl, (iv) carboxyalkyl, and (v) heterocyclicalkyl and at each occurrence $R_2$ is independently selected from 4-(phenoxy)benzyl, 3-(phenoxy)benzyl, 3-(4-fluorophenoxy)benzyl, 4-(benzyl)benzyl, benzyl, 5-phenylpentyl, 4-(phenoxymethyl)benzyl, 4-acetoxy-5-methyl-6-phenylhexyl, 2-methyl-5-phenylpentyl, and E-2-methyl-5-phenylpent-4-enyl, or $R_1$ and $R_2$ taken together with the nitrogen atom to which they are attached is 4-(4-phenoxyphenyl)-1,2,3,6-tetrahydropyridin-1-yl; and $B_1$ and $B_2$ are independently —C(O)—$OR_7$ wherein at each occurrence $R_7$ is independently selected from hydrogen and a carboxy protecting group;

or a pharmaceutically acceptable salt thereof.

9. A compound as defined by claim 5 wherein $A_1$ and $A_2$ are independently —C(O)$NR_1R_2$ wherein at each occurrence $R_1$ is independently selected from (i) loweralkyl, (ii) cycloalkyl, (iii) benzyl, (iv) 4-fluorobenzyl, (v) 1-phenylethyl, (vi) carboxymethyl, (vii) furan-2-ylmethyl and thien-2-ylmethyl and at each occurrence $R_2$ is independently selected from 4-(phenoxy)benzyl, 3-(phenoxy)benzyl, 3-(4-fluorophenoxy)benzyl, 4-(benzyl)benzyl, benzyl, 5-phenylpentyl, 4-(phenoxymethyl)benzyl, 4-acetoxy-5-methyl-6-phenylhexyl, 2-methyl-5-phenylpentyl, and E-2-methyl-5-phenylpent-4-enyl, or $R_1$ and $R_2$ taken together with the nitrogen atom to which they are attached is 4-(4-phenoxyphenyl)-1,2,3,6-tetrahydropyridin-1-yl; and $B_1$ and $B_2$ are independently —C(O)—$OR_7$ wherein at each occurrence $R_7$ is independently selected from hydrogen and a carboxy protecting group;

or a pharmaceutically acceptable salt thereof.

10. A compound selected from the group consisting of:
($1\alpha,2\beta,3\beta,4\alpha$)-1,3-Di[N-benzyl-N-(4-phenoxybenzyl)-aminocarbonyl]cyclobutane-2,4-dicarboxylic acid;
($1\alpha,2\beta,3\beta,4\alpha$)-1,3-Di[N-ethyl-N-(4-phenoxybenzyl)-aminocarbonyl]cyclobutane-2,4-dicarboxylic acid;
($1\alpha,2\beta,3\beta,4\alpha$)-1,3-Di[N-methyl-N-(3-phenoxybenzyl)-aminocarbonyl]cyclobutane-2,4-dicarboxylic acid;
($1\alpha,2\beta,3\beta,4\alpha$)-1,3-Di[N-methyl-N-(3-(4-fluorophenoxy)benzyl)-aminocarbonyl]cyclobutane-2,4-dicarboxylic acid;
($1\alpha,2\beta,3\beta,4\alpha$)-1,3-Di[N-propyl-N-(4-benzylbenzyl)-aminocarbonyl]cyclobutane-2,4-dicarboxylic acid;
($1\alpha,2\beta,3\beta,4\alpha$)-1,3-Di[N-(n-butyl)-N-(4-phenoxybenzyl)-aminocarbonyl]cyclobutane-2,4-dicarboxylic acid;
($1\alpha,2\beta,3\beta,4\alpha$)-1,3-Di[N-cyclopropyl-N-(4-phenoxybenzyl)-aminocarbonyl]cyclobutane-2,4-dicarboxylic acid;
($1\alpha,2\beta,3\beta,4\alpha$)-1,3-Di[N,N-dibenzylaminocarbonyl]cyclobutane-2,4-dicarboxylic acid;
($1\alpha,2\beta,3\beta,4\alpha$)-1,3-Di[N-propyl-N-(5-phenylpentyl)-aminocarbonyl]cyclobutane-2,4-dicarboxylic acid;
($1\alpha,2\beta,3\beta,4\alpha$)-1-[N-Propyl-N-(4-phenoxybenzyl)-aminocarbonyl]-3-[N-benzyl-N-(4-phenoxybenzyl)aminocarbonyl]cyclobutane-2,4-dicarboxylic acid;

(1α,2β,3β,4α)-1,3-Di[N-carboxymethyl-N-(4-phenoxybenzyl)-aminocarbonyl]cyclobutane-2,4-dicarboxylic acid;

(1α,2β,3β,4α)-1,3-Di[N-propyl-N-(4-phenoxymethylbenzyl)-aminocarbonyl]-2,4-cyclobutanedicarboxylic acid;

(1α,2β,3β,4α)-1,3-Di[N-(furan-2-ylmethyl)-N-(4-phenoxybenzyl)-aminocarbonyl]cyclobutane-2,4-dicarboxylic acid;

(1α,2β,3β,4α)-1,3-Di[N-(thien-2-ylmethyl)-N-(4-phenoxybenzyl)-aminocarbonyl]cyclobutane-2,4-dicarboxylic acid;

(1α,2β,3β,4α)-1,3-Di [N-benzyl-N-{syn-(4-acetoxy-5-methyl)-6-phenylhexyl}aminocarbonyl]cyclobutane-2,4-dicarboxylic acid;

(1α,2β,3β,4α)-1,3-Di[N-benzyl-N-((2R)-5-phenyl-2-methylpentyl)-aminocarbonyl]cyclobutane-2,4-dicarboxylic acid;

(1α,2β,3β,4α)-1,3-Di [N-benzyl-N-{(E)-(2R)-2-methyl-5-phenyl-4-pentenyl}aminocarbonyl]cyclobutane-2,4-dicarboxylic acid;

(1α,2β,3β,4α)-1,3-Di[N-(S)-α-Methylbenzyl-N-(4-phenoxybenzyl)-aminocarbonyl]cyclobutane-2,4-dicarboxylic acid;

(1α,2β,3β,4α)-1,3-Di[4-(4-phenoxyphenyl)-1,2,3,6-tetrahydropyridin-1-ylcarbonyl]cyclobutane-2,4-dicarboxylic acid; and (1α,2β,3β,4α)-1,3-Di[N-(4-fluorobenzyl)-N-(4-phenoxybenzyl)-aminocarbonyl]cyclobutane-2,4-dicarboxylic acid;

or a pharmaceutically acceptable salt thereof.

11. A pharmaceutical composition for inhibiting protein farnesyltransferase comprising a therapeutically effective amount of a compound according to claim 1 and a pharmaceutically acceptable carrier.

12. A pharmaceutical composition for inhibiting squalene synthase comprising a therapeutically effective amount of a compound according to claim 1 and a pharmaceutically acceptable carrier.

13. A pharmaceutical composition for inhibiting protein farnesyltransferase comprising a therapeutically effective amount of a compound according to claim 5 and a pharmaceutically acceptable carrier.

14. A pharmaceutical composition for inhibiting squalene synthase comprising a therapeutically effective amount of a compound according to claim 5 and a pharmaceutically acceptable carrier.

* * * * *